US008603993B2

(12) United States Patent
Ma et al.

(10) Patent No.: US 8,603,993 B2
(45) Date of Patent: Dec. 10, 2013

(54) COMPOSITIONS AND METHODS MODULATING MG29 FOR THE TREATMENT OF DIABETES

(75) Inventors: Jianjie Ma, Belle Mead, NJ (US); Noah Weisleder, Elizabeth, NJ (US); Hua Zhu, Piscataway, NJ (US); Peihui Lin, Piscataway, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 381 days.

(21) Appl. No.: 12/794,006

(22) Filed: Jun. 4, 2010

(65) Prior Publication Data

US 2011/0034533 A1 Feb. 10, 2011

Related U.S. Application Data

(63) Continuation-in-part of application No. 12/504,331, filed on Jul. 16, 2009.

(60) Provisional application No. 61/217,926, filed on Jun. 5, 2009.

(51) Int. Cl.
C12N 15/11 (2006.01)
A61K 48/00 (2006.01)
C07H 21/02 (2006.01)
C07H 21/04 (2006.01)

(52) U.S. Cl.
USPC .................. 514/44 A; 514/44 R; 536/24.5

(58) Field of Classification Search
USPC .............................................. 514/44
See application file for complete search history.

(56) References Cited

U.S. PATENT DOCUMENTS

| 2003/0170838 A1 | 9/2003 | Mishra et al. |
| 2004/0029222 A1 | 2/2004 | Edinger et al. |
| 2005/0181400 A1* | 8/2005 | Monia et al. ............ 435/6 |
| 2010/0017901 A1* | 1/2010 | Ma et al. ............ 800/13 |

FOREIGN PATENT DOCUMENTS

| JP | 2006-122048 | 5/2006 |
| WO | WO 02-24733 A2 | 3/2002 |

OTHER PUBLICATIONS

Thorton, Angela. Regulation of Store-Operated Calcium Channel by mitsugumin29 in Skeletal Muscle Aging, Graduate Dissertation dated Jan. 2009, pp. 1-103.*
Hammond et al. (Nature Reviews Genetics 2001, vol. 2:110-119).*
Written Opinion of Int'l Searching Authority for PCT/US2010/037389.
Komazaki, S., et al., "Abnormal Formation of Sarcoplasmic Reticulum Networks and Triads During Early Development of Skeletal Muscle Cells in Mitsugumin29-Deficient Mice", Dev. Groeth Differ., vol. 43(6), p. 717-723(Dec. 2001).
NCBI Accession No. NP_001035799 (Jun. 26, 2007).
NCBI Accession No. BC113102 (Oct. 4, 2006).
File history for U.S. Appl. No. 12/504,331.
*ISR and Written Opinion of Int'l Searching Authority for PCT/US2009/050846.*

* cited by examiner

*Primary Examiner* — Terra Cotta Gibbs
(74) *Attorney, Agent, or Firm* — McCarter & English, LLP

(57) ABSTRACT

Disclosed herein are compositions and methods for treatment of muscle dysfunction, including diabetes. In addition, the invention relates to therapeutic compositions comprising nucleotides and/or polypeptides of the invention in combination with a pharmaceutically acceptable carrier, wherein the composition facilitates the treatment of skeletal muscle disorders. Moreover, the invention relates to the treatment and/or prevention of pathological conditions associated with altered intracellular Ca2+ regulation and disrupted membrane structure that occurs when the expression levels of MG29 are reduced.

18 Claims, 17 Drawing Sheets a

$P_{sMCK}$: Small muscle creatine kinase (MCK) promoter, Muscle-specific weak promoter
TR: Terminal repeat sequence
sPoly(A): Short poly(A) signal $P_{TCK4}$: Triple modified MCK promoter, Muscle-specific strong promoter b c

SEQUENCE LISTING

<160> NUMBER OF SEQ ID NOS: 26

<210> SEQ ID NO 1
<211> LENGTH: 264
<212> TYPE: PRT
<213> ORGANISM: Mus musculus
<220> FEATURE:
<221> NAME/KEY: MISC_FEATURE
<222> LOCATION: (1)..(264)
<223> OTHER INFORMATION: Mouse MG29

<400> SEQUENCE: 1

Met Ser Ser Thr Glu Ser Pro Gly Arg Thr Ser Asp Lys Ser Pro Arg
1               5                   10                  15

Gln Gln Val Asp Arg Leu Leu Leu Gly Leu Arg Trp Gln Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Leu Val
    50                  55                  60

Leu Cys Asn Asn Glu Ala Lys Asp Val Ser Ser Ile Ile Val Leu Phe
65                  70                  75                  80

Gly Tyr Pro Phe Arg Leu Tyr Gln Val Gln Tyr Glu Met Pro Leu Cys
                85                  90                  95

Asp Gln Asp Ser Thr Ser Lys Thr Met Asn Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Lys Leu Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Leu Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                245                 250                 255

Glu Gln Gly Ala Val Glu Lys Gln
            260

<210> SEQ ID NO 2
<211> LENGTH: 264
<212> TYPE: PRT
<213> ORGANISM: Oryctolagus cuniculus
<220> FEATURE:
<221> NAME/KEY: MISC_FEATURE
<222> LOCATION: (1)..(264)
<223> OTHER INFORMATION: Rabbit MG29

<400> SEQUENCE: 2

Met Ser Ser Thr Glu Ser Pro Ser Arg Ala Ala Asp Lys Ser Pro Arg

```
           1               5                  10                 15
Gln Gln Val Asp Arg Leu Leu Glu Gly Leu Arg Trp Arg Arg Leu Glu
                20                  25                  30

Glu Pro Leu Gly Phe Ile Lys Val Leu Gln Trp Leu Phe Ala Ile Phe
                35                  40                  45

Ala Phe Gly Ser Cys Gly Ser Tyr Ser Gly Glu Thr Gly Ala Met Val
            50                  55                  60

Arg Cys Asn Asn Glu Ala Lys Asp Val Ser Ile Ile Val Leu Phe
65                  70                  75                  80

Gly Tyr Pro Phe Arg Leu His Arg Ile Glu Tyr Glu Met Pro Leu Cys
                    85                  90                  95

Asp Asp Asp Ser Ser Ser Lys Thr Met His Leu Met Gly Asp Phe Ser
                100                 105                 110

Ala Pro Ala Glu Phe Phe Val Thr Leu Gly Ile Phe Ser Phe Phe Tyr
                115                 120                 125

Thr Met Ala Ala Leu Val Val Tyr Leu Arg Phe His Lys Leu Tyr Thr
                130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                    165                 170                 175

Asp Val Lys Gly Ala Thr Arg Pro Ser Ser Leu Thr Ala Ala Met Ser
                180                 185                 190

Val Cys His Gly Glu Glu Ala Val Cys Ser Ala Gly Ala Thr Pro Ser
                195                 200                 205

Met Gly Leu Ala Asn Ile Ser Val Leu Phe Gly Phe Ile Asn Phe Phe
                210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                    245                 250                 255

Glu Gln Gly Ala Val Glu Lys Gln
                260
```

<210> SEQ ID NO 3
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)
<223> OTHER INFORMATION: Human MG29

<400> SEQUENCE: 3

```
Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
                20                  25                  30

Glu Pro Leu Gly Phe Ile Lys Val Leu Gln Trp Leu Phe Ala Ile Phe
                35                  40                  45

Ala Phe Gly Ser Cys Gly Ser Tyr Ser Gly Glu Thr Gly Ala Met Val
            50                  55                  60

Arg Cys Asn Asn Glu Ala Lys Asp Val Ser Ser Ile Ile Val Ala Phe
65                  70                  75                  80

Gly Tyr Pro Phe Arg Leu His Arg Ile Gln Tyr Glu Met Pro Leu Cys
                    85                  90                  95
```

```
Asp Glu Glu Ser Ser Ser Lys Thr Met His Leu Met Gly Asp Phe Ser
                100                 105                 110

Ala Pro Ala Glu Phe Phe Val Thr Leu Gly Ile Phe Ser Phe Phe Tyr
            115                 120                 125

Thr Met Ala Ala Leu Val Ile Tyr Leu Arg Phe His Asn Leu Tyr Thr
        130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Ile Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Gly Gln Asp Gln Asp Gln Asp Gln Asp Gln Gly Gln
                245                 250                 255

Gly Pro Ser Gln Glu Ser Ala Ala Glu Gln Gly Ala Val Glu Lys Gln
            260                 265                 270
```

<210> SEQ ID NO 4
<211> LENGTH: 236
<212> TYPE: PRT
<213> ORGANISM: Homo sapiens
<220> FEATURE:
<221> NAME/KEY: MISC_FEATURE
<222> LOCATION: (1)..(236)
<223> OTHER INFORMATION: Human MG29v2 (Q5VXT5-2)

<400> SEQUENCE: 4

```
Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Met Val
    50                  55                  60

Arg Cys Asn Asn Glu Ala Lys Asp Val Ser Ser Ile Ile Val Ala Phe
65                  70                  75                  80

Gly Tyr Pro Phe Arg Leu His Arg Ile Gln Tyr Glu Met Pro Leu Cys
                85                  90                  95

Asp Glu Glu Ser Ser Ser Lys Thr Met His Leu Met Gly Asp Phe Ser
                100                 105                 110

Ala Pro Ala Glu Phe Phe Val Thr Leu Gly Ile Phe Ser Phe Phe Tyr
            115                 120                 125

Thr Met Ala Ala Leu Val Ile Tyr Leu Arg Phe His Asn Leu Tyr Thr
        130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190
```

```
Val Cys His Gly Glu Glu Ala Val Cys Ser Ala Gly Ala Thr Pro Ser
        195                 200                 205

Met Gly Leu Ala Asn Ile Ser Val Val Arg Pro Val Ala Thr Ala Gly
        210                 215                 220

Ser Ser Thr Ser Pro Ala Ala Gln Ala Cys Pro Ser
225                 230                 235

<210> SEQ ID NO 5
<211> LENGTH: 264
<212> TYPE: PRT
<213> ORGANISM: Bos taurus
<220> FEATURE:
<221> NAME/KEY: MISC_FEATURE
<222> LOCATION: (1)..(264)
<223> OTHER INFORMATION: Bovine MG29

<400> SEQUENCE: 5

Met Ser Ser Thr Glu Ser Ser Arg Thr Ala Asp Lys Ser Pro Arg
1                5                  10                  15

Gln Gln Val Asp Arg Leu Leu Val Gly Leu Arg Trp Arg Arg Leu Glu
        20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Thr Gly Ala Thr Val
50                  55                  60

Arg Cys Asn Asn Glu Ala Lys Asp Val Ser Ala Ile Val Ser Phe
65                  70                  75                  80

Gly Tyr Pro Phe Arg Leu Asn Arg Val Gln Tyr Glu Met Pro Leu Cys
                85                  90                  95

Asp Asp Glu Ser Thr Ser Lys Thr Met His Leu Met Gly Asp Phe Ser
            100                 105                 110

Ala Pro Ala Glu Phe Phe Val Thr Leu Gly Ile Phe Ser Phe Phe Tyr
            115                 120                 125

Thr Ile Ala Ala Leu Val Ile Tyr Leu Arg Phe His Lys Leu Tyr Thr
        130                 135                 140

Glu Asn Arg Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
            195                 200                 205

Met Gly Leu Ala Asn Ile Ser Val Leu Phe Gly Phe Ile Asn Phe Phe
            210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Thr Ser Pro Glu Ser Ala Ala
                245                 250                 255

Glu Gln Gly Ala Val Glu Lys Gln
            260

<210> SEQ ID NO 6
<211> LENGTH: 251
<212> TYPE: PRT
<213> ORGANISM: Xenopus laevis
<220> FEATURE:
<221> NAME/KEY: MISC_FEATURE
```

<222> LOCATION: (1)..(251)
<223> OTHER INFORMATION: X laevis MG29

<400> SEQUENCE: 6

```
Met Asp Arg Leu Gly Gly Leu Ala Gly Leu Gly Lys Lys Asn Pro Phe
1               5                   10                  15

Ala Gly Leu Arg Trp Arg Arg Leu Glu Glu Pro Leu Gly Phe Ile Lys
            20                  25                  30

Leu Leu Glu Trp Leu Phe Ala Ile Phe Ala Phe Gly Cys Gly Ser
        35                  40                  45

Tyr Ser Gly Glu Thr Ala Ala Thr Val Met Cys Lys Ser Glu Ala Asp
    50                  55                  60

Thr Glu Ile Lys Leu Ile Ser Val Pro Phe Gly Tyr Pro Phe Arg Leu
65                  70                  75                  80

Tyr Arg Gln Arg Tyr Glu Met Pro Ala Cys Asp Asp Met Glu Arg Arg
                85                  90                  95

Ile Leu His Leu Thr Gly Asp Phe Ser Ala Pro Ala Glu Phe Val
            100                 105                 110

Thr Met Gly Val Phe Ala Phe Leu Tyr Ala Met Phe Ala Leu Val Ile
            115                 120                 125

Tyr Leu Arg Phe His Glu Glu Tyr Thr Lys Ile Arg Arg Leu Pro Ile
    130                 135                 140

Val Asp Leu Cys Val Thr Gly Ala Phe Thr Phe Leu Trp Leu Val Ala
145                 150                 155                 160

Ala Ser Ala Trp Gly Lys Gly Leu Met Asp Val Lys Val Ala Thr Gln
                165                 170                 175

Pro Ser Ser Leu Val Ser Ser Met Pro Leu Cys Gln Met Glu Lys Ala
            180                 185                 190

Thr Cys Asn Ala Gly Ser Ser Pro Tyr Phe Ala Leu Ala Asn Ile Ser
        195                 200                 205

Val Leu Phe Gly Phe Leu Asn Phe Ile Ile Trp Ala Ala Asn Ile Trp
    210                 215                 220

Phe Val Phe Lys Glu Thr Thr Trp Ser Lys Lys Pro Ala Ser Lys Glu
225                 230                 235                 240

Glu Ser Ala Glu Arg Gly Glu Val Glu Asp His
                245                 250
```

<210> SEQ ID NO 7
<211> LENGTH: 254
<212> TYPE: PRT
<213> ORGANISM: Xenopus tropicalis
<220> FEATURE:
<221> NAME/KEY: MISC_FEATURE
<222> LOCATION: (1)..(254)
<223> OTHER INFORMATION: X. tropicalis MG29

<400> SEQUENCE: 7

```
Met Asp Arg Glu Gly Gly Leu Ala Gly Leu Gly Lys Lys Asn Pro Leu
1               5                   10                  15

Ala Gly Leu Arg Trp Arg Arg Leu Glu Glu Pro Leu Gly Phe Ile Lys
            20                  25                  30

Leu Leu Glu Trp Leu Phe Ala Ile Phe Ala Phe Gly Cys Cys Gly Ser
        35                  40                  45

Tyr Ser Gly Glu Thr Ala Ala Thr Val Met Cys Lys Thr Glu Thr Asp
    50                  55                  60

Ser Asp Thr Glu Ile Lys Leu Ile Ser Val Pro Phe Ala Tyr Pro Phe
65                  70                  75                  80
```

```
Arg Leu Tyr Arg Gln Arg Tyr Glu Met Pro Ala Cys Glu Asp Ile Glu
                85                  90                  95

Arg Arg Ile Leu His Leu Thr Gly Asp Phe Ser Ala Pro Ala Glu Phe
            100                 105                 110

Phe Val Thr Met Gly Val Phe Ala Phe Leu Tyr Ser Met Phe Ala Leu
        115                 120                 125

Val Val Tyr Leu Arg Phe His Glu Glu Tyr Thr Lys Ile Arg Arg Val
    130                 135                 140

Pro Ile Val Asp Leu Cys Val Thr Gly Ala Phe Ala Phe Leu Trp Leu
145                 150                 155                 160

Val Ala Ala Ser Ala Trp Gly Lys Gly Leu Met Asp Val Lys Val Ala
                165                 170                 175

Thr Gln Pro Ser Asn Leu Val Ser Ser Met Pro Leu Cys Gln Met Glu
            180                 185                 190

Lys Ala Thr Cys Asn Ala Gly Ser Gln Pro Tyr Phe Ala Leu Ala Asn
        195                 200                 205

Ile Ser Val Leu Phe Gly Phe Leu Asn Phe Leu Ile Trp Ala Ala Asn
    210                 215                 220

Val Trp Phe Val Phe Lys Glu Thr Thr Leu Ser Asn Lys Pro Ala Ser
225                 230                 235                 240

Lys Glu Glu Ser Ala Glu Arg Gly Glu Val Glu Asp His Gln
                245                 250

<210> SEQ ID NO 8
<211> LENGTH: 268
<212> TYPE: PRT
<213> ORGANISM: Gallus gallus
<220> FEATURE:
<221> NAME/KEY: MISC_FEATURE
<222> LOCATION: (1)..(268)
<223> OTHER INFORMATION: Chicken MG29

<400> SEQUENCE: 8

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Ala
            20                  25                  30

Asn Lys Ser Glu Ser Asp Leu Asn Ile Asp Ile Ala Phe Ala Tyr Pro
        35                  40                  45

Phe Arg Leu His Gln Val Asn Phe Asp Ala Pro Thr Cys Glu Gly Lys
    50                  55                  60

Arg Arg Glu Thr Leu Ser Leu Ile Gly Asp Phe Ser Ser Ser Ala Glu
65                  70                  75                  80

Phe Phe Val Thr Ile Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
        115                 120                 125

Leu Val Gly Ser Ser Ala Trp Ala Lys Gly Leu Ser Asp Val Lys Ile
    130                 135                 140

Ala Thr Asp Pro Asp Glu Val Leu Leu Leu Met Ser Ala Cys Lys Gln
145                 150                 155                 160

Gln Ser Asn Lys Cys Leu Pro Val Arg Ser Pro Val Met Ser Ser Leu
                165                 170                 175

Asn Thr Ser Val Val Phe Gly Phe Leu Asn Phe Ile Leu Trp Ala Gly
            180                 185                 190
```

Asn Ile Trp Phe Val Phe Lys Glu Thr Gly Trp His Ser Ser Gly Gln
            195                 200                 205

Arg His Ala Ala Asp Thr Met Glu Lys Gln Ser Ser Gly Tyr Asn Gln
            210                 215                 220

Gly Gly Tyr Asn Gln Asp Ser Tyr Gly Pro Ala Gly Gly Tyr Asn Gln
225                 230                 235                 240

Pro Gly Ser Tyr Gly Gln Val Gly Asp Tyr Gly Gln Pro Gln Ser Tyr
            245                 250                 255

Gly Gln Ser Gly Pro Thr Ser Phe Ala Asn Gln Ile
            260                 265

<210> SEQ ID NO 9
<211> LENGTH: 265
<212> TYPE: PRT
<213> ORGANISM: Homo sapiens
<220> FEATURE:
<221> NAME/KEY: MISC_FEATURE
<222> LOCATION: (1)..(265)
<223> OTHER INFORMATION: Human Synaptoporin

<400> SEQUENCE: 9

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
            35                  40                  45

Phe Arg Leu His Gln Val Thr Phe Glu Val Pro Thr Cys Glu Gly Lys
50                  55                  60

Glu Arg Gln Lys Leu Ala Leu Ile Gly Asp Ser Ser Ser Ser Ala Glu
65                  70                  75                  80

Phe Phe Val Thr Val Ala Val Phe Ala Phe Leu Tyr Ser Leu Ala Ala
            85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Ile His Ser Pro Val Met Ser Ser Leu
            165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
            195                 200                 205

Arg Tyr Leu Ser Asp Pro Met Glu Lys His Ser Ser Tyr Asn Gln
            210                 215                 220

Gly Gly Tyr Asn Gln Asp Ser Tyr Gly Ser Ser Gly Tyr Ser Gln
225                 230                 235                 240

Gln Ala Ser Leu Gly Pro Thr Ser Asp Glu Phe Gly Gln Gln Pro Thr
            245                 250                 255

Gly Pro Thr Ser Phe Thr Asn Gln Ile
            260                 265

```
<210> SEQ ID NO 10
<211> LENGTH: 276
<212> TYPE: PRT
<213> ORGANISM: Homo sapiens
<220> FEATURE:
<221> NAME/KEY: MISC_FEATURE
<222> LOCATION: (1)..(276)
<223> OTHER INFORMATION: Human highly similar to Synaptoporin

<400> SEQUENCE: 10

Met Cys Met Val Ile Phe Ala Pro His Asn Glu Glu Cys Lys Ser His
1               5                   10                  15

Phe His Leu Leu Phe Ala Ile Phe Ala Phe Ala Thr Cys Gly Gly Tyr
            20                  25                  30

Ser Gly Gly Leu Arg Leu Ser Val Asp Cys Val Asn Lys Thr Glu Ser
        35                  40                  45

Asn Leu Ser Ile Asp Ile Ala Phe Ala Tyr Pro Phe Arg Leu His Gln
    50                  55                  60

Val Thr Phe Glu Val Pro Thr Cys Glu Gly Lys Glu Arg Gln Lys Leu
65                  70                  75                  80

Ala Leu Ile Gly Asp Ser Ser Ser Ala Glu Phe Phe Val Thr Val
                85                  90                  95

Ala Val Phe Ala Phe Leu Tyr Ser Leu Ala Ala Thr Val Val Tyr Ile
            100                 105                 110

Phe Phe Gln Asn Lys Tyr Arg Glu Asn Asn Arg Gly Pro Leu Ile Asp
        115                 120                 125

Phe Ile Val Thr Val Val Phe Ser Phe Leu Trp Leu Val Gly Ser Ser
    130                 135                 140

Ala Trp Ala Lys Gly Leu Ser Asp Val Lys Val Ala Thr Asp Pro Lys
145                 150                 155                 160

Glu Val Leu Leu Leu Met Ser Ala Cys Lys Gln Pro Ser Asn Lys Cys
                165                 170                 175

Met Ala Ile His Ser Pro Val Met Ser Ser Leu Asn Thr Ser Val Val
            180                 185                 190

Phe Gly Phe Leu Asn Phe Ile Leu Trp Ala Gly Asn Ile Trp Phe Val
        195                 200                 205

Phe Lys Glu Thr Gly Trp His Ser Ser Gly Gln Arg Tyr Leu Ser Asp
    210                 215                 220

Pro Met Glu Lys His Ser Ser Tyr Asn Gln Gly Tyr Asn Gln
225                 230                 235                 240

Asp Ser Tyr Gly Ser Ser Ser Gly Tyr Ser Gln Gln Ala Ser Leu Gly
                245                 250                 255

Pro Thr Ser Asp Glu Phe Gly Gln Gln Pro Thr Gly Pro Thr Ser Phe
            260                 265                 270

Thr Asn Gln Ile
        275

<210> SEQ ID NO 11
<211> LENGTH: 265
<212> TYPE: PRT
<213> ORGANISM: Mus musculus
<220> FEATURE:
<221> NAME/KEY: MISC_FEATURE
<222> LOCATION: (1)..(265)
<223> OTHER INFORMATION: Mouse Synaptoporin

<400> SEQUENCE: 11

Met Cys Met Val Ile Phe Ala Pro Leu Phe Ala Met Phe Ala Phe Ala
1               5                   10                  15
```

```
Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
        35                  40                  45

Phe Arg Leu Gln Gln Val Thr Phe Glu Val Pro Thr Cys Glu Gly Lys
 50                  55                  60

Glu Gln Gln Lys Leu Ala Leu Val Gly Asp Ser Ser Ser Ala Glu
 65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
                100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Val His Ser Pro Val Met Ser Ser Leu
                165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
            195                 200                 205

Arg Tyr Leu Ser Asp Pro Met Glu Lys His Ser Ser Tyr Asn Gln
            210                 215                 220

Gly Arg Tyr Asn Gln Glu Ser Tyr Gly Ser Ser Gly Gly Tyr Ser Gln
225                 230                 235                 240

Gln Ala Asn Leu Gly Pro Thr Ser Asp Glu Phe Gly Gln Gln Pro Ser
                245                 250                 255

Gly Pro Thr Ser Phe Asn Asn Gln Ile
            260                 265

<210> SEQ ID NO 12
<211> LENGTH: 255
<212> TYPE: PRT
<213> ORGANISM: Mus musculus
<220> FEATURE:
<221> NAME/KEY: MISC_FEATURE
<222> LOCATION: (1)..(255)

<400> SEQUENCE: 12

Phe Asp Arg Ser Leu Asn Arg Thr Arg Gly Phe Ser Ala Ala Gly Gly
1               5                   10                  15

Ala Ala Arg Arg Thr Glu Pro Pro Arg Ala Arg Ala Ala Pro Pro
                20                  25                  30

Arg Pro Ser Pro Pro Ala Trp Ser Pro Ala Cys Pro Arg Pro Arg Ala
            35                  40                  45

Arg Arg Pro Gln Arg Pro Arg Ala Pro Arg Ser Leu Pro Ala Arg Glu
 50                  55                  60

Ser Asn Pro Cys Thr Ala Pro Arg Arg Ala Ser Met Ser Ser Thr Glu
65                  70                  75                  80

Ser Pro Gly Arg Thr Ser Asp Lys Ser Pro Arg Gln Gln Val Asp Arg
                85                  90                  95

Leu Leu Leu Gly Leu Arg Trp Gln Arg Leu Glu Glu Pro Leu Gly Phe
                100                 105                 110
```

```
Ile Lys Val Leu Gln Trp Leu Phe Ala Ile Phe Ala Phe Gly Ser Cys
        115                 120                 125

Gly Ser Tyr Ser Gly Glu Thr Gly Ala Leu Val Leu Cys Asn Asn Glu
        130                 135                 140

Ala Lys Asp Val Ser Ser Ile Ile Val Leu Phe Gly Tyr Pro Phe Arg
145                 150                 155                 160

Leu Tyr Gln Val Gln Tyr Glu Met Pro Leu Cys Asp Gln Asp Ser Thr
                165                 170                 175

Ser Lys Thr Met Asn Leu Met Gly Asp Phe Ser Ala Pro Ala Glu Phe
                180                 185                 190

Phe Val Thr Leu Gly Ile Phe Ser Phe Phe Tyr Thr Met Ala Ala Leu
            195                 200                 205

Val Ile Tyr Leu Arg Phe His Lys Leu Tyr Thr Glu Asn Lys Arg Phe
        210                 215                 220

Pro Leu Val Val Ser Glu Pro Trp Pro Arg Gly Ile Gly Pro Ile Asn
225                 230                 235                 240

Val Arg Asp Gly Gly Ala Ile Lys Ser Asn Ser Phe Pro Glu Ser
                245                 250                 255

<210> SEQ ID NO 13
<211> LENGTH: 285
<212> TYPE: PRT
<213> ORGANISM: Mus musculus
<220> FEATURE:
<221> NAME/KEY: MISC_FEATURE
<222> LOCATION: (1)..(285)
<223> OTHER INFORMATION: Mouse Synaptoporin2

<400> SEQUENCE: 13

Met Asp Pro Val Ser Gln Val Ala Ser Ala Gly Thr Phe Arg Ala Leu
1               5                   10                  15

Lys Glu Pro Leu Ala Phe Leu Arg Ala Leu Glu Leu Leu Phe Ala Met
            20                  25                  30

Phe Ala Phe Ala Thr Cys Gly Gly Tyr Ser Gly Gly Leu Arg Leu Ser
        35                  40                  45

Val Asp Cys Val Asn Lys Thr Glu Ser Asn Leu Ser Ile Asp Ile Ala
50                  55                  60

Phe Ala Tyr Pro Phe Arg Leu Gln Gln Val Thr Phe Glu Val Pro Thr
65                  70                  75                  80

Cys Glu Gly Lys Glu Gln Gln Lys Leu Ala Leu Val Gly Asp Ser Ser
                85                  90                  95

Ser Ser Ala Glu Phe Phe Val Thr Ala Val Phe Ala Phe Leu Tyr
            100                 105                 110

Ser Leu Ala Ala Thr Val Val Tyr Ile Phe Phe Gln Asn Lys Tyr Arg
        115                 120                 125

Glu Asn Asn Arg Gly Pro Leu Ile Asp Phe Ile Val Thr Val Val Phe
        130                 135                 140

Ser Phe Leu Trp Leu Val Gly Ser Ser Ala Trp Ala Lys Gly Leu Ser
145                 150                 155                 160

Asp Val Lys Val Ala Thr Asp Pro Lys Glu Val Leu Leu Leu Met Ser
                165                 170                 175

Ala Cys Lys Gln Pro Ser Asn Lys Cys Met Ala Val His Ser Pro Val
                180                 185                 190

Met Ser Ser Leu Asn Thr Ser Val Phe Gly Phe Leu Asn Phe Ile
            195                 200                 205

Leu Trp Ala Gly Asn Ile Trp Phe Val Phe Lys Glu Thr Gly Trp His
        210                 215                 220
```

-continued

```
Ser Ser Gly Gln Arg Tyr Leu Ser Asp Pro Met Glu Lys His Ser Ser
225                 230                 235                 240

Ser Tyr Asn Gln Gly Arg Tyr Asn Gln Glu Ser Tyr Gly Ser Ser Gly
                245                 250                 255

Gly Tyr Ser Gln Gln Ala Asn Leu Gly Pro Thr Ser Asp Glu Phe Gly
            260                 265                 270

Gln Gln Pro Ser Gly Pro Thr Ser Phe Asn Asn Gln Ile
        275                 280                 285

<210> SEQ ID NO 14
<211> LENGTH: 390
<212> TYPE: PRT
<213> ORGANISM: Mus musculus
<220> FEATURE:
<221> NAME/KEY: MISC_FEATURE
<222> LOCATION: (1)..(390)

<400> SEQUENCE: 14

Met Ser Ser Thr Glu Ser Pro Gly Arg Thr Ser Asp Lys Ser Pro Arg
1               5                   10                  15

Gln Gln Val Asp Arg Leu Leu Leu Gly Leu Arg Trp Gln Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Leu Val
    50                  55                  60

Leu Cys Asn Asn Glu Ala Lys Asp Val Ser Ser Ile Ile Val Leu Phe
65                  70                  75                  80

Gly Tyr Pro Phe Arg Leu Tyr Gln Val Gln Tyr Glu Met Pro Leu Cys
                85                  90                  95

Asp Gln Asp Ser Thr Ser Lys Thr Met Asn Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Lys Leu Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Leu Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                245                 250                 255

Glu Gln Gly Ala Val Glu Lys Gln Leu Ser Ser Leu His Leu Pro Thr
            260                 265                 270

Pro Gln Leu Asp Gly Thr Leu Ser Ala Pro Ala Ser Thr Gly Pro
        275                 280                 285

Pro Pro Leu Pro Leu Pro Pro Ala Pro Pro Leu Pro Pro Pro Pro Thr
    290                 295                 300
```

```
Pro Arg Pro Pro Ser Phe Trp Thr Leu Arg Phe Glu Arg Met Asp Gly
305                 310                 315                 320

Trp Ala Ser Ala Val Gly Asn Leu Gly Arg Pro Pro Leu Ala Ser Tyr
            325                 330                 335

Pro Ser Ser Cys Trp Gly Ser Lys Arg Gln Asp Leu Ser Ala Ser Cys
            340                 345                 350

Leu Leu Pro Gly Ala Glu Ala Ser Tyr Leu Gly Lys Leu Thr Gly Asn
        355                 360                 365

Leu Ala Ala Glu Phe Cys Val Glu Gly Pro Pro Val Ile Leu Trp His
    370                 375                 380

Pro Ser Ile Thr Gly Ile
385                 390

<210> SEQ ID NO 15
<211> LENGTH: 341
<212> TYPE: PRT
<213> ORGANISM: Mus musculus
<220> FEATURE:
<221> NAME/KEY: MISC_FEATURE
<222> LOCATION: (1)..(341)

<400> SEQUENCE: 15

Arg Leu Phe Asp Arg Ser Leu Asn Arg Thr Arg Gly Phe Ser Ala Ala
1               5                   10                  15

Gly Gly Ala Ala Arg Arg Thr Glu Pro Pro Arg Ala Arg Ala Ala Ala
            20                  25                  30

Pro Pro Arg Pro Ser Pro Ala Trp Ser Pro Ala Cys Pro Arg Pro
        35                  40                  45

Arg Ala Arg Arg Pro Gln Arg Pro Arg Ala Pro Arg Ser Leu Pro Ala
50                  55                  60

Arg Glu Ser Asn Pro Cys Thr Ala Pro Arg Ala Ser Met Ser Ser
65                  70                  75                  80

Thr Glu Ser Pro Gly Arg Thr Ser Asp Lys Ser Pro Arg Gln Gln Val
                85                  90                  95

Asp Arg Leu Leu Leu Gly Leu Arg Trp Gln Arg Leu Glu Glu Pro Leu
            100                 105                 110

Gly Phe Ile Lys Val Leu Gln Trp Leu Phe Ala Ile Phe Ala Phe Gly
        115                 120                 125

Ser Cys Gly Ser Tyr Ser Gly Glu Thr Gly Ala Leu Val Leu Cys Asn
130                 135                 140

Asn Glu Ala Lys Asp Val Ser Ser Ile Ile Val Leu Phe Gly Tyr Pro
145                 150                 155                 160

Phe Arg Leu Tyr Gln Val Gln Tyr Glu Met Pro Leu Cys Asp Gln Asp
                165                 170                 175

Ser Thr Ser Lys Thr Met Asn Leu Met Gly Asp Phe Ser Ala Pro Ala
            180                 185                 190

Glu Phe Phe Val Thr Leu Gly Ile Phe Ser Phe Phe Tyr Thr Met Ala
        195                 200                 205

Ala Leu Val Ile Tyr Leu Arg Phe His Lys Leu Tyr Thr Glu Asn Lys
210                 215                 220

Arg Phe Pro Leu Val Asp Phe Cys Val Thr Val Ser Phe Thr Phe Phe
225                 230                 235                 240

Trp Leu Val Ala Ala Ala Trp Gly Lys Gly Leu Thr Asp Val Lys
                245                 250                 255

Gly Ala Thr Arg Pro Ser Ser Leu Thr Ala Ala Met Ser Val Cys His
            260                 265                 270
```

```
Gly Glu Glu Ala Val Cys Ser Ala Gly Ala Thr Pro Ser Met Gly Leu
            275                 280                 285

Ala Asn Leu Ser Val Leu Phe Gly Phe Ile Asn Phe Leu Trp Ala
            290                 295                 300

Gly Asn Cys Trp Phe Val Phe Lys Glu Thr Pro Trp His Gly Gln Gly
305                 310                 315                 320

Gln Asp Gln Gly Gln Gly Pro Ser Gln Glu Ser Ala Ala Glu Gln Gly
            325                 330                 335

Ala Val Glu Lys Gln
            340

<210> SEQ ID NO 16
<211> LENGTH: 272
<212> TYPE: PRT
<213> ORGANISM: Homo sapiens
<220> FEATURE:
<221> NAME/KEY: MISC_FEATURE
<222> LOCATION: (1)..(272)

<400> SEQUENCE: 16

Met Ser Ser Thr Glu Ser Ala Gly Arg Thr Ala Asp Lys Ser Pro Arg
1               5                   10                  15

Gln Gln Val Asp Arg Leu Leu Val Gly Leu Arg Trp Arg Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Met Val
    50                  55                  60

Arg Cys Asn Asn Glu Ala Lys Asp Val Ser Ser Ile Ile Val Ala Phe
65                  70                  75                  80

Gly Tyr Pro Phe Arg Leu His Arg Ile Gln Tyr Glu Met Pro Leu Cys
                85                  90                  95

Asp Glu Glu Ser Ser Ser Lys Thr Met His Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Asn Leu Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Met Ser
            180                 185                 190

Val Cys His Gly Glu Glu Ala Val Cys Ser Ala Gly Ala Thr Pro Ser
            195                 200                 205

Met Gly Leu Ala Asn Ile Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Gly Gln Asp Gln Asp Gln Asp Gln Asp Gln Gly Gln
            245                 250                 255

Gly Pro Ser Gln Glu Ser Ala Ala Glu Gln Gly Ala Val Glu Lys Gln
            260                 265                 270

<210> SEQ ID NO 17
```

```
<211> LENGTH: 143
<212> TYPE: PRT
<213> ORGANISM: Homo sapiens
<220> FEATURE:
<221> NAME/KEY: MISC_FEATURE
<222> LOCATION: (1)..(143)

<400> SEQUENCE: 17

Met Ala Ala Leu Val Ile Tyr Leu Arg Phe His Asn Leu Tyr Thr Glu
1               5                   10                  15

Asn Lys Arg Phe Pro Leu Val Asp Phe Cys Val Thr Val Ser Phe Thr
            20                  25                  30

Phe Phe Trp Leu Val Ala Ala Ala Trp Gly Lys Gly Leu Thr Asp
        35                  40                  45

Val Lys Gly Ala Thr Arg Pro Ser Ser Leu Thr Ala Ala Met Ser Val
50                  55                  60

Cys His Gly Glu Glu Ala Val Cys Ser Ala Gly Ala Thr Pro Ser Met
65                  70                  75                  80

Gly Leu Ala Asn Ile Ser Val Leu Phe Gly Phe Ile Asn Phe Phe Leu
                85                  90                  95

Trp Ala Gly Asn Cys Trp Phe Val Phe Lys Glu Thr Pro Trp His Gly
            100                 105                 110

Gln Gly Gln Gly Gln Asp Gln Asp Gln Asp Gln Gly Gln Gly
        115                 120                 125

Pro Ser Gln Glu Ser Ala Ala Glu Gln Gly Ala Val Glu Lys Gln
    130                 135                 140

<210> SEQ ID NO 18
<211> LENGTH: 265
<212> TYPE: PRT
<213> ORGANISM: Bos taurus
<220> FEATURE:
<221> NAME/KEY: MISC_FEATURE
<222> LOCATION: (1)..(265)
<223> OTHER INFORMATION: Bovine Synaptoporin

<400> SEQUENCE: 18

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Ala
            20                  25                  30

Asn Lys Thr Glu Ser Asp Leu Ser Ile Asp Val Ala Phe Ala Tyr Pro
        35                  40                  45

Phe Arg Leu His Gln Val Thr Phe Glu Val Pro Thr Cys Glu Gly Lys
50                  55                  60

Glu Arg Gln Lys Val Ser Leu Ile Gly Asp Ser Ser Ser Ala Glu
65                  70                  75                  80

Phe Phe Val Thr Val Ala Val Phe Ala Phe Leu Tyr Ser Leu Ala Ala
                85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
        115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Thr Ala Val His Ser Pro Val Met Ser Ser Leu
                165                 170                 175
```

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Ser Gln
            195                 200                 205

Arg Tyr Leu Ser Asp Pro Met Glu Lys His Ser Ser Ser Tyr Asn Arg
            210                 215                 220

Gly Gly Tyr Asn Gln Asp Ser Tyr Gly Ser Ser Ser Gly Tyr Asn Gln
225                 230                 235                 240

Gln Ala Ser Leu Gly Pro Ser Ser Asp Glu Phe Gly Gln Gln Ser Ala
                245                 250                 255

Ala Pro Ala Ser Phe Thr Asn Gln Met
            260                 265

<210> SEQ ID NO 19
<211> LENGTH: 265
<212> TYPE: PRT
<213> ORGANISM: Rattus norvegicus
<220> FEATURE:
<221> NAME/KEY: MISC_FEATURE
<222> LOCATION: (1)..(265)
<223> OTHER INFORMATION: Rat Synaptoporin

<400> SEQUENCE: 19

Met Cys Met Val Ile Phe Ala Pro Leu Phe Ala Ile Phe Ala Phe Ala
1               5                   10                  15

Thr Cys Gly Gly Tyr Ser Gly Gly Leu Arg Leu Ser Val Asp Cys Val
            20                  25                  30

Asn Lys Thr Glu Ser Asn Leu Ser Ile Asp Ile Ala Phe Ala Tyr Pro
        35                  40                  45

Phe Arg Leu His Gln Val Thr Phe Glu Val Pro Thr Cys Glu Gly Lys
    50                  55                  60

Glu Arg Gln Lys Leu Ala Leu Val Gly Asp Ser Ser Ser Ser Ala Glu
65                  70                  75                  80

Phe Phe Val Thr Val Ala Val Phe Ala Phe Leu Tyr Ser Leu Ala Ala
            85                  90                  95

Thr Val Val Tyr Ile Phe Phe Gln Asn Lys Tyr Arg Glu Asn Asn Arg
            100                 105                 110

Gly Pro Leu Ile Asp Phe Ile Val Thr Val Val Phe Ser Phe Leu Trp
            115                 120                 125

Leu Val Gly Ser Ser Ala Trp Ala Lys Gly Leu Ser Asp Val Lys Val
130                 135                 140

Ala Thr Asp Pro Lys Glu Val Leu Leu Leu Met Ser Ala Cys Lys Gln
145                 150                 155                 160

Pro Ser Asn Lys Cys Met Ala Val His Ser Pro Val Met Ser Ser Leu
            165                 170                 175

Asn Thr Ser Val Val Phe Gly Phe Leu Asn Phe Ile Leu Trp Ala Gly
            180                 185                 190

Asn Ile Trp Phe Val Phe Lys Glu Thr Gly Trp His Ser Ser Gly Gln
            195                 200                 205

Arg Tyr Leu Ser Asp Pro Met Glu Lys His Ser Ser Ser Tyr Asn Gln
            210                 215                 220

Gly Gly Tyr Asn Gln Asp Ser Tyr Gly Ser Ser Gly Tyr Ser Gln
225                 230                 235                 240

Gln Ala Ser Leu Gly Pro Thr Ser Asp Glu Phe Gly Gln Gln Pro Ser
                245                 250                 255

Gly Pro Thr Ser Phe Asn Asn Gln Ile

<210> SEQ ID NO 20
<211> LENGTH: 1666
<212> TYPE: DNA
<213> ORGANISM: Xenopus tropicalis
<220> FEATURE:
<221> NAME/KEY: misc_feature
<222> LOCATION: (1)..(1666)
<223> OTHER INFORMATION: X. tropicalis MG29 (NM_001006110)

<400> SEQUENCE: 20

| | |
|---|---|
| gtaacttaat taagttgcgg aaatatcagt aatcaaactg atacagattt ttagtcatat | 60 |
| ttacagaata tccagaaaca atattgtgtc agtggtacaa atttacagaa agcctgtctg | 120 |
| cataaaacaa atactatata catttaatga actagattta tagattgtaa agctgtaaga | 180 |
| gagaggaaac ggtaggtaca gaaaaaaagt aacaggttta cagaagctgg tcatcaggag | 240 |
| gaacagacac actcccttca cttggatact tgagcccttc tgttcagacg actgagttcc | 300 |
| agccacttac ccttggacac ccttaaataa ggaccatgtc aacagcagtt tcctcctcaa | 360 |
| cgatggacag agagggggc cttgcaggac ttggcaagaa gaacccactg gctggtctac | 420 |
| gctggaggag gttagaggag ccattgggat tcattaagtt actggaatgg ctgtttgcta | 480 |
| tatttgcctt tggatgttgt gggtcataca gtggagagac agcagcaact gtcatgtgca | 540 |
| agacagagac ggactcagac acagaaataa agctcatctc agttcccttt gcatacccat | 600 |
| tcaggctgta tcgccagcgc tatgagatgc agcttgtga agatatagaa aggcgtattc | 660 |
| tccacttgac aggggatttc tcagcccccg cagagttctt tgttaccatg ggagtctttg | 720 |
| cattcctata ctctatgttt gcactggtcg tctatctgcg cttccacgaa gaatacacca | 780 |
| aaatccgccg agtgccaatt gtggatttgt gcgtgactgg tgcctttgcc ttttttgtggc | 840 |
| ttgtggcagc ttcagcttgg gggaaaggac tgatggatgt gaaggtggcc actcaacctt | 900 |
| ccaaccttgt ctcttcaatg cctctgtgcc aaatggaaaa agcaacatgc aatgctggct | 960 |
| ctcaaccata ttttgcactt gctaacattt ctgtgctctt tggctttctg aatttcctta | 1020 |
| tctgggctgc caatgtatgg tttgtgttta aagagaccac attgagtaat aaacctgcct | 1080 |
| ccaaagagga atctgcagag cgtggagagg ttgaagacca ccagtgatac ctggcaaaca | 1140 |
| aattcctggg tttccaacat caactcttcc tcctgaaatt ctagaaatga gccctctcct | 1200 |
| ttaccaggct tcaaattatc attatgatct tttattttt gccctaacac tgtccactct | 1260 |
| ttcagtgaat atgagtaata ttccaaaaac ataccagtat acagaggtgc ttattaaaac | 1320 |
| tgcttaatgt agggtttatt tgaatcatat ttaatacagc ccagcatata gcgtattta | 1380 |
| tgtacgagta acccaatttg tacctaacca tagcacaaa taaaaaagca gggttgagct | 1440 |
| ttttataatg ctgtttataa cagtatttat ttttaaatat gtgccctact gtataggaca | 1500 |
| gtactgatcc ataatatcct ttcttttgga attgcctcct gtcctgtaac cttaataacc | 1560 |
| tttctcacct gtccacagta agatgaccca tctatctcca gtgtctctgg tgctatttat | 1620 |
| taaataaaaa taaatactct acaaaaaaaa aaaaaaaaa aaaaaa | 1666 |

<210> SEQ ID NO 21
<211> LENGTH: 3779
<212> TYPE: DNA
<213> ORGANISM: Homo sapiens
<220> FEATURE:
<221> NAME/KEY: misc_feature
<222> LOCATION: (1)..(3779)
<223> OTHER INFORMATION: Human MG29 (NM_001040709)

<400> SEQUENCE: 21

```
aaggtgcccg gcgagcggag aaagggagca gaggggggcgg gaggagggtt cgggagcgca    60
cgccacgtga cccggcggcc aagttcgctg cgagtttgac agaagtttga atccgagtcg   120
ggggctttct gctgccggcg gggcaccgcg gcggccgcag cctctgagag cacgaacagc   180
agcgcccccg cgtcccagcc agccagccag ccagactgga ctccggccca ccgacggccg   240
ctcgcgctcc ggccccgctc gcctgctctg ccccggacct gcagctcccc gctccccgc    300
cgtgtccgcc gcctcccggc cagagagcca agccaccacg ccgcgcccag cgctcgccgc   360
gccagcatgt cctcgaccga gagcgccggc cgcacggcgg acaagtcgcc gcgccagcag   420
gtggaccgcc tactcgtggg gctgcgctgg cggcggctgg aggagccgct gggcttcatc   480
aaagttctcc agtggctctt tgctattttc gccttcgggt cctgtggctc ctacagcggg   540
gagacaggag caatggttcg ctgcaacaac gaagccaagg acgtgagctc catcatcgtt   600
gcatttggct atcccttcag gttgcaccgg atccaatatg agatgcccct ctgcgatgaa   660
gagtccagct ccaagaccat gcacctcatg ggggacttct ctgcacccgc cgagttcttc   720
gtgacccttg gcatcttttc cttcttctat accatggctg ccctagttat ctacctgcgc   780
ttccacaacc tctacacaga gaacaaacgc ttcccgctgg tggacttctg tgtgactgtc   840
tccttcacct tcttctggct ggtagctgca gctgcctggg gcaagggcct gaccgatgtc   900
aagggggcca cacgaccatc cagcttgaca gcagccatgt cagtgtgcca tggagaggaa   960
gcagtgtgca gtgccgggc cacgccctct atgggcctgg ccaacatctc cgtgctcttt  1020
ggctttatca acttcttcct gtgggccggg aactgttggt ttgtgttcaa ggagaccccg  1080
tggcatggac agggccaggg ccaggaccag gaccaggacc aggaccaggg ccagggtccc  1140
agccaggaga gtgcagctga gcaggagca gtggagaagc agtaagcagc cccccacctg   1200
gctattcccg aactggacag cacctcttca accacctccg gcttccagga cctttctctt  1260
cctcctcctc caattcccct cccccatcat tctggtcttt gagctttgag acgatgggca  1320
ggcatcagct gttggaaacc tgggcagccc tctcagtggc ttcctatcct ccttcttgct  1380
ggagccatga atggcaggag ctcagtgctt cttgtgcagt gcctggaccc aggtatctta  1440
cttggggtct tacttgtacc cttacagtct ctgagaacca gcctctgctg caggtgaggg  1500
ttggggggcag gaaaccagtg ctctgagact ggttcctagc agccaccttt ctgtcaacct  1560
gtccggcttc aacaatatta gggggaaggg aaatcagcta gtagccttcc cctctggtcc  1620
cttgtgtgga ggccccaata gtggtttggc gaccccctcct cagtggctgt catctagtcc  1680
ctgcgtctga tctccagtca tcccatgact cagtgtgcct tccactgtct tctctggcct  1740
ctgcctgccc acagaatcca ccatgtgtga accagagagg tccaccagcc tagaaaacag  1800
cccttcagag ggtcctgatg aggccttcct ggactcagct gggagcaaga taaattgcaa  1860
ctgagttgca gcttcaagaa agtaaagcca gtaagcttgc tggcagaatc aatttcttct  1920
atccctcaa tcctcccacc caccaggctg gggcactttc caccaacact ctaaactcta  1980
ctttagaaaac gccctatctt cctccctgtc ctccttcttg gtctcacact tgggactcaa  2040
aaatgtggag tcaggacctg cctcctaatc cccttacttc tctgtccatc tcccttcccc  2100
agcatcgtgc atctgaggca tttgagatcc tttttgaagt ctgtccaggc cttccttta   2160
ttcctgtggg gccagacagg ggcttaggaa gggccaaagg accatcatga ggctaagttg  2220
ccccagagcc ccaggatgga tgggcccatt ttttccttat tccctgctca gttttttccc  2280
ctgctccttc tctagtcctt cttttcatatt tctccttctc atcttgaaaa caggatgttc  2340
```

```
cctcttccct tgctgtccca tttctcccct gtgtccttat ttctcccagt ctctatcccc    2400
tctcaagtcc agggcaggcc gatgctattg gtgcttcttc actttgggac ccagttccat    2460
atttgtcttt agtgtatatc ctcttcctga tacctccttc agtccctctc tgggccccaa    2520
ggctgagaat cagtgttaac tgggtaagga tcatttgctt cctacccagc tcaatctgcc    2580
ctggccatag ggcttcccag ggaaggaaga agagggaaga atccgaccac tttccaatcc    2640
agtgccaatt gcccactaa gcatcctaaa ggtgaatgtg ccctgtgcca atctctcctc     2700
aggactgagt caaccccctt caacctcctc acctctctaa acaccatcca tagtaacatg    2760
tgcattactg gggtacctag gagtcaggac ttttgacttc aggccagtca tttcctcccg    2820
atggggaaag ggtgagattt acatccccaa atgcttgagt ccctcagtga aagaattagt    2880
ttttgtttgt ttgtttaaga ttttggggaa gagatttgag gaggaaagaa aggagatggg    2940
gtgagagggt ttttaagtct gaaactctct gtcatgagct gtccccatgg ttactcaagg    3000
acaagggggg acagttttgc ctacagctcc agagacacag agaacaaagg ggtgaccttc    3060 attttcttc aagccggcct ctgtgggggt ctgtgagcag cttctactgg atctttgttt     3120
ggattctgtg tctgtattta taatttattt gaaatgtgct gggtagtgtt ctcatttggg    3180
ggctgaagtt agcaactggg ccttcagcta gggaaagcag ttgcgggcag ggggtggggg    3240
gagattatat tcactcctgc caaggactcc cagcccagga ctctctttag agcaaggaag    3300
cctcgttctc tttcttctca agaggctctc ttgttctcca tcaggagagc cttgatttag    3360
gctacggcct cactctctat ggccacccta agaggaaagg ctacttcacc tcattacctc    3420
cagagggctg ggcagggcca agtgcctcat aggactcatg ttctctccaa ccagggctgg    3480
catcactgct ttgcaaagtg gggcctgagg tagaagaagg tgtctggttt ctccagctgc    3540
tgtaggaggc taatgggcag ggtacttgcc ctttgtccca ctagactcta acccagcacc    3600
agggtgccca cctaggacct ttcctggaca tgagtttcct tcactatcat agtcatgagc    3660
ctcctacttc tgggattgca gatcaggggt gggggagaa tgttgcatgt tgttttctgg     3720
tgcttgttat tatatatttg aataaacagt gctgcaagta cttgccatga aggatctga    3779
```

<210> SEQ ID NO 22
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: human variant sypl2 (BC113102)

<400> SEQUENCE: 22

```
ggctaagtgg cttttgggta tcccttcagg ttgcaccgga tccaatatga gatgcccctc      60
tgcgatgaag agtccagctc caagaccatg cacctcatgg gggacttctc tgcacccgcc     120
gagttcttcg tgacccttgg catctttttcc ttcttctata ccatggctgc cctagttatc    180
tacctgcgct tccacaacct ctacacagag aacaaacgct tcccgctggt ggacttctgt    240
gtgactgtct ccttcacctt cttctggctg gtagctgcag ctgcctgggg caagggcctg    300
accgatgtca agggggccac acgaccatcc agcttgacag cagccatgtc agtgtgccat    360
ggagaggaag cagtgtgcag tgccggggcc acgccctcta tgggcctggc caacatctcc    420
gtggtgagac ctgtggccac tgcaggaagc agcaccagcc tgctgcccca ggcctgtccc    480
agctagcagg tcctgaaagg aaagagaggg tgtcccagag ctggtgtccc ctgcacctgg    540
agctggtgcc ctcactgcgc ttcatgctgg ctgctggctc ctggctgacc ctgagaggac    600
```

-continued

| | |
|---|---|
| attttgggat gagggggaacc caaaagccac ttagcc | 636 |

<210> SEQ ID NO 23
<211> LENGTH: 3403
<212> TYPE: DNA
<213> ORGANISM: Rattus norvegicus
<220> FEATURE:
<221> NAME/KEY: misc_feature
<222> LOCATION: (1)..(3403)
<223> OTHER INFORMATION: Rat MG29 (NM_001108563)

<400> SEQUENCE: 23

| | |
|---|---|
| gcggggcagc gcggcggaca gagcctccga gagcgcgagc agcagcgccc ccacgaccca | 60 |
| gcccgccagc ctggagcccg gcctgcccac ggccgcgagc ccgccgcccc cagcgccccc | 120 |
| gcgcgccccg cagcctcccg gccagggagt cgaaccccg cactgcgccc cgacgcgcca | 180 |
| gcatgtcctc gacggagagc cccggccgca cctcggacaa gtctccgcgc cagcaggtgg | 240 |
| accgcctgct cctggggctg cgctggcagc gcctggagga gccgctgggc ttcatcaaag | 300 |
| ttctccagtg gctctttgct attttcgcct tcgggtcctg cggctcttac agcggggaga | 360 |
| cgggagcctt ggttcgctgc aacaacgacc ccaaggacgt gagctccatc attgttttgt | 420 |
| tcggctatcc cttcaggttg taccaggtcc agtatgagat gcctctctgt gatgaggaat | 480 |
| ccacatccaa aaccatgaac ctcatgggag acttctctgc ccccgccgag ttctttgtga | 540 |
| cccttggcat cttttccttc ttctatacaa tggctgccct ggtcatctac ctgcgcttcc | 600 |
| acaaagtcta cacggagaac aaacgcttcc cattggtgga tttctgtgtg accgtctctt | 660 |
| tcaccttctt ttggctggtt gctgccgctg cctggggcaa gggcttgact gatgtcaaag | 720 |
| gggccacacg gccatccagc ctgactgcag ccatgtctgt gtgccatgga gaggaggcag | 780 |
| tgtgcagtgc tggggccacg ccctctatgg ggctggctaa catctctgtg ctctttggct | 840 |
| ttatcaactt cttcctgtgg gctggaaaact gttggtttgt gttcaaagag accccatggc | 900 |
| acggacaagg ccaggaccag ggccagggcc cagccagga gagtgcagca gaacaggag | 960 |
| cggtggagaa gcagtaagca gccctcatct gcctactccc caactggaca tggacagcac | 1020 |
| cttctcatct cctccagctt ctacaggacc ttcttcctcc tcctcctccc ttaccccatc | 1080 |
| actctggact tgagatttg agagaatgga tgggtaggca tcagctgttg gtaacctggg | 1140 |
| cagaccccca ctggctatcc ctcatcctgc tggggcagcc aatggcagga tctccgtgct | 1200 |
| tcttgtccgc tgcctggagt tgggcatctt gctcgggcaa gtcagctggc aaccttgccc | 1260 |
| tgattcccgt gtgagggcc caccagtgac tttgtgacat ccctcggtag ctgtcatcta | 1320 |
| atctgtatcc tatctctagc cctcccagag ctcactgtgc tccccaatct cctctctggc | 1380 |
| ctctgtccat agctctcacc acgtgtgaag caggagacc cattaccta ccgaaggtcc | 1440 |
| ctctaggggt ccacgtgaga cccggaccca gtgggagagg atagagttgc ctattgcagc | 1500 |
| accaaggaag aaagtcagga aagttgctgg cagaatacgt tttctgtccc ctcagccctc | 1560 |
| cctctccctc agctggaaca cttttcagtag tgccctacac tccacttatt catgaaaccc | 1620 |
| cttacaccct tctccttctc agccttggtt ttgtctcaca cttcggaaac aagatggaat | 1680 |
| ggcttggaac atttcccctt catttttccca tccccaccac acctgtgggc ccttctccct | 1740 |
| tccccaacct tttggagatg aggcatttaa gatcttttca aaagcctgcc caggccttcc | 1800 |
| tttcattcct gtgggctttg ggagggcctg aaggaccacc ataaggctga tgtgcccagg | 1860 |
| aatcccagga catgaataca cgggcccagt tgtcccttac tgtctgttca ttttctcaag | 1920 |
| ccagctcctt ttctagttct ttcaaaacctg tccttcccat cttaacaaag agggttctct | 1980 |

```
ctcctcatct ctcacctcca cacggtagcc aggccccatc ccttccccag tcctgggcag    2040
cccgatgcta ttggtgcttc ttcacttcgg gacccagttc catatttgtc tttggtgtgt    2100
ctcctcttcc tgatacccc ttcatcccct ttttgtcccc aaggccttag ggtaccaact    2160
gggtaaatgc catccgcctc ctacctagat caaaaccct tgatctaccc tggcagggtt    2220
gctcagggaa agtgaagaag gaagaaacca gccatttccc aatatagtgg caacgggccc    2280
acctaaatcc caaagatgaa tgtaccttgt gccaacctgt ccttaagaca cgatcaaccc    2340
tctccagccc ccttgcctct ctcaatgcta cccacatcaa gatgtattac ttgggtgccc    2400
agggctcaga atccttaact ctgggccatt catttcttct ttgggttaca atttccccac    2460
ccaacagaga agtatgatat ttacagacat tacagatgct cccaagccct tcagtaaaag    2520
aatttggaat ttttgttttc tgtttcagat tttagaaaa agatttgaga aggggaaaat    2580
ttgatgagga tgagaatgtt cctaaatctg aaactctcta tcctaagttg tcctcatggt    2640
tacttaagga caaggggag agttttgcct acaactttag atatacaaag aacaaagggg    2700
tgaccatttt tcttcaagca agtccctgtg gggatctggg agcagcttct actcgaactg    2760
tgtttggatt ctgcgtccat atttataatt tatttgaact gtgatggata cagtgttctc    2820
atttagggcc taaggtagca actggcccat caactacttt agaaagggag ctgtccactc    2880
ccagtgagca ctcttactcc agagctctct ctagggttga gaaggctttt cttcagcaag    2940
agtctggcta tggccaaaag agccttaatt taggctatgg cctttctctc catggctgcc    3000
ctcagaggaa agaccagttc acctcattac ctccagggg ctgggcagcc tgcgtgccaa    3060
gggcagctct gtcctcataa gactcatgtc ctctccaacc agggctggca ccagtacttt    3120
gtctagtcag gcctggacta ggagaaggtg tctggttct ctagctatcg caggaggcca    3180
acaagcgggg aacttgccct ttgccctggt agactctgac catgtggaga tgaccatcta    3240
ggacctttct tagacatgag ttcccatcaa catcctgatg gtgggtctcc tacttctggg    3300
attgcagatt gagggcatgg ggagaatgtt gcatgttgtt ttgtggtgct tgttattaca    3360
cgtttgaata aacagtgctg cgaacagttg tcaagaagaa gcc                     3403
```

<210> SEQ ID NO 24
<211> LENGTH: 3247
<212> TYPE: DNA
<213> ORGANISM: Mus musculus
<220> FEATURE:
<221> NAME/KEY: misc_feature
<222> LOCATION: (1)..(3247)
<223> OTHER INFORMATION: Mouse MG29 (NM_008596)

<400> SEQUENCE: 24

```
gcggggcagc gcggcggaca gagcctccga gagcgcgagc agcagcgccc ccacgaccca      60
gcccgccagc ctggagcccg gcctgcccac ggcctcgagc ccgccgcccc cagcgccccc     120 gcgcccacg cagcctcccg gccagggagt cgaaccttg cactgcgccc cgacgcgcca     180
gcatgtcctc gacggagagc cccggccgca cctcggacaa gtctccgcgc cagcaggtgg     240
accgcctgct cctggggctg cgctggcagc gcctggagga gccgctgggc ttcatcaaag     300
ttctccagtg gctctttgct attttcgcct tcgggtcctg cggctcttac agcggggaga     360
cgggagcctt ggttctctgc aacaacgaag ccaaggacgt gagctccatc attgttttgt     420
tcggctatcc cttcaggttg taccaggtcc agtatgagat gcctctctgt gatcaggact     480
ccacctccaa aaccatgaac ctcatgggag acttctctgc cccgccgag ttctttgtga     540 cccttggcat cttttccttc ttctacacaa tggctgccct ggtcatctac ctgcgcttcc     600
```

```
acaaactcta cacagagaac aaacgcttcc cgttggtgga tttctgtgtg actgtctctt    660
tcaccttctt ttggctggtt gctgccgctg cctggggcaa gggcttgact gacgtcaaag    720
gggccacccg gccatccagc ctgactgcag ccatgtctgt gtgccatgga gaggaggcag    780
tgtgcagcgc cggggccaca ccctctatgg ggctggctaa cctctctgtg ctctttggct    840
ttatcaactt cttcctgtgg gctggaaact gttggtttgt gttcaaagag accccgtggc    900
acggacaagg ccaggaccag ggccagggcc ccagccagga gagtgcagcg gagcaggggg    960
cagtggagaa gcagtaagca gccttcatct gcctactccc caactggacg gcaccttgtc   1020
agctcctcca gcttctacag gacctcctcc tcttcctctt cctcctgctc ctcctctccc   1080
tcctcctcca actcccttcc cccatcattc tggactttga gatttgagag aatggatggg   1140
tgggcatcag ctgttggtaa cctgggcaga cctccactgg cttcctatcc ctcatcctgc   1200
tggggcagca aacggcagga tctcagtgct tcttgtctgc tgcctggact gaagcatctt   1260
acttggggaa gctgactggc aaccttgccc tgagttctgt gtggagggcc accagtgat    1320 tttgtggcat ccctcaataa ctggcatcta atctgtatcc tatctctagc cctcccagag   1380
cccagtgtgc tcccaccatg tgtgaagcag ggagacccat tatcctatca gaggtccctc   1440
taagggtcca catgagaccc ggacccaatg ggagcagaga gagttgcaag tacattgcag   1500
caccaaggaa gaaagtgagg aaagttgctg gcagaataag ttttctgttc cctcagccct   1560
tcctttccct cagctggaac actttcggta gcaccctata caccacttac tcatgaaacc   1620
ccttactccc ttctccttct cggccttggt tttgtgggct ttgggagggc ctgaaggacc   1680
atcgtgacat gagatgccca ggagtcccgg gacaaggata catgggccca cctgtccctt   1740
accgtctgtt catttctca agccagcacc ttttctagtt ctttcaaacc tttctgtccc   1800
atctttacaa agagggttat ctgtccttgt ctctcgcctc catgcagtag ccaggcccca   1860
tccttcccca gtcctgggca gcccgatgct attggtgctt cttcatttcg ggacccagat   1920
ccatatttgt ctttggtgtg tctcctctcc ctgattcctc ctgtcatccc tctttgggcc   1980
cgaaggccag agggtaccaa ctgggcaaat gccatctgcc ttttacccag atcaaaaccc   2040
cttgatctac cctggcagta gggttgctta gggaaagatg ataaagaagg aagaaaccag   2100
ccgtttccca atttagtggc aattgtccca cttagcaccc caaagatgaa tgtaccttgt   2160
gccaacctgt cctcatgaca tgatcgaccc tctccaaccc ccttgccttc ctcaatgcta   2220
cccacatcaa gatgtatttc ttggggggccc agggctcaga atccttaact ttgggctgtt   2280
catttcttct ttgggttaca attccccac ccttcagagg aagtaggata tttacacact   2340
ttcagatgct cccgagccat tcagtaaaat aatttggaat ttttgttttc tgcttaagat   2400
tttagggaaa agatttaagg aggggaaaat ttgatgaggg tgagaatgat cctaaatctg   2460
aaactctcta tcctaagttg tccccatggt tacttaagga caagggagac agttttgcct   2520
ccagctccag aggtacaaag aacaaaagag tgaccatttt tcttcaaaca gtccctgtg    2580 gggatctggg agcagcttcg actcaaactg tgtttggatt ctgcgtctat atttataatt   2640
tatttgaact gtgacggata aagtgttctc atttggggcc caagttagca actggcccat   2700
caactacttt agagtaggag ttatccactc ccaccgagca ttcgtactcc agggctcgct   2760 ctaggggttga aaaggctctt cctggcaaga gtctggctat ggccaagaga gtcttgattt   2820
aggctatggt cttttccatgg ccgccggaag aggaaagacc agttcacctc attacctcca   2880
gggggctggg cagcagtaag tgccaagggc agctctgtcc tcatgagact cgtgtcctct   2940
ccaaccaggg ctggcaccac cactttgcct agtcaggcct gaagcgggag aggtgtctgg   3000
```

-continued

| | |
|---|---|
| tttctctagc tattgcagga ggccaacaag cagggaactt gcccttttgcc ctggtagact | 3060 |
| ttaccatgtg gagacgccta tccaggacct ttcttagaca tgagtcccct tcaacatcct | 3120 |
| gaccatgggc ctcctatttc tgggattgca gatcgaggat gtggggagaa tgttgcatgt | 3180 |
| tgttctgtgg tgcttgttac tacacatttg aataaacagt gctgcgaaca tttgccaaga | 3240 |
| agaagcc | 3247 |

<210> SEQ ID NO 25
<211> LENGTH: 1897
<212> TYPE: DNA
<213> ORGANISM: Xenopus laevis
<220> FEATURE:
<221> NAME/KEY: misc_feature
<222> LOCATION: (1)..(1897)
<223> OTHER INFORMATION: X. laevis MG29 (NM_001086184)

<400> SEQUENCE: 25

| | |
|---|---|
| gtgagaaggt gacagaggga gagaggaggg aggaggcaaa aagggcagaa agccaggggc | 60 |
| taagtgagtc tggggcacag gaacgagact ggatataagg gatacaaata tacaaccact | 120 |
| ttggcaggtt gcatgtgact taatgaagca gtagaaaatat cttaaaattg tcagtaaata | 180 |
| acaaaaagga tattttttagc cttatttaca gaatacccag agaacgatat tggaacagtg | 240 |
| ataccaaatt acagtaagca gttaaataag gacgtaactg cattacaaat agtagtaggt | 300 |
| acataaaaaa gtaacaggtt tacagaaact ggtcatcaag aggagccgac atactctctt | 360 |
| tacttggata cttgagccct tctgttcaga cttccagcca ctcacccgtg ggcacctttta | 420 |
| aacaaggacc atgtcaacag cagttccctc ctcaacgatg gacagattgg ggggccttgc | 480 |
| aggacttggc aagaagaacc catttgccgg actacgctgg aggaggttag aggagccatt | 540 |
| gggattcatt aagttgctgg aatggctgtt tgctatattt gcctttggaa gttgtgggtc | 600 |
| atacagtgga gagacagcag caactgtcat gtgcaagtca gaagcagaca cagaaataaa | 660 |
| gctaatttcg gttcccttttg gatacccatt caggctgtat cgccaacgct atgagatgcc | 720 |
| agcttgtgac gatatggaaa ggcgtattct ccatctgaca ggggatttct ctgcccctgc | 780 |
| agagttctttt gtgacaatgg gagtctttgc attcctatac gccatgtttg cactggttat | 840 |
| ctatttacgt ttccatgaag aatacaccaa atccgcaga ttgccaattg tggatttgtg | 900 |
| tgtgactggc gccttcacct ttttgtggct tgtggcagct tcagcttggg gaaaaggcct | 960 |
| gatggatgtg aaggtggcta ctcaaccttc cagccttgtc tcatcaatgc ctctctgcca | 1020 |
| aatgaaaaaa gccacatgca atgctggctc ttcaccatat tttgcccttg ctaacatatc | 1080 |
| tgtgctctttt ggcttttctga atttcattat ctgggctgcc aatatatggt ttgtgtttaa | 1140 |
| agagaccaca tggagtaaga aacctgcctc caaggaagaa tctgcagagc gtggagaggt | 1200 |
| tgaagaccac tagtgatacc tgacaaacat attcctgggt ttccaacaca tactcttacc | 1260 |
| ctactgaaat tctaggactg agtcccattc accttcttct ttaccaggct tcaaataatc | 1320 |
| aactgttcaa ttcttttatga cctttttatta tttaccctga cactgcccac atatagcgaa | 1380 |
| tatgattaat gttccaaaaa catacatagg tgcttataaa aaaagcttat tgtagggttg | 1440 |
| gttgcactgt atttaataca gcccagcata cagcatatat atgttacaat caggcctgga | 1500 |
| ctgggattca aaataggccc tgatttttca agtatataga ggcagataca gcccccacca | 1560 |
| gcccatgact ttctttggaa tcttacgaaa gcccctctgg cattttgcca gaatctgcag | 1620 |
| attgccagtc tgggcctggt tacaataagt aacccagttt ataccaaacc gtaaacacaa | 1680 |
| atgaattaac gcagggttga attctttata atgcagtcta taacagtatt tattttttaaa | 1740 |

```
tatgtgccct actgtaaagg acagtactga ttcatattat gctttctatt agaattgtct    1800
cctgtccttt tcaaagaaaa taacctttct cacctgtcca cagtgtctct ggtgctattt    1860
attaaataaa aacaaatatt ctaaaaaaaa aaaaaa                              1897
```

<210> SEQ ID NO 26
<211> LENGTH: 264
<212> TYPE: PRT
<213> ORGANISM: Rattus norvegicus
<220> FEATURE:
<221> NAME/KEY: MISC_FEATURE
<222> LOCATION: (1)..(264)
<223> OTHER INFORMATION: Rat MG29

<400> SEQUENCE: 26

```
Met Ser Ser Thr Glu Ser Pro Gly Arg Thr Ser Asp Lys Ser Pro Arg
1               5                   10                  15

Gln Gln Val Asp Arg Leu Leu Gly Leu Arg Trp Gln Arg Leu Glu
            20                  25                  30

Glu Pro Leu Gly Phe Ile Lys Val Leu Gln Trp Leu Phe Ala Ile Phe
        35                  40                  45

Ala Phe Gly Ser Cys Gly Ser Tyr Ser Gly Glu Thr Gly Ala Leu Val
    50                  55                  60

Arg Cys Asn Asn Asp Pro Lys Asp Val Ser Ser Ile Val Leu Phe
65                  70                  75                  80

Gly Tyr Pro Phe Arg Leu Tyr Gln Val Gln Tyr Glu Met Pro Leu Cys
                85                  90                  95

Asp Glu Glu Ser Thr Ser Lys Thr Met Asn Leu Met Gly Asp Phe Ser
            100                 105                 110

Ala Pro Ala Glu Phe Phe Val Thr Leu Gly Ile Phe Ser Phe Phe Tyr
        115                 120                 125

Thr Met Ala Ala Leu Val Ile Tyr Leu Arg Phe His Lys Val Tyr Thr
    130                 135                 140

Glu Asn Lys Arg Phe Pro Leu Val Asp Phe Cys Val Thr Val Ser Phe
145                 150                 155                 160

Thr Phe Phe Trp Leu Val Ala Ala Ala Trp Gly Lys Gly Leu Thr
                165                 170                 175

Asp Val Lys Gly Ala Thr Arg Pro Ser Ser Leu Thr Ala Ala Met Ser
            180                 185                 190

Val Cys His Gly Glu Glu Ala Val Cys Ser Ala Gly Ala Thr Pro Ser
        195                 200                 205

Met Gly Leu Ala Asn Ile Ser Val Leu Phe Gly Phe Ile Asn Phe Phe
    210                 215                 220

Leu Trp Ala Gly Asn Cys Trp Phe Val Phe Lys Glu Thr Pro Trp His
225                 230                 235                 240

Gly Gln Gly Gln Asp Gln Gly Gln Gly Pro Ser Gln Glu Ser Ala Ala
                245                 250                 255

Glu Gln Gly Ala Val Glu Lys Gln
            260
```

COMPOSITIONS AND METHODS MODULATING MG29 FOR THE TREATMENT OF DIABETES

CROSS-REFERENCE TO RELATED APPLICATIONS

The present application claims the benefit under 35 USC 119(e) of U.S. Provisional Patent Application Ser. No. 61/217,926, filed: Jun. 5, 2009, entitled: Compositions and Methods Modulating MG29 for the Treatment of Diabetes, and is a Continuation-in-Part of U.S. patent application Ser. No. 12/504,331, filed: Jul. 16, 2009, entitled: Compositions Comprising MG29 Nucleic Acids, Polypeptides, and Associated Methods of Use, which are both incorporated herein by reference in their entirety for all purposes.

STATEMENT REGARDING FEDERALLY SPONSORED RESEARCH

The U.S. Government has certain rights in this invention pursuant to the following grants: RO1-AG15556 awarded to Dr. Jianjie Ma by the United States National Institutes of Health (NIH).

FIELD OF THE INVENTION

This invention relates to recombinant nucleic acid and polypeptide compositions and methods of use thereof for the modulation of muscle function and treatment of disease.

INCORPORATION BY REFERENCE

A Computer Readable Form of the Sequence Listing is filed herewith: file name: MG29v2_seqlist_ST25.txt; size 68 KB; created on: Jun. 3, 2010; using PatentIn-3.5, and Checker 4.4.0 is hereby incorporated by reference in its entirety.

BACKGROUND

The triad junction of skeletal muscle is comprised of a single invagination of the plasma membrane that plunges into the cytoplasm (the transverse-tubules or T-tubules) that is juxtaposed with two sections of the terminal cisternae of the sarcoplasmic reticulum (SR). Screening of an antibody library for novel proteins that localize to the triad junction by immunostaining identified proteins that are implicated in excitation-contraction (E-C) coupling and other aspects of $Ca^{2+}$ handling in skeletal muscle. One protein identified during the screening of this library was a novel transmembrane protein called, mitsugumin29 (MG29).

MG29 is nearly exclusively expressed in skeletal muscle fibers, although some minor levels of expression can be resolved in the kidney, and contains four transmembrane domains that allow the protein to localize at both the transverse (T-) tubular membrane and SR membranes of the triad junction. This subcellular distribution suggest MG29 may mediate communication between the T-tubular and junctional SR membrane. The protein structure of MG29 is homologous in amino acid sequence and shares characteristic structural features with the members of the synaptophysin family of transmembrane proteins essential for neurotransmitter release.

Synaptophysin was originally identified as an abundant and highly immunogenic membrane protein of small synaptic vesicles that is also found in dense-core chromaffin and neurosecretory granules. Synaptophysin and its homologues, synaptoporin (or synaptophysin II) and pantophysin, share a common transmembrane organization, with four membrane-spanning regions and cytoplasmic amino and carboxy termini.

A unique feature of synaptophysin is that it has an oligomeric structure, leading to the proposal that synaptophysin may be a component of the fusion pore that forms during neurotransmitter release. Moreover, Alder et al. have shown that antisense oligonucleotides complementary to the synaptophysin mRNA reduce $Ca^{2+}$-dependent glutamate secretion from *Xenopus* oocytes induced by injection of total brain mRNA. Microinjection of synaptophysin antibody into motor neurons blocked neuromuscular transmission. These data are consistent with synaptophysin being essential for neurotransmitter secretion. However, genetic approaches to identify the function of synaptophysin have not been successful; mutant mice lacking synaptophysin show a normal phenotype. This may reflect compensation by synaptoporin or other synaptophysin family members. Indeed, mice doubly deficient in synaptophysin and synaptogyrin display defects in synaptic plasticity.

Synaptophysin has been proposed to play a structural role in vesicle formation. Based on its high capacity to bind cholesterol, synaptophysin has been implicated in the generation of membrane curvature during synaptic vesicle biogenesis. Synaptophysin is also known to tightly interact with other proteins of the synaptic vesicle membrane, i.e. synaptobrevin and the vacuolar $H^+$-ATPase. These interactions are thought to regulate exocytotic membrane fusion at the level of the SNARE complex or fusion pore formation. The latter idea is supported by studies on yeast vacuole fusion that implicate the vacuolar ATPase directly participate in membrane fusion.

The similarities between MG29 and synaptophysin prompted an investigation into whether MG29 plays an important role in modulation of membrane structures in skeletal muscle. Skeletal muscles are among the most plastic tissue in nature, and normal muscle physiology requires the formation and maintenance of the complex membrane structures. Throughout development, aging and other processes including fatigue require constant adaptations of the skeletal muscle system, thus identification and characterization of genes and proteins involved with plasticity in skeletal muscle membrane structures is essential to understand muscle physiology, as well as treating and diagnosing pathologies related to muscle dysfunction, including diabetes.

Skeletal muscle is a form of striated muscle tissue existing under control of the somatic nervous system. It is one of three major muscle types, the others being cardiac and smooth muscle. Skeletal muscle accounts for as much as 80% of insulin-sensitive glucose metabolism and a substantial portion of whole body glucose metabolism in humans. Insulin resistance (IR) of skeletal muscle is a major risk factor for metabolic disease and is characteristic of type 2 diabetes mellitus, obesity, and hypertension. A substantial body of literature identifies the proximal steps of glucose metabolism, those of glucose delivery, transport, and phosphorylation, as key loci of insulin action in health and as determinants of skeletal muscle insulin resistance.

Therefore, an understanding of the mechanism and regulation of muscle glucose utilization is necessary to determine the nature of the defects present in metabolic diseases such as obesity and insulin-resistant diabetes. Glucose transport, the initial step in glucose utilization, is often considered rate determining in glucose utilization in muscle. One approach to assessing the balance of transport and phosphorylation in determining glucose utilization is to establish how these processes are coupled at the cellular level Diabetes mellitus is a metabolic disorder characterized by an inability to control blood glucose levels due to either a loss of the insulin-producing beta cells of the islets of Langerhans in the pancrease, which leads to insulin deficiency (i.e., Type I diabetes), and/or due to insulin resistance (i.e., Type II diabetes or NIDD).

Type I diabetes can be further classified as immune-mediated or idiopathic. The majority of type 1 diabetes is of the immune-mediated nature, where beta cell loss is a T-cell mediated autoimmune attack. There is no known preventive measure against type 1 diabetes, which causes approximately 10% of diabetes mellitus cases in North America and Europe. Most affected people are otherwise healthy and of a healthy weight when onset occurs. Sensitivity and responsiveness to insulin are usually normal, especially in the early stages. Type 1 diabetes can affect children or adults but was traditionally termed "juvenile diabetes" because it represents a majority of the diabetes cases in children.

With Type II diabetes the defective responsiveness of body tissues to insulin is believed to involve the insulin receptor. However, the specific defects are not known. In the early stage of Type II diabetes, the predominant abnormality is reduced insulin sensitivity. At this stage hyperglycemia can generally be reversed by a variety of measures and medications that improve insulin sensitivity or reduce glucose production by the liver. As the disease progresses, the impairment of insulin secretion occurs, and therapeutic replacement of insulin may sometimes become necessary in certain patients.

If the amount of insulin available is insufficient, if cells respond poorly to the effects of insulin (insulin insensitivity or resistance), or if the insulin itself is defective, then glucose will not have its usual effect so that glucose will not be absorbed properly by those body cells that require it nor will it be stored appropriately in the liver and muscles. The net effect is persistent high levels of blood glucose, poor protein synthesis, and other metabolic derangements, such as acidosis.

When the glucose concentration in the blood is raised beyond its renal threshold (about 10 mmol/L, although this may be altered in certain conditions, such as pregnancy), reabsorption of glucose in the proximal renal tubuli is incomplete, and part of the glucose remains in the urine (glycosuria). This increases the osmotic pressure of the urine and inhibits reabsorption of water by the kidney, resulting in increased urine production (polyuria) and increased fluid loss. Lost blood volume will be replaced osmotically from water held in body cells and other body compartments, causing dehydration and increased thirst.

Lack of adequate treatment of diabetes can lead to acute complications, including hypoglycemia, diabetic ketoacidosis, nonketonic hyperglycemia, or nonketotic hyperosmolar coma. Serious long-term complications include cardiovascular disease, e.g., heart attack, stroke, arterial diseases (e.g., coronary artery disease); neuropathy; renal failure; retinal damage; erectile dysfunction; blindness, slow healing wounds; and amputation.

As of 2000 at least 171 million people worldwide suffer from diabetes, or 2.8% of the population. Type 2 diabetes is by far the most common, affecting 90 to 95% of the U.S. diabetes population (Wild S, Roglic G, Green A, Sicree R, King H (May 2004). "Global prevalence of diabetes: estimates for 2000 and projections for 2030". *Diabetes Care* 27 (5): 1047-53). Accordingly, there exists an ongoing need for the development of pharmaceutical modulators of muscle function for the treatment of conditions related to muscle dysfunction, including diabetes.

SUMMARY

The invention relates to the surprising and unexpected discovery of genes, proteins, and processes involved in glucose metabolism in muscle cells. In particular, The present invention provides nucleic acids encoding MG29 polypeptides and bioactive portions thereof (herein "MG29 nucleic acids" and "MG29 polypeptides", respectively), nucleic acids complementary to nucleic acids encoding MG29 polypeptides and bioactive portions thereof, vectors and/or host cells comprising the same, MG29 polypeptides and fusion proteins, antibodies or antigen-binding domains specific for an epitope of MG29, host cells and transgenic organisms in which the expression of an endogenous MG29 gene or exogenous MG29 transgene is modulated.

In additional aspects, the invention provides diagnostic assays and methods of screening for chemical compounds that modulate the activity, transcription, and/or translation (i.e., expression) of MG29, and methods of using the same.

In further aspects, the present invention provides compositions useful as therapeutics for treating and prevention of diabetes. Therapeutic compositions of the invention comprise MG29 polypeptides and fusion proteins, nucleic acids encoding MG29 polypeptides, and nucleic acids complementary to nucleic acids encoding MG29 including ribose-containing nucleic acids. This aspect of the invention also encompasses MG29 mutants, homologs, fragments, truncations, pseudopeptides, peptide analogs, and peptidomimetics.

In another aspect, the invention provides compounds that can modulate the activity, transcription and/or translation (i.e., expression) of MG29. As described herein, MG29 is an important constituent of cellular structures and physiological processes critical for normal muscle function, including glucose metabolism. As such, the targeting and modulating MG29 gene expression, polypeptide synthesis, activity or protein-protein interactions represents a novel therapeutic intervention for treating pathologies relating to muscle dysfunction, including, for example, diabetes.

Previous findings indicated that aberrant MG29 function and/or gene expression leads to muscle dysfunction and aging. As described herein, we have surprisingly and unexpectedly discovered that MG29 can serve as a modulator of blood glucose, and therefore, its modulation is useful in the treatment of diabetes. In particular, the MG29 protein interacts with other factors that are important players in the process to absorb glucose from the blood stream into skeletal muscle. Accordingly, the present invention also provides compositions and methods that can modulate the expression and/or activity of MG29 in skeletal muscle to assist in the treatment of diabetes. Modulating the mechanisms of MG29 gene expression control as described herein provides an effective tool to treat diabetes and other muscle diseases.

In certain additional aspects the invention provides compositions and methods related to the diagnosis, treatment or amelioration of diabetes. In certain exemplary embodiments, the invention encompasses, for example, the administration of an effective amount of a therapeutic composition of the invention for the prevention and/or treatment of diabetes. In certain embodiments, the therapeutic composition comprises a nucleic acid, including inhibitory nucleic acids (e.g., antisense and/or interfering nucleic acids) that modulate the activity, transcription and/or translation of MG29, a recombinant MG29 polypeptide; and/or a small molecule capable of modulating MG29 activity, transcription and/or translation. In other embodiments, the invention relates to diagnostic compositions useful for diagnosing or monitoring a disease or condition related to muscle function comprising a nucleic acid that is complementary to or capable of hybridizing to at least a portion of an MG29 encoding nucleic acid, for example, an MG29 gene or RNA.

The present invention further provides any invention described herein.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
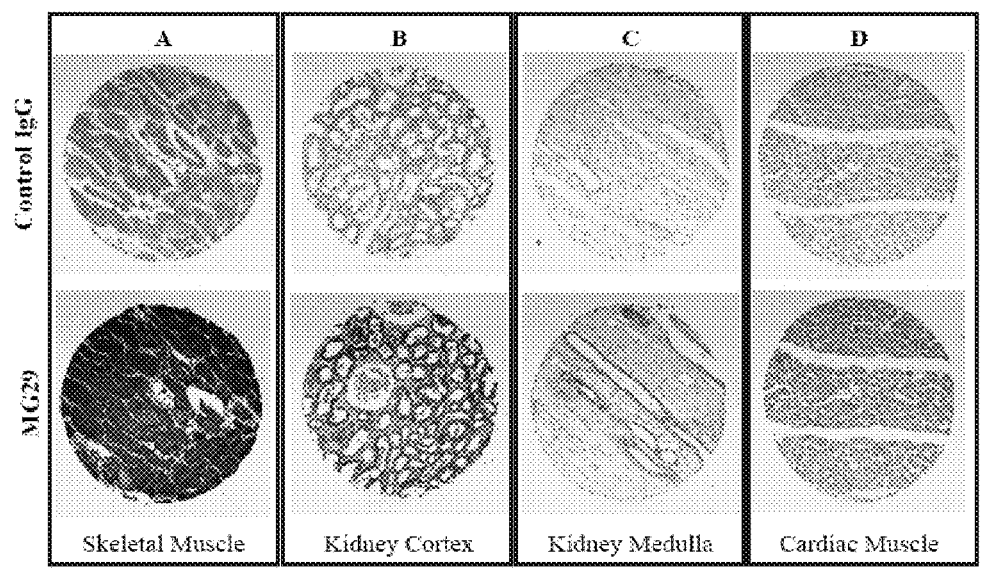
FIG. 1. MG29 protein in humans is only expressed in the skeletal muscles and epithelium of the kidney. Staining of a paraffin-embedded multiple tissue microarray (MTA) using a monoclonal anti-MG29 antibody (bottom) or control non-immunized IgG (top). Dark purple signal indicates expression of MG29 (SEQ ID NOs: 3, 4). While MG29 is heavily expressed in skeletal muscle (A) it also appears in the epithelial lining of the kidney (B, C). Expression is absent from the heart (D) and all other tissues tested (including lung, testes, liver, spleen, brain, etc).

Presently described are compositions and methods relating to the surprising and unexpected discovery that MG29 is an important structural and functional component in the processes that govern the function of skeletal muscle in the regulation of blood glucose.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). As used herein, the following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

The term "about" as it is used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

As used herein, "derivatives" are compositions formed from the native compounds either directly, by modification, or by partial substitution. As used herein, "analogs" are compositions that have a structure similar to, but not identical to, the native compound.

The term "MG29" is used in a general sense to refer to MG29 polynucleotides or polypeptides, respectively, and encompasses biologically-active fragments, portions, splice variants, and homologs thereof. See SEQ ID NOs.: 1-8, 26 and 20-25).

The term "MG29 antagonist" or "antagonist of MG29" is used generally to refer to an agent capable of direct or indirect inhibition of a MG29, expression, translation, and/or activity. the term "MG29 agonist" or "agonist of MG29" is used generally to refer to an agent capable of direct or indirectly increasing MG29, expression, translation, and/or activity.

The term "polypeptides" can mean, but is in no way limited to, recombinant full length, pro- and/or mature polypeptide forms as well as the biologically active forms, including fragments or splice variants, or recombinantly made truncations or portions derived from the full length polypeptides. Furthermore, polypeptides of the invention may include amino acid mimentics, and analogs. Recombinant forms of the chimeric polypeptides can be produced according to standard methods and protocols which are well known to those of skill in the art, including for example, expression of recombinant proteins in prokaryotic and/or eukaryotic cells followed by one or more isolation and purification steps, and/or chemically synthesizing cytokine polypeptides or portions thereof using a peptide synthesizer.

The term, "biologically active" or "bioactive" can mean, but is in no way limited to, the ability of an agent, such as the polypeptides provided by the invention, to effectuate a physiological change or response. The response may be detected, for example, at the cellular level, for example, as a change in gene expression, protein quantity, protein modification, protein activity, or combination thereof; at the tissue level; at the systemic level; or at the organism level. Techniques used to monitor these phenotypic changes include, for example, measuring: the binding of a ligand to its receptor in or on a cell, activation of cell signaling pathways, stimulation or activation of a cellular response, secretion or release of bioactive molecules from the cell, cellular proliferation and/or differentiation, or a combination thereof. In one example, the biological activity of a chimeric polypeptide provided by the invention can be determined by detecting its ability to modulate hematopoiesis, thymopoiesis, and/or thymocytic development as presently described.

The term "fragment" can mean, but is in no way limited to, sequences of at least 6 (contiguous) nucleic acids or at least 4 (contiguous) amino acids, a length sufficient to allow for specific hybridization in the case of nucleic acids or for specific recognition of an epitope or retention of a desired bioactivity in the case of amino acids, and are at most some portion less than a full length sequence.

The term "effective amount/dose," "pharmaceutically effective amount/dose," "pharmaceutically effective amount/dose" or "therapeutically effective amount/dose" can mean, but is in no way limited to, that amount/dose of the active pharmaceutical ingredient sufficient to prevent, inhibit the occurrence, ameliorate, delay or treat (alleviate a symptom to some extent, preferably all) the symptoms of a condition, disorder or disease state. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

Non-limiting examples of agents suitable for formulation with the, e.g., nucleic acids provided by the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic destruction of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "nucleotide" can mean, but is no way limited to, a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

The term "nucleic acid" or "polynucleotide" can mean, but is in no way limited to, a molecule having more than one nucleotide, and is intended to include DNA molecules (e.g., cDNA or genomic DNA), RNA molecules, analogs of DNA or RNA, including locked nucleic acids and peptide nucleic acids, and derivatives thereof. The nucleic acid can be single, double, or multiple stranded and can comprise modified or unmodified nucleotides or non-nucleotides or various mixtures and combinations thereof. The nucleic acids of the invention are added directly, or can be complexed with cationic lipids, packaged within liposomes, or otherwise delivered to target cells or tissues. The nucleic acid or nucleic acid complexes can be locally administered to relevant tissues in vitro, ex vivo, or in vivo through injection or infusion pump, with or without their incorporation in biopolymers.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

The term "modified bases" can mean, but is in no way limited to, nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule. The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163).

The term "derivatives" can mean, but is in no way limited to, chemical compositions, for example, nucleic acids, nucleotides, polypeptides or amino acids, formed from the native compounds either directly, by modification, or by partial substitution. The term "analogs" can mean, but is in no way limited to, chemical compositions, for example, nucleic acids, nucleotides, polypeptides or amino acids that have a structure similar to, but not identical to, the native compound.

The term "hybridization" can mean, but is in no way limited to, the binding, duplexing, or hybridizing of a molecule only to a particular nucleotide sequence under low, medium, or highly stringent conditions, including when that sequence is present in a complex mixture (e.g., total cellular) DNA or RNA.

The term "conservative mutations" refers to the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

The term "down-regulate" can mean, but is in no way limited to, the expression of the gene, or level of RNAs or equivalent RNAs encoding one or more proteins, or activity of one or more proteins, such as MG29 polypeptide genes, is reduced below that observed in the absence of an agent provided by the invention. For example, the expression of a gene can be decreased in order to treat, prevent, ameliorate, or modulate a pathological condition caused or exacerbated by high levels of gene expression.

The term "up-regulate" can mean, but is in no way limited to, the expression of the gene, or level of RNAs or equivalent RNAs encoding one or more protein subunits, or activity of one or more protein subunits, e.g., MG29, is greater than that observed in the absence of an agent provided by the invention. For example, the expression of a gene can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of an agent provided by the invention.

The term, "gene" can mean, but is in no way limited to, a nucleic acid that encodes RNA, for example, nucleic acid sequences including but not limited to a segment encoding a polypeptide.

The term "complementarity" can mean, but is in no way limited to, the ability of a nucleic acid to form hydrogen bond(s) with another RNA sequence by either traditional Watson-Crick, Hoogsteen base pairing or other non-traditional types.

The term "binding" can mean, but is in no way limited to, the physical or chemical interaction, direct or indirect, between two molecules (e.g., compounds, amino acids, nucleotides, polypeptides, or nucleic acids). Binding includes covalent, hydrogen bond, ionic, non-ionic, van der Waals, hydrophobic interactions, and the like.

The term "equivalent" or "homologous" can mean, but is in no way limited to, nucleic acids or proteins include those naturally occurring DNA, RNA or amino acid molecules have homology (partial or complete) to MG29 genes (SEQ ID NOs: 20-25) or proteins (SEQ ID NOs: 1-8, 26), respectively, with similar function as MG29 in various organisms, including human, rodent, primate, rabbit, pig, protozoans, fungi, plants, and other microorganisms and parasites. The equivalent RNA sequence also includes, in addition to the coding region, regions such as 5'-untranslated region, 3'-untranslated region, introns, intron-exon junction and the like. By "homology" is meant the nucleotide sequence of two or more nucleic acid molecules or two or more nucleic acid or amino acid sequences is partially or completely identical. In certain embodiments the homologous nucleic acid or amino acid sequence has 30%, 40%, 50%, 60%, 70%, 80%, 90%, or 95% sequence similarity or identity to human MG29 gene (SEQ ID NOs: 21 or 22) or protein (SEQ ID NOs: 3 or 4), respectively. In certain embodiments, the invention provides a nucleic acid having 30%, 40%, 50%, 60%, 70%, 80%, 90%, or 95% similarity or identity to a nucleic acid encoding an MG29 polypeptide selected from SEQ ID NOs.: 1-8 and 26 or a bioactive portion thereof. In additional embodiments, the invention provides a polypeptide having 30%, 40%, 50%, 60%, 70%, 80%, 90%, or 95% similarity or identity to an MG29 polypeptide selected from SEQ ID NOs.: 1-8 and 26 or a bioactive portion thereof.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. For purposes of the present invention, genes are homologous if the nucleic acid sequences are sufficiently similar to allow recombination and/or hybridization under low stringency conditions. In addition, polypeptides are regarded as homologous if the polypeptide provides activity comparable to wild type MG29.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

The term "RNA" can mean, but is in no way limited to, a molecule comprising at least one ribonucleotide residue. By "ribonucleotide" or "2'-OH" is meant a nucleotide with a hydroxyl group at the 2' position of a D-ribo-furanose moiety.

The term "vectors" can mean, but is in no way limited to, any nucleic acid-based technique used to deliver a desired nucleic acid, for example, bacterial plasmid, viral nucleic acid, HAC, BAC, and the like for cloning, amplification, and/or expression of a gene.

The term "cell" can mean, but is in no way limited to, its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

The term "host cell" can mean, but is in no way limited to, a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

The subject matter of U.S. patent application Ser. No. 12/504,331 filed: Jul. 16, 2009, entitled: Compositions comprising MG29 Nucleic Acids, Polypeptides, and Associated Methods of Use, is incorporated herein by reference in its entirety for all purposes.

The major hallmark of diabetes mellitus is the elevation of glucose levels in the blood of affected patients. This state can develop due to reduced insulin secretion, as in type I juvenile diabetes, or due to compromised response of the body to insulin, as in type II insulin resistance diabetes. Skeletal muscle is a major target for insulin as muscle is responsible for much of the glucose consumption in the body and thus can absorb large quantities of glucose in the presence of insulin. For this to occur, vesicles containing glucose transporter type 4 (Glut4) must translocate to the plasma membrane. As described herein, not only does MG29 play an important role in membrane fusion in skeletal muscle, it also contributes to the mechanism controlling the increase of Glut4 on the plasma membrane in response to insulin.

Figure 5:
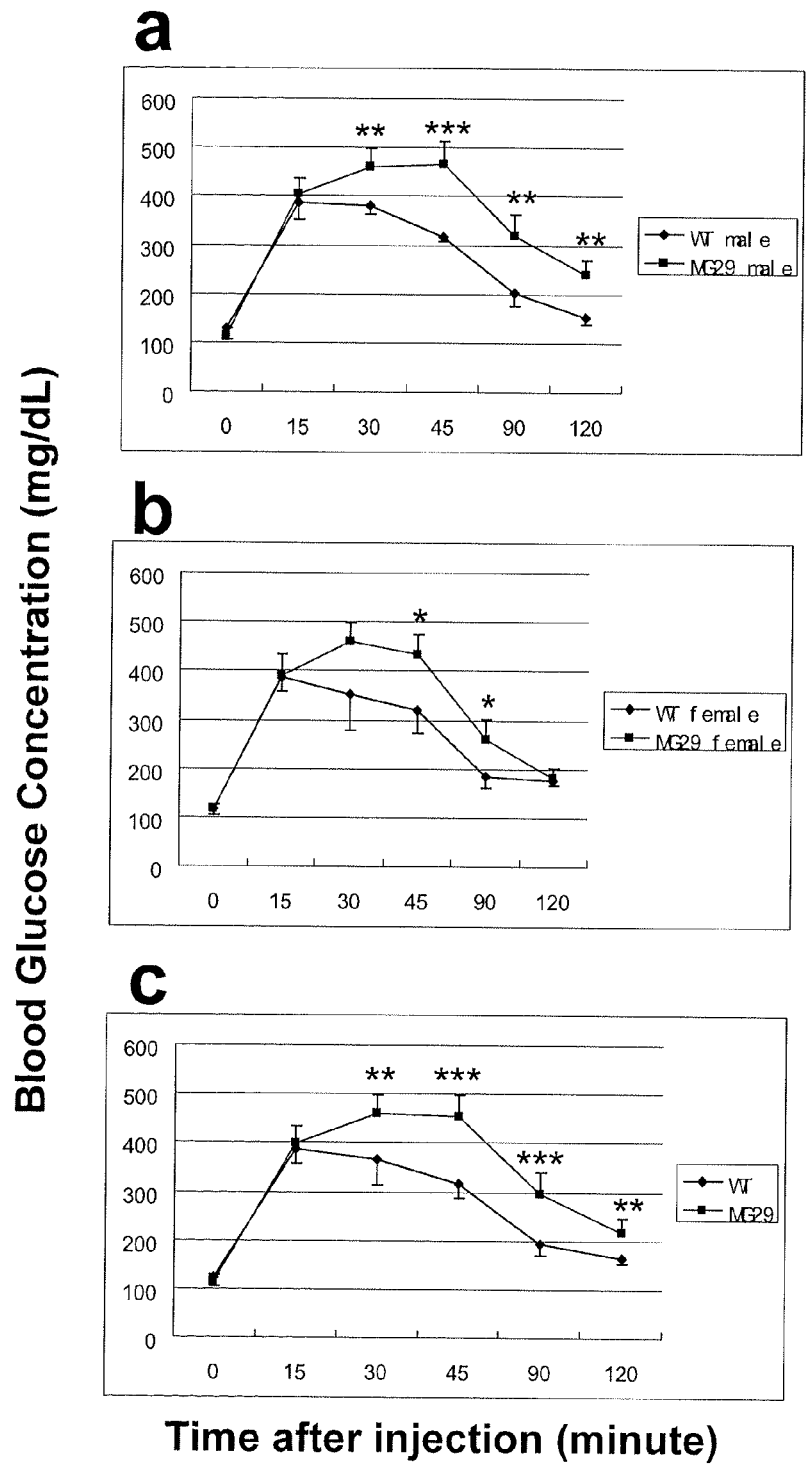
FIG. 5. Mice null for MG29 (mg29−/−) display compromised response to glucose challenge. Fasting blood glucose levels were measured in mice following a bolus IP injection of glucose solution. (a) Male mg29−/− mice show a significantly higher blood glucose level following glucose challenge. Time 0 equals the time of injection. (b) Female mg29−/− mice show a significantly higher blood glucose level following glucose challenge. (c) Mean data pooled from both genders of mice. Analysis by ANOVA with *: P<0.05; : P<0.01; *P<0.001.
Figure 6:
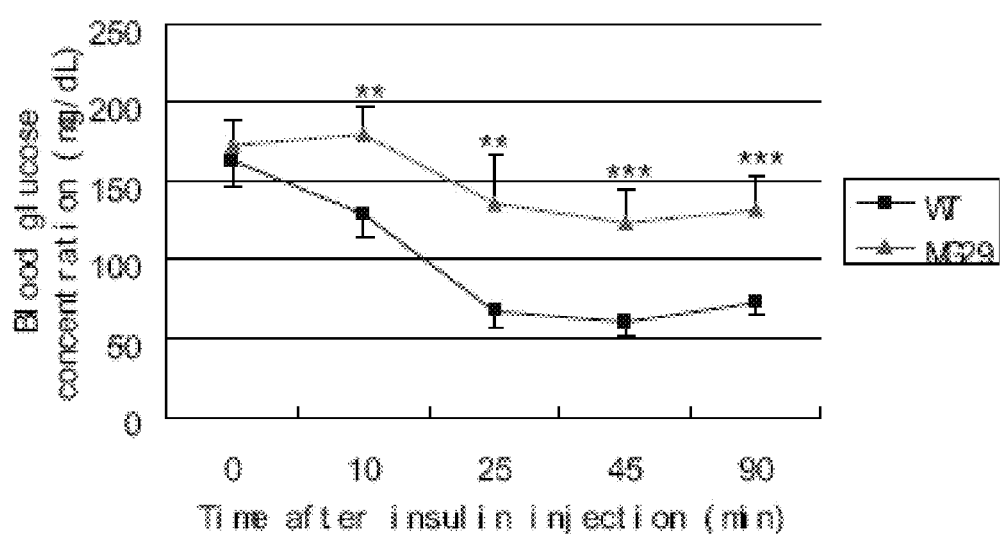
FIG. 6. Mice null for MG29 (mg29−/−) display compromised response to insulin challenge. Fasting blood glucose levels were measured in mice following a bolus IP injection of insulin at time 0 on chart. MG29 (mg29−/−) mice do not respond to the same level as wild type (WT) controls. This indicates that skeletal muscle in the mg29−/− mouse is compromised in its ability to uptake glucose. Mean±SEM is shown. ANOVA is used for analysis with : P<0.01; *P<0.001.

In glucose challenge experiments with young mg29−/− mice it was found that both male and female mg29−/− animals were unable to effectively clear glucose from their bloodstream following a bolus interperitoneal (IP) injection of glucose (FIG. 5). However, the resting glucose level remains unchanged, suggesting that the absence of MG29 does not effect the role of the liver in glucose metabolism. Since the mg29−/− glucose levels remain high for an extended period, it appears there is a defect in the ability of the mg29−/− muscle to uptake glucose rather than a defect in insulin secretion. This was confirmed by further experiments where an insulin challenge was performed on mg29−/− and control animals. While an IP injection of insulin can induce a significant decrease in blood glucose in wild type control animals, the same injection of insulin has much less effect on the blood glucose level in mg29−/− mice (FIG. 6). These findings indicate that the underlying defect leading to elevated blood glucose in mg29−/− mice is in glucose clearance from the animal rather than compromised insulin production, a situation similar to that seen in type II diabetic patients. Thus, absence of MG29 from skeletal muscle can predispose animal to develop diabetic symptoms.

Figure 7:
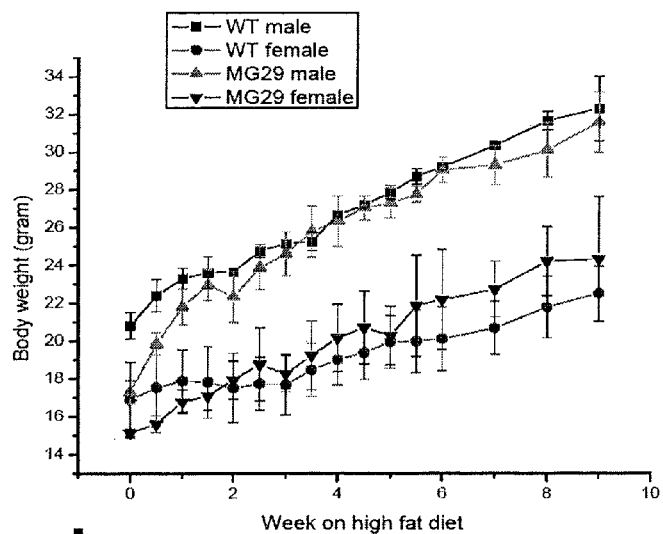
FIG. 7. Mice null for MG29 (mg29−/−) develop diabetes more rapidly when fed a high fat diet. Groups of mice were fed a high fat diet and then measured for changes in body weight and blood glucose. (a) Both MG29 and wild type (WT) mice gain weight at the same rate when fed a high fat diet that began at week 0 on the chart. (b) When challenged with a bolus IP injection of glucose, mg29−/− mice cannot clear glucose as effectively as the WT mice, indicating that mg29−/− mice are developing a diabetic phenotype more rapidly than WT mice. ANOVA is used for analysis with *: P<0.05.
Figure 7:
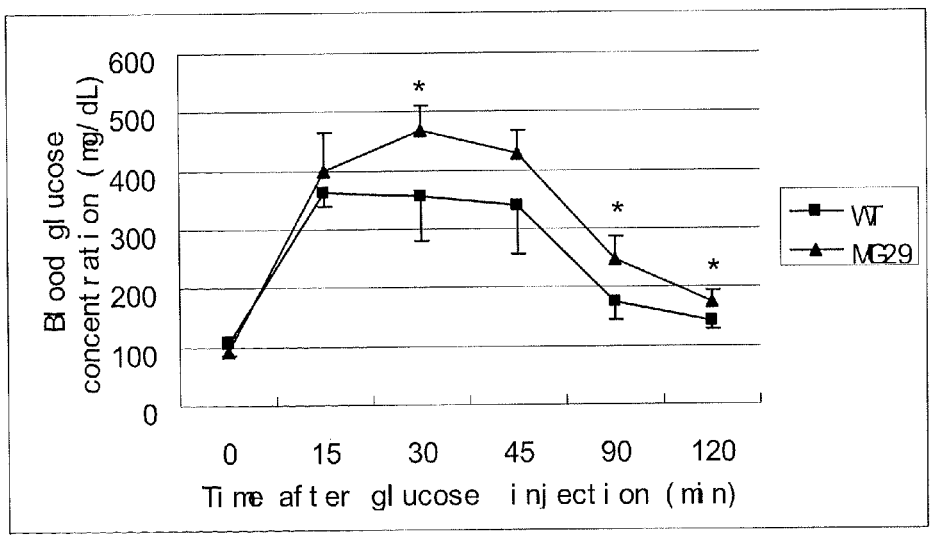

Furthermore, mg29−/− animals were tested to see if they are more susceptible to developing diabetes by feeding them and aged matched wild type control mice a high fat diet. This approach is known to induce diabetes in mice. While mg29−/− and control mice put on weight at similar rates (FIG. 7a), the mg29−/− mice developed a susceptibility to glucose challenge experiments at a much younger age than the control mice (FIG. 7b). This provides additional evidence that MG29 is necessary for skeletal muscle to absorb glucose from the bloodstream to maintain energy supplies in the muscle and decrease the blood glucose levels to prevent diabetes. Because the absence of MG29 can induce diabetes, the manipulation of MG29 expression (i.e., transcription and/or translation) can provide an effective method for treating both type I and type II diabetes.

Also, as described herein, the UTR sequences of the endogenous MG29 mRNA comprise a number of consensus sites for post-transcriptional regulation. Experimental observations indicate that the MG29 UTR sequence (e.g., SEQ ID NO: 21, 23, or 24) is, in fact, necessary for the post-transcriptional regulation of MG29 gene expression, revealing the UTR to be a target of the regulatory pathway in muscle that controls the expression of MG29. Accordingly, modulation of the post-transcriptional regulation of MG29 mRNA exists as another means of therapeutic intervention for diagnosing, treating and preventing diabetes.

Below, is a description various exemplary aspects and embodiments provided by the invention. As described in detail below, the invention provides compositions, for example, polypeptides, nucleic acids encoding cytoplasmic, nuclear, membrane bound, and secreted polypeptides; as well as vectors, antibodies, recombinant proteins, pseudopeptides, fusion proteins, chemical compounds, host cells, transgenic animals, and methods for producing and using the same.

Nucleic Acids

The various aspects and embodiments described below include nucleic acids encoding MG29 polypeptides (e.g., SEQ ID NOs.: 1-8 and 26) and/or bioactive portions and fragments thereof, as well as genes which encode MG29 proteins (e.g., SEQ ID NOs: 20-15), including homologs, orthologs, and paralogs of human MG29 proteins; including all isoforms, splice variants (e.g., SEQ ID NO.: 4), and polymorphisms. Those additional genes can be analyzed for target sites using the methods described herein. Thus, the inhibition and the effects of such inhibition of the other genes can be performed as described herein.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47.

Nucleic acid compositions provided by the invention are collectively and interchangeably referred to herein as "MG29 nucleic acids" or "MG29 polynucleotides", and the corresponding encoded polypeptides are referred to as "MG29 polypeptides" or "MG29 proteins." Unless indicated otherwise, these terms include bioactive portions, fragments, deletions or substitutions, truncations, gene fusions at the amino or carboxy terminal or both, and combinations thereof. Also, unless indicated otherwise, "MG29" is used generally to refer to any MG29 related and/or MG29-derived biopolymers as explicitly, implicitly, or inherently described herein. Also, as used herein, "MG29 nucleic acid" or "MG29 gene" also refers to and includes the 5' UTR, 3' UTR, promoter sequences, enhancer sequences, intronic and exonic DNA of the gene as well as the mRNA or cDNA sequence.

As described above, in certain aspects the present invention relates to nucleic acids, and the polypeptides encoded from nucleic acids of the invention, which, alone or in combination with other components, can modulate muscle physiology, including glucose clearance.

In one aspect, the invention provides an isolated nucleic acid encoding an MG29 polypeptide having at least 30%, 40%, 50%, 60%, 70%, 80%, 90% or 100% identity to any of the nucleic acids disclosed in SEQ ID NOS: 20-25. In certain embodiments, the isolated nucleic acid molecules of the invention will hybridize under stringent conditions to a nucleic acid sequence complementary to a nucleic acid molecule that includes a protein-coding sequence of a MG29 nucleic acid sequence. The invention also includes an isolated nucleic acid that encodes an MG29 polypeptide, or a fragment, homolog, analog, fusion protein, pseudopeptide, peptidomimetic or derivative thereof. For example, the nucleic acid can encode a polypeptide at least 30%, 40%, 50%, 60%, 70%, 80%, 90% or 100% identity to a polypeptide comprising the amino acid sequences of SEQ ID NOS: 1-8 and 26. The nucleic acid can be, for example, a genomic DNA fragment or a cDNA molecule that includes the nucleic acid sequence of any of SEQ ID NOS: 20-25.

In another embodiment, the invention encompasses an isolated or recombinant nucleic acid encoding a recombinant MG29 polypeptide as described above, or as set forth in SEQ ID NOs.: 1-8, or 26, and/or a homolog, or fragment thereof, wherein the polypeptide modulates muscle function, for example, glucose metabolism.

In another aspect, the invention provides derivatives and/or analogs of the MG29 nucleic acids as set forth in SEQ ID NOs: 20-15, and/or the MG29 proteins as set forth in SEQ ID NOs: 1-8 and 26 of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

In another aspect, the invention provides isolated and recombinant nucleic acids encoding MG29 proteins or bioactive portions thereof, for example, a truncated portion encoding only the synaptophysin domain or synaptophysin-like domain or a portion thereof, and/or the marvel domain or marvel-like domain or a portion thereof. As such, the nucleic acids provided by this aspect of the invention encompass MG29 deletions, substitutions, truncations, fusion proteins and the like. In an exemplary embodiment, a recombinant nucleic acid is provided that encodes a recombinant MG29 polypeptide comprising a first region (i.e., portion or domain) having at least 30% homology to a human MG29 (SEQ ID NOs: 3 or 4) synaptophysin domain polypeptide ("synaptophysin-like domain"), and optionally a second region having at least 30% homology to a human MG29 marvel domain polypeptide (or marvel-like domain). In additional embodiments, the invention encompasses the resulting recombinant MG29 polypeptides.

In another embodiment, a recombinant nucleic acid is provided that encodes a recombinant MG29 polypeptide in which the synaptophysin domain or synaptophysin-like domain is juxtaposed with a marvel domain or marvel-like domain. Accordingly, the invention encompasses recombinant polypeptides in which the synaptophysin or synaptophysin-like domain is juxtaposed with a marvel domain or marvel-like domain.

In an additional aspect, the invention encompasses an isolated or recombinant nucleic acid encoding polypeptides formed by expressing genes or cDNA constructs formed by combining polynucleotides encoding amino acid or peptide components from other members of the MG29 family, for example, those specified in TABLES 1 or 2 or SEQ ID NOs.: 1, 2, 5-19, and 26. The nucleic acids encoding the respective amino acid or peptide domains can be cloned from any desired parental gene and combined into a single contiguous nucleic acid using standard molecular biological techniques. Also, because it is generally recognized that evolutionarily conserved amino acid sequences will function similarly, it is within the abilities of those skilled in the art to generate additional proteins in accordance with the instant teachings, and to assess the ability of the recombinant proteins to facilitate glucose clearance as taught herein, without undue experimentation. As such, recombinant proteins assembled from the domains of the MG29 family members, for example, those identified above, is expressly contemplated as being within the scope of the invention.

TABLE 1

UniProtKB/Swiss-Prot MG29 Gene/Protein Structural Homology Data

| | |
|---|---|
| Protein names | Synaptophysin-like protein 2<br>Mitsugumin-29 (MG29) |
| Gene names | Name: Sypl2 Synonyms: Mg29 |
| Function | Involved in communication between the T-tubular and junctional sarcoplasmic reticulum (SR) membranes; i.e., the Triad Junction. (Note = Triad junction, the junctional complex between the transverse tubule and the sarcoplasmic reticulum.); cellular calcium ion homeostasis transport; transporter activity |
| Tissue specificity | Expressed abundantly in skeletal muscle (low levels in kidney) |
| Sequence similarities | Belongs to the synaptophysin/synaptobrevin family. |
| Basic Local Alignment Search Tool hits to human MG29 | (SEQ ID NO. 3) sp Q5VXT5 (and Q5VXT5-2)<br>SYPL2_HUMAN Synaptophysin-like protein 2 [SYPL2] [Homo sapiens (Human)] 272 AA<br>MSSTESAGRTADKSPRQQVDRLLVGLRWRRLEEPLGFIKVLQWLFAIFAFGSCGSYSGET<br>GAMVRCNNEAKDVSSIIVAFGYPFRLHRIQYEMPLCDEESSSKTMHLMGDFSAPAEFFVT<br>LGIFSFFYTMAALVIYLRFHNLYTENKRFPLVDFCVTVSFTFFWLVAAAAWGKGLTDVKG<br>ATRPSSLTAAMSVCHGEEAVCSAGATPSMGLANISVLFGFINFFLWAGNCWFVFKETPWH<br>GQGQGQDQDQDQDQGQGPSQESAAEQGAVEKQ<br>aa 1-267 Synaptophysin domain<br>aa 30-238 MARVEL domain<br>aa 213 N-linked Glycosylation<br><br>(SEQ ID NO. 1) SYPL2_MOUSE Synaptophysin-like protein 2 (Mitsugumin-29) (Mg29) [Sypl2] [Mus musculus (Mouse)] 264 AA<br>Score = 489 bits (1259), Expect = e-136<br>Identities = 239/272 (87%), Positives = 251/272 (92%), Gaps = 8/272 (2%)<br>MSSTESPGRTSDKSPRQQVDRLLLGLRWQRLEEPLGFIKVLQWLFAIFAFGSCGSYSGET<br>GALVLCNNEAKDVSSIIVLFGYPFRLYQVQYEMPLCDQDSTSKTMNLMGDFSAPAEFFVT<br>LGIFSFFYTMAALVIYLRFHKLYTENKRFPLVDFCVTVSFTFFWLVAAAAWGKGLTDVKG<br>ATRPSSLTAAMSVCHGEEAVCSAGATPSMGLANLSVLFGFINFFLWAGNCWFVFKETPWH<br>GQGQDQGQGPSQESAAEQGAVEKQ<br>aa 1 - 264; Synaptophysin-like protein 2<br>aa 30-238 MARVEL<br>aa 213 N-linked Glycosylation<br><br>(SEQ ID NO. 26) D4A6M0_RAT Mitsugumin 29 (Predicted) (Putative uncharacterized protein Syp12)[Syp12][Rattus norvegicus (Rat)]<br>Score = 491 bits (1263), Expect = e-137<br>Identities = 240/272 (88%), Positives = 251/272 (92%), Gaps = 8/272 (2%)<br>>tr\|D4A6M0\|D4A6M0_RAT Mitsugumin 29 (264)<br>MSSTESPGRTSDKSPRQQVDRLLLGLRWQRLEEPLGFIKVLQWLFAIFAFGSCGSYSGET<br>GALVRCNNDPKDVSSIIVLFGYPFRLYQVQYEMPLCDEESTSKTMNLMGDFSAPAEFFVT<br>LGIFSFFYTMAALVIYLRFHKVYTENKRFPLVDFCVTVSFTFFWLVAAAAWGKGLTDVKG<br>ATRPSSLTAAMSVCHGEEAVCSAGATPSMGLANISVLFGFINFFLWAGNCWFVFKETPWH<br>GQGQDQGQGPSQESAAEQGAVEKQ<br><br>(SEQ ID NO. 2) O62646 SYPL2_RABIT Synaptophysin-like protein 2 (Mitsugumin-29) (Mg29) [SYPL2] [Oryctolagus cuniculus (Rabbit)] 264 AA<br>Score = 498 bits (1281), Expect = e-139<br>Identities = 245/272 (90%), Positives = 249/272 (91%), Gaps = 8/272 (2%)<br>MSSTESPSRAADKSPRQQVDRLLEGLRWRRLEEPLGFIKVLQWLFAIFAFGSCGSYSGET<br>GAMVRCNNEAKDVSSIIVLFGYPFRLHRIEYEMPLCDDDSSSKTMHLMGDFSAPAEFFVT<br>LGIFSFFYTMAALVVYLRFHKLYTENKRFPLVDFCVTVSFTFFWLVAAAAWGKGLTDVKG<br>ATRPSSLTAAMSVCHGEEAVCSAGATPSMGLANISVLFGFINFFLWAGNCWFVFKETPWH<br>GQGQDQGQGPSQESAAEQGAVEKQ<br>aa 1-264 Synaptophysin domain<br>aa 30-238 MARVEL domain<br>aa 213 N-linked Glycosylation |

TABLE 1-continued

UniProtKB/Swiss-Prot MG29 Gene/Protein Structural Homology Data (SEQ ID NO. 5) Q0VBZ3_BOVIN Synaptophysin-like 2 [SYPL2] [*Bos taurus* (Bovine)] 264 AA
Score = 490 bits (1262), Expect = e-137
Identities = 241/272 (88%), Positives = 250/272 (91%), Gaps = 8/272 (2%)
MSSTESSSRTADKSPRQQVDRLLVGLRWRRLEEPLGFIKVLQWLFAIFAFGSCGSYSGET
GATVRCNNEAKDVSAIIVSFGYPFRLNRVQYEMPLCDDESTSKTMHLMGDFSAPAEFFVT
LGIFSFFYTIAALVIYLRFHKLYTENRRFPLVDFCVTVSFTFFWLVAAAAWGKGLTDVKG
ATRPSSLTAAMSVCHGEEAVCSAGATPSMGLANISVLFGFINFFLWAGNCWFVFKETPWH
GQGQDQGQGTSPESAAEQGAVEKQ
aa 1-264 Synaptophysin domain
aa 30-238 MARVEL domain (SEQ ID NO. 6) Q7ZWV8_XENLA Mg29-prov protein [syp12] [*Xenopus laevis* (African clawed frog)] 251 AA
Score = 312 bits (800), Expect = 2e-83
Identities = 153/247 (61%), Positives = 184/247 (74%), Gaps = 16/247 (6%)
MDRLGGLAGLGKKNPFAGLRWRRLEEPLGFIKLLEWLFAIFAFGSCGSYSGETAATVMCK
SEADTEIKLISVPFGYPFRLYRQRYEMPACDDMERRILHLTGDFSAPAEFFVTMGVFAFL
YAMFALVIYLRFHEEYTKIRRLPIVDLCVTGAFTFLWLVAASAWGKGLMDVKVATQPSSL
VSSMPLCQMEKATCNAGSSPYFALANISVLFGFLNFIIWAANIWFVFKETTWSKKPASKE
ESAERGEVEDH
aa 13-244 Synaptophysin domain
aa 23-231 MARVEL domain (SEQ ID NO. 7) Q6DF52_XENTR Synaptophysin-like 2 [syp12] [*Xenopus tropicalis* (Western clawed frog) (*Silurana tropicalis*)] 254 AA
Score = 297 bits (761), Expect = 7e-79
Identities = 147/251 (58%), Positives = 179/251 (71%), Gaps = 18/251 (7%)
MDREGGLAGLGKKNPLAGLRWRRLEEPLGFIKLLEWLFAIFAFGCCGSYSGETAATVMCK
TETDSDTEIKLISVPFAYPFRLYRQRYEMPACEDIERRILHLTGDFSAPAEFFVTMGVFA
FLYSMFALVVYLRFHEEYTKIRRVPIVDLCVTGAFAFLWLVAASAWGKGLMDVKVATQPS
NLVSSMPLCQMEKATCNAGSQPYFALANISVLFGFLNFLIWAANVWFVFKETTLSNKPAS
KEESAERGEVEDHQ
aa 13-246 Synaptophysin domain
aa 23-233 MARVEL domain (SEQ ID NO. 8) Q90661_CHICK Synaptophysin IIa [*Gallus gallus* (Chicken)] 268 AA
Score = 220 bits (560), Expect = 1e-55
Identities = 103/197 (52%), Positives = 134/197 (68%), Gaps = 1/197 (0%)
MCMVIFAPLFAIFAFATCGGYSGGLRLSVDCANKSESDLNIDIAFAYPFRLHQVNFDAPT
CEGKRRETLSLIGDFSSSAEFFVTIAVFAFLYSLAATVVYIFFQNKYRENNRGPLIDFIV
TVVFSFLWLVGSSAWAKGLSDVKIATDPPDEVLLLMSACKQQSNKCLPVRSPVMSSLNTSV
VFGFLNFILWAGNIWFVFKETGWHSSGQRHAADTMEKQSSGYNQGGYNQDSYGPAGGYNQ
PGSYGQVGDYGQPQSYGQSGPTSFANQI
aa 1-268 Synaptophysin domain
aa 2-202 MARVEL domain (SEQ ID NO. 9) Q8TBG9_SYNPR_HUMAN Synaptoporin [SYNPR] [*Homo sapiens* (Human)] 265 AA
Score = 218 bits (555), Expect = 5e-55
Identities = 104/197 (52%), Positives = 133/197 (67%), Gaps = 1/197 (0%)
MCMVIFAPLFAIFAFATCGGYSGGLRLSVDCVNKTESNLSIDIAFAYPFRLHQVTFEVPT
CEGKERQKLALIGDSSSSAEFFVTVAVFAFLYSLAATVVYIFFQNKYRENNRGPLIDFIV
TVVFSFLWLVGSSAWAKGLSDVKVATDPKEVLLLMSACKQPSNKCMAIHSPVMSSLNTSV
VFGFLNFILWAGNIWFVFKETGWHSSGQRYLSDPMEKHSSSYNQGGYNQDSYGSSSGYSQ
QASLGPTSDEFGQQPTGPTSFTNQI
aa 1-265 Synaptophysin domain
aa 1-202 MARVEL domain
aa 33, 38 N-linked Glycosylation (SEQ ID NO. 10) B3KVD8_HUMAN cDNA FLJ16439 fis, clone BRAMY2046109, highly similar to Synaptoporin [*Homo sapiens* (Human)] 276 AA
Score = 218 bits (555), Expect = 5e-55
Identities = 104/197 (52%), Positives = 133/197 (67%), Gaps = 1/197 (0%)
MCMVIFAPHNEECKSHFHLLFAIFAFATCGGYSGGLRLSVDCVNKTESNLSIDIAFAYPF
RLHQVTFEVPTCEGKERQKLALIGDSSSSAEFFVTVAVFAFLYSLAATVVYIFFQNKYRE
NNRGPLIDFIVTVVFSFLWLVGSSAWAKGLSDVKVATDPKEVLLLMSACKQPSNKCMAIH
SPVMSSLNTSVVFGFLNFILWAGNIWFVFKETGWHSSGQRYLSDPMEKHSSSYNQGGYNQ
DSYGSSSGYSQQASLGPTSDEFGQQPTGPTSFTNQI

TABLE 1-continued

UniProtKB/Swiss-Prot MG29 Gene/Protein Structural Homology Data

|  |  |
|---|---|
|  | aa 20-276 Synaptophysin domain |
|  | aa 5-213 MARVEL domain |
|  | aa 33, 38 N-linked Glycosylation |
| Nucleic acid Accession Nos., incorporated herein by reference. | NM_001006110 (*Xenopus* (*Silurana*) *tropicalis* synaptophysin-like 2 (syp12), mRNA) (SEQ ID NO. 20)<br>NM_001040709 (*Homo sapiens* synaptophysin-like 2 (SYPL2), mRNA)(SEQ ID NO. 21)<br>BC113102 (*Homo sapiens* synaptophysin-like 2, mRNA (cDNA clone MGC: 135026 IMAGE: 40077145), complete cds)(SEQ ID NO. 22)<br>NM_001108563 (*Rattus norvegicus* synaptophysin-like 2 (Syp12), mRNA)(SEQ ID NO. 23)<br>NM_008596 (*Mus musculus* synaptophysin-like 2 (Syp12), mRNA)(SEQ ID NO. 24)<br>NM_001086184 (*Xenopus laevis* mitsugumin 29 (mg29), mRNA)(SEQ ID NO. 25) |

TABLE 2

CLUSTAL W (1.82) multiple sequence alignment of MG29 homologs

```
Q7ZWV8_XENLA      MDRLGGLAGLGKKNP-------FAGLRWRRLEEPLGFIKLLEWLFAIFAFGSCGSYSGET

Q6DF52_XENTR      MDREGGLAGLGKKNP-------LAGLRWRRLEEPLGFIKLLEWLFAIFAFGCCGSYSGET

SYPL2_MOUSE       MSSTESPGRTSDKSPRQQVDRLLLGLRWQRLEEPLGFIKVLQWLFAIFAFGSCGSYSGET

SYPL2_RABIT       MSSTESPSRAADKSPRQQVDRLLEGLRWRRLEEPLGFIKVLQWLFAIFAFGSCGSYSGET

Q0VBZ3_BOVIN      MSSTESSSRTADKSPRQQVDRLLVGLRWRRLEEPLGFIKVLQWLFAIFAFGSCGSYSGET

SYPL2_HUMAN       MSSTESAGRTADKSPRQQVDRLLVGLRWRRLEEPLGFIKVLQWLFAIFAFGSCGSYSGET

Q5VXT5-2_HUMAN    MSSTESAGRTADKSPRQQVDRLLVGLRWRRLEEPLGFIKVLQWLFAIFAFGSCGSYSGET

Q90661_CHICK      ----------------------------------MCMVIFAPLFAIFAFATCGGYSGGL
                                                    : ::  *******. **.***

Q7ZWV8_XENLA      AATVMCKSEAD--TEIKLISVPFGYPFRLYRQRYEMPACDDMER-RILHLTGDFSAPAEF

Q6DF52_XENTR      AATVMCKTETDSDTEIKLISVPFAYPFRLYRQRYEMPACEDIER-RILHLTGDFSAPAEF

SYPL2_MOUSE       GALVLCNNEAK---DVSSIIVLFGYPFRLYQVQYEMPLCDQDSTSKTMNLMGDFSAPAEF

SYPL2_RABIT       GAMVRCNNEAK---DVSSIIVLFGYPFRLHRIEYEMPLCDDDSSSKTMHLMGDFSAPAEF

Q0VBZ3_BOVIN      GATVRCNNEAK---DVSAIIVSFGYPFRLNRVQYEMPLCDDESTSKTMHLMGDFSAPAEF

SYPL2_HUMAN       GAMVRCNNEAK---DVSSIIVAFGYPFRLHRIQYEMPLCDEESSSKTMHLMGDFSAPAEF

Q5VXT5-2_HUMAN    GAMVRCNNEAK---DVSSIIVAFGYPFRLHRIQYEMPLCDEESSSKTMHLMGDFSAPAEF

Q90661_CHICK      RLSVDCANKSE---SDLNIDIAFAYPFRLHQVNFDAPTCEG-KRRETLSLIGDFSSSAEF
                   * * .::.   .  *  : *.***** : .:: * *:  .  . : * ****:.***

Q7ZWV8_XENLA      FVTMGVFAFLYAMFALVIYLRFHEEYTKIRRLPIVDLCVTGAFTFLWLVAASAWGKGLMD

Q6DF52_XENTR      FVTMGVFAFLYSMFALVVYLRFHEEYTKIRRVPIVDLCVTGAFAFLWLVAASAWGKGLMD

SYPL2_MOUSE       FVTLGIFSFFYTMAALVIYLRFHKLYTENKRFPLVDFCVTVSFTFFWLVAAAAWGKGLTD

SYPL2_RABIT       FVTLGIFSFFYTMAALVVYLRFHKLYTENKRFPLVDFCVTVSFTFFWLVAAAAWGKGLTD

Q0VBZ3_BOVIN      FVTLGIFSFFYTIAALVIYLRFHKLYTENRRFPLVDFCVTVSFTFFWLVAAAAWGKGLTD

SYPL2_HUMAN       FVTLGIFSFFYTMAALVIYLRFHNLYTENKRFPLVDFCVTVSFTFFWLVAAAAWGKGLTD

Q5VXT5-2_HUMAN    FVTLGIFSFFYTMAALVIYLRFHNLYTENKRFPLVDFCVTVSFTFFWLVAAAAWGKGLTD

Q90661_CHICK      FVTIAVFAFLYSLAATVVYIFFQNKYRENNRGPLIDFIVTVVFSFLWLVGSSAWAKGLSD
                  ***:..:*:*:*:.:  *  *:*: *:: *  .* *:*:*  ** .:**.*** *
```

TABLE 2-continued

CLUSTAL W (1.82) multiple sequence alignment of MG29 homologs

```
Q7ZWV8_XENLA      VKVATQPSSLVSSMPLCQMEKATCNAGSSPYFALANISVLFGFLNFIIWAANIWFVFKET

Q6DF52_XENTR      VKVATQPSNLVSSMPLCQMEKATCNAGSQPYFALANISVLFGFLNFLIWAANVWFVFKET

SYPL2_MOUSE       VKGATRPSSLTAAMSVCHGEEAVCSAGATPSMGLANLSVLFGFINFFLWAGNCWFVFKET

SYPL2_RABIT       VKGATRPSSLTAAMSVCHGEEAVCSAGATPSMGLANISVLFGFINFFLWAGNCWFVFKET

Q0VBZ3_BOVIN      VKGATRPSSLTAAMSVCHGEEAVCSAGATPSMGLANISVLFGFINFFLWAGNCWFVFKET

SYPL2_HUMAN       VKGATRPSSLTAAMSVCHGEEAVCSAGATPSMGLANISVLFGFINFFLWAGNCWFVFKET

Q5VXT5-2_HUMAN    VKGATRPSSLTAAMSVCHGEEAVCSAGATPSMGLANISVVR-------------------

Q90661_CHICK      VKIATDPDEVLLLMSACKQQSNKCLPVRSPVMSSLNTSVVFGFLNFILWAGNIWFVFKET
                  ** ** *..:    *. *: :. * .   * :.  * **:

Q7ZWV8_XENLA      TWS--------------------------------KKPASKEESAERGEVEDH-----

Q6DF52_XENTR      TLS--------------------------------NKPASKEESAERGEVEDHQ----

SYPL2_MOUSE       PWHGQGQ-------------------------DQGQGPSQESAAEQGAVEKQ-----

SYPL2_RABIT       PWHGQGQ-------------------------DQGQGPSQESAAEQGAVEKQ-----

Q0VBZ3_BOVIN      PWHGQGQ-------------------------DQGQGTSPESAAEQGAVEKQ-----

SYPL2_HUMAN       PWHGQGQGQDQDQDQ------------------DQGQGPSQESAAEQGAVEKQ-----

Q5VXT5-2_HUMAN    --------------------------------PVATAGSSTSPAAQACPS-------

Q90661_CHICK      GWHSSGQRHAADTMEKQSSGYNQGGYNQDSYGPAGGYNQPGSYGQVGDYGQPQSYGQSGP
                                                  *    .  .  .

Q7ZWV8_XENLA      -------                                        (SEQ ID NO: 6)

Q6DF52_XENTR      -------                                        (SEQ ID NO: 7)

SYPL2_MOUSE       -------                                        (SEQ ID NO: 1)

SYPL2_RABIT       -------                                        (SEQ ID NO: 2)

Q0VBZ3_BOVIN      -------                                        (SEQ ID NO: 5)

SYPL2_HUMAN       -------                                        (SEQ ID NO: 3)

Q5VXT5-2_HUMAN    -------                                        (SEQ ID NO: 4)

Q90661_CHICK      TSFANQI                                        (SEQ ID NO: 8)
```

Recombinant polypeptides provided by the invention may also comprise a fusion protein domain, and/or an amino acid linking sequences inserted between polypeptide domains, which allows, for example, for steric flexibility and/or comprises consensus sequence for enzymatic modification (e.g., phosphorylation, protease cleavage, ubiquination, or the like). The recombinant polypeptides can be constructed using standard molecular biological techniques for manipulation of DNA sequences; some of which are described herein.

In additional aspects, the invention relates to diagnostic oligonucleotides and diagnostic oligonucleotide set(s) or libraries. For example, in an embodiment of this aspect, the diagnostic oligo library comprises a plurality of oligonucleotide probes capable of hybridizing to an MG29 gene or transcript, wherein a correlation exists between the health status of an individual, and the individual's expression of MG29 RNA corresponding to the oligonucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In any of the embodiments described herein, a nucleic acid provided by the invention can be amplified and/or expressed in a host cell such as a prokaryotic, e.g., a bacteria cell, or eukaryotic cell, e.g., a mammalian cell, using a suitable vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In certain embodiments, the nucleic acids provided by the invention are expressed in an inducible and/or tissue-specific manner. For example, a recombinant mammalian expression vector is capable of directing expression of the nucleic acid preferentially in a particular cell type (e.g., tissue-specific regulatory elements are used to express the nucleic acid). Tissue-specific regulatory elements are known in the art.

Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The nucleic acid molecules provided by the invention can also be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci*. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

In any of the embodiments described herein, the nucleic acids encoding an MG29 can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, Maltose Binding Protein (MBP)-Tag, fluorescent protein, GST, TAT, an antibody portion, a signal peptide, and the like, at the 5' end, the 3' end, or at any location within the ORF.

In an additional aspect, the invention provides antisense and/or interfering nucleic acids (e.g., RNAi) capable of specifically targeting MG29 nucleic acids (e.g., SEQ ID NOs: 20-25). For example, the present invention features a nucleic acid molecule, such as a decoy RNA, dsRNA, siRNA, shRNA, microRNA, aptamer, and/or antisense nucleic acid molecules, which down regulates expression of a sequence encoding an MG29 proteins. In another embodiment, a nucleic acid molecule of the invention has an endonuclease activity or is a component of a nuclease complex, and cleaves RNA having an MG29 nucleic acid sequence.

In any of the interfering nucleic acid embodiments, the nucleic acid molecule comprises between 12 and 100 bases complementary to an RNA having an MG29 nucleic acid sequence. In another embodiment, the nucleic acid molecule comprises between 14 and 24 bases complementary to an RNA having an MG29 nucleic acid sequence. In any embodiment described herein, the nucleic acid molecule can be synthesized chemically according to methods well known in the art. A number of references describe useful methods and approaches for generating RNAs including: 6900187, 6383808, 7101991, 7285541, 7368436, 7022828; which are incorporated herein by reference.

In another embodiment, the invention provides a composition comprising a pharmaceutically acceptable carrier or excipient and an effective amount of at least one member selected from the group consisting of at least one MG29 polypeptide as set forth in SEQ ID NOs: 1-8 or 26; at least one inhibitory nucleic acid that hybridizes to at least a portion of: (i) a nucleic acid that encodes an MG29 polypeptide, (ii) the 3' UTR of a nucleic acid that encodes an MG29 polypeptide, (ii) the 5' UTR of a nucleic acid that encodes an MG29 polypeptide, or (iv) a nucleic acid that encodes a post-translational modulator of MG29 expression, and modulates MG29 expression and/or protein activity. In certain embodiments the inhibitory nucleic acid comprises RNA. In another embodiment, the inhibitory nucleic acid is an RNA oligonucleotide having from 10 to 100 nucleotides, wherein the oligonucleotide hybridizes to at least a portion of (i) a nucleic acid that encodes an MG29 polypeptide, (ii) the 3' UTR of a nucleic acid that encodes an MG29 polypeptide, or (ii) the 5' UTR of a nucleic acid that encodes an MG29 polypeptide, and modulates MG29 expression and/or protein activity. In another embodiment, the inhibitory RNA is at least one of an antisense RNA, an interfering RNA or a combination of both. In yet another embodiment, the interfering RNA is at least one of a siRNA, a miRNA or a combination of both. In another aspect the invention provides a nucleic acid vector comprising any of the inhibitory nucleic acids described herein. In additional aspects, the invention provides a host cell comprising any of the inhibitory nucleic acids described herein and/or any of the vectors provided by the invention.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin, and/or an antisense molecule can bind such that the antisense molecule forms a loop or hairpin. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol, 40, 1-49, which are incorporated herein by reference in their entirety. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Long double-stranded RNAs (dsRNAs; typically >200 nt) can be used to silence the expression of target genes in a variety of organisms and cell types (e.g., worms, fruit flies, and plants). Upon introduction, the long dsRNAs enter a the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs and/or microRNAs (miRNA).

Injection and transfection of dsRNA into cells and organisms has been the main method of delivery of siRNA. And while the silencing effect lasts for several days and does appear to be transferred to daughter cells, it does eventually diminish. Recently, however, a number of groups have developed expression vectors to continually express siRNAs in transiently and stably transfected mammalian cells. (See, e.g., Brummelkamp T R, Bernards R, and Agami R. (2002). A system for stable expression of short interfering RNAs in mammalian cells. *Science* 296:550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052, which are herein incorporated by reference in their entirety).

Polypeptides

In additional aspects, and as described above, the invention also provides isolated and/or recombinant MG29 polypeptides.

Also included in the invention are substantially purified MG29 polypeptides having a sequence as set forth in SEQ ID NOs: 1-19 or a functional portion thereof. In certain embodiments, the MG29 polypeptides of the invention include an amino acid sequence that is substantially identical to the amino acid sequence of a human MG29 polypeptide (SEQ ID NO.: 3).

MG29 polypeptides have the ability to interact (e.g., bind non-covelently) and form complexes with itself as well as with a number other cellular proteins. In an embodiment of this aspect the invention comprises an isolated or recombinant MG29 polypeptide (e.g., SEQ ID NOs: 1-8, or 26), homolog, fragment, or derivative thereof. In an additional embodiment, the invention provides a complex comprising an MG29 polypeptide, in combination with at least one other polypeptide, wherein the combination forms a protein complex, and wherein the complex is capable of improving the glucose clearing function of skeletal muscle. The invention further comprises a method of treating or preventing a muscle-related pathology comprising administering to a cell an effective amount of an isolated and/or recombinant MG29 polypeptide, and/or an isolated and/or recombinant MG29 polypeptide in a protein complex with at least one other protein, wherein the complex is capable of improving the glucose clearing function of skeletal muscle. The polypeptides of the complex can be formed, for example, using a peptide synthesizer according to standard methods; or by expressing each polypeptide in a single cell; or separately in a cell or cell lysate system and then isolating and purifying the polypeptide.

In an additional aspect, the invention relates to compositions comprising a polypeptide of the invention in combination with at least one other agent, which is capable of modulating the glucose clearing function of skeletal muscle. In additional embodiments, therapeutics of the invention may comprise one or more biologically active ingredients such as, Analgesics, Antacids, Antianxiety Drugs, Antiarrhythmics, Antibacterials, Antibiotics, Anticoagulants and Thrombolytics, Anticonvulsants, Antidepressants, Antidiarrheals, Antiemetics, Antifungals, Antihistamines, Antihypertensives, Anti-Inflammatories, Antineoplastics, Antipsychotics, Antipyretics, Antivirals, Barbiturates, Beta-Blockers, Bronchodilators, Cold Cures, Corticosteroids, Cough Suppressants, Cytotoxics, Decongestants, Diuretics, Expectorants, Hormones, Hypoglycemics (Oral), Immunosuppressives, Laxatives, Muscle Relaxants, Sedatives, Sex Hormones, Sleeping Drugs, Tranquilizer, Vitamins or a combination thereof.

In another aspect, the compositions provided by the invention may include a pharmaceutically acceptable carrier. Certain embodiments of this aspect comprise therapeutic compositions comprising polypeptides of the invention, for example, MG29, in combination with a pharmaceutically acceptable carrier, wherein the therapeutic composition is administered systemically, and wherein the systemically administered composition is effective for the treatment and/or prevention of diabetes.

In an additional aspect, the invention provides fusion proteins comprising a "tag" or indicator portion and an MG29 portion. In certain aspects the tag or indicator portion can be a peptide adapted for purification purposes, for example, FLAG tag, 6×His tag, Maltose-Binding Protein (MBP) tag, or the like. In other aspects, the tag peptide comprises a peptide adapted for providing a signal such as an antibody epitope or a fluorescent peptide. Still other aspects include the fusion of the MG29 with a peptide that is adapted for mediating subcellular localization or translocation across a cellular membrane, for example, a TAT fusion protein from the HIV virus To facilitate cell penetration or a modified cellular localization tag to couple MG29 to particular cellular organelles.

The molecules of the instant invention can be used as pharmaceutical agents to prevent, inhibit, ameliorate, and/or treat a disease state in a subject. A number of useful nucleic acid-based therapeutic approaches are known and discussed in Patil et al., *AAPS Journal*, 2005; 7(1):E61-77, which is incorporated by reference in its entirety.

The nucleic acid molecules of the instant invention, individually, or in combination or in conjunction with other drugs, can be used to treat diseases or conditions discussed above. For example, the subject can be treated, or other appropriate cells can be treated, as is evident to those skilled in the art, individually or in combination with one or more drugs under conditions suitable for the treatment.

In another aspect, the invention provides pharmaceutical compositions that include therapeutically- or prophylactically-effective amounts of a therapeutic and a pharmaceutically-acceptable carrier that are effective for the treatment or prevention of a muscle related disease, including diabetes, in an individual. The molecules of the instant invention can be used as pharmaceutical agents to prevent, inhibit, ameliorate, and/or treat a disease state in a subject.

In certain embodiments the therapeutic comprises a nucleic acid of the invention, e.g., a MG29 nucleic acid, for example, at least one of SEQ ID NOs: 20-15. In additional embodiments, the therapeutic nucleic acid provided by the invention is a peptide nucleic acid, a cDNA, or RNA, such as for example, a small inhibitory RNA. A number of useful nucleic acid-based therapeutic approaches are known and discussed in Patil et al., *AAPS Journal*, 2005; 7(1):E61-77, which is incorporated by reference in its entirety.

In additional embodiments, the therapeutic provided by the invention is a composition comprising an MG29 polypeptide, for example, at least one of SEQ ID NOs.: 1-8, or 26 or a bioactive portion thereof; or an antibody specific for a MG29 polypeptide. In a further aspect, the invention includes, in one or more containers, a therapeutically- or prophylactically-effective amount of this pharmaceutical composition. Also included in the invention is an oligonucleotide, e.g., an oligonucleotide which includes at least 6 contiguous nucleotides of an MG29 nucleic acid or a complement of said oligonucleotide.

In certain embodiments, the nucleic acid molecules provided by the invention are modified to enhance stability with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163). While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules. Accordingly, nucleic acid molecules having chemical modifications that maintain or enhance activity are provided. Such a nucleic acid is also generally more resistant to nucleases than unmodified nucleic acid. Nucleic acid molecules are preferably resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

In one embodiment, the invention provides a modified nucleic acid molecule comprising a phosphate backbone modification comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols. Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle. The amount of active ingredient that can be combined with the carrier materials to produce a single dosage form varies depending upon the host treated and the particular mode of administration. Dosage unit forms generally contain between from about 1 mg to about 5000 mg of an active ingredient. It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

Alternatively, certain of the nucleic acid molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; Dropulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In another aspect, the invention provides an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule. In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another embodiment, an isolated nucleic acid molecule of the invention comprises a nucleic acid molecule that is a complement of the nucleotide sequence of an MG29 nucleic acid.

Applications

In additional aspects the invention relates to compositions and methods related to the treatment of muscle-related pathologies and conditions, including diabetes. In certain exemplary embodiments, the invention encompasses, for example, the administration of an effective amount of a therapeutic composition of the invention to an individual for the treatment and/or prevention of diabetes.

Also within the scope of the invention is the use of a therapeutic of the invention in the manufacture of a medicament for treating or preventing muscle-related pathologies or conditions, disorders or syndromes including, e.g., muscle fatigue or atrophy, cardiovascular disease, cardiomyopathy, diabetes mellitus, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, oxidative damage, muscle weakness, muscle atrophy, heart failure, secondary pathologies caused by heart failure and hypertension, hypotension, angina pectoris, myocardial infarction, heart attacks, heart failure, diabetic ulcers, renal artery stenosis, interstitial nephritis, glomerulonephritis, polycystic kidney disease, systemic, renal tubular acidosis, IgA nephropathy, nephrological diseases, hypercalcemia, muscle disorders, urinary retention, neuroprotection, Stroke, Aphakia, neurodegenerative disorders, neurologic disorders, and/or other pathologies and disorders of the like.

By way of non-limiting example, the compositions of the present invention will have efficacy for treatment of patients suffering from the diseases and disorders disclosed above and/or other pathologies and disorders of the like, in particular, diabetes. In certain aspects, the polypeptides provided by the invention are used as immunogens to produce antibodies specific for the invention, and as vaccines, and/or used to screen for potential agonist and antagonist compounds. In addition, a cDNAs encoding synaptophysin-like proteins of the invention, for example, MG29, are provided for use in gene therapy methods to be administered to a subject in need thereof.

In certain aspects, the invention provides compositions and methods for modulating muscle function comprising modulating the transcription, translation (i.e., expression), and/or activity of MG29. As described herein, in one exemplary embodiment modulation of MG29 is accomplished by, for example, the administration of nucleic acids complementary to MG29 nucleic acids, and/or MG29 polypeptide binding partners, i.e., modulation of factors that bind to MG29 nucleic acids and/or MG29 polypeptides, and inhibit, attenuate or neutralize their biological activities, such as at least one MG29 RNA binding protein, for example, HuR, ARE, and/or LOX-DICE; and/or at least one MG29 gene transcription factor, for example, GATA, RUNX1, SREBP1, C/EBP, and/or p300; using inhibitory RNAs, antibodies, pseudopeptides, peptide analogs or peptidomimetics, or small molecules that bind and inhibit one or more target nucleic aids or polypeptides. In one embodiment the invention relates to a method for treating or preventing diabetes in an individual comprising upregulating the transcription, and/or translation of an MG29 gene, and/or the activity of an MG29 polypeptide. In another embodiment, inhibition or down-regulation of MG29 genes with the nucleic acid molecule of the instant invention is greater in the presence of the nucleic acid molecule than in its absence.

In an addition embodiment, the invention provides a method for modulating glucose uptake in a cell, comprising administering to a muscle cell a composition comprising an effective amount of an agent that modulates the expression of an MG29 gene, or modulates the activity of an MG29 polypeptide or both, wherein the modulation of MG29 results in the modulation of glucose uptake in the cell. In certain embodiments, the cell is a muscle cell, for example, a skeletal muscle cell, a cardiac muscle cell, or a smooth muscle cell. In additional embodiments, the composition further comprises a pharmaceutically acceptable carrier or excipient as described herein. In certain additional embodiments, the agent comprises a nucleic acid encoding a polypeptide having at least 85% sequence identity to an MG29 polypeptide selected from the group consisting of SEQ ID NOs.: 1-8, and 26. In a preferred embodiment, the nucleic acid encodes an MG29 polypeptide as set forth in SEQ ID NO:3. In an alternative embodiment, the agent comprises at least one inhibitory nucleic acid that hybridizes to a member selected from the group consisting of a nucleic acid that encodes an MG29 polypeptide, an UTR of a nucleic acid that encodes an MG29 polypeptide, and a nucleic acid that encodes a modulator of MG29 gene expression. In certain embodiments, the inhibitory nucleic acid is RNA. In still another embodiment, the inhibitory RNA hybridizes to an UTR of a nucleic acid that encodes an MG29 polypeptide as set forth in at least one of SEQ ID NOs: 20-25, or a nucleic acid that encodes a modulator of MG29 expression In another embodiment, the inhibitory RNA is at least one of an antisense RNA, an interfering RNA or a combination of both. In a preferred embodiment, the interfering RNA is at least one of an siRNA, an miRNA or a combination of both.

In additional aspects, the invention provides methods of administering to an individual an effective amount of a nucleic acid encoding an MG29 polypeptide, for example, MG29, homologs, fragments, and derivatives thereof, for the treatment and/or prevention of a muscle related pathology or condition, for example, diabetes. As demonstrated herein, the MG29 polypeptides of the invention are capable of regulating a variety of processes in muscle and muscle cells, and can provide an effective therapeutic approach against a number of disorders that involve compromised muscle function. In one embodiment, the invention provides a method of treating and/or preventing diabetes comprising the steps of administering to an individual composition comprising an effective amount of a nucleic acid or polypeptide of the invention in combination with a pharmaceutically acceptable excipients, wherein the composition is effective in treating and/or preventing diabetes.

In additional aspects, the invention provides methods of modulating the expression of an MG29 gene, e.g., SEQ ID NOs.: 20-15, or the activity of MG29 protein, e.g., SEQ ID NOs.: 1-8, and 26. In certain embodiments, the method comprises administering a recombinant nucleic acid encoding an MG29 polypeptide to a cell or tissue, in vitro, ex vivo, or in vivo, wherein the recombinant nucleic acid is effective in modulating at least one of the expression or activity of MG29. In any of the embodiments described herein, the recombinant MG29 nucleic acid may be cistronic; i.e., comprise the desired coding sequence within a sing open reading frame (ORF); or it may contain one or more intronic sequences. In certain other embodiments, the method comprises administering a recombinant nucleic acid that is capable of hybridizing specifically to a nucleic acid that encodes an MG29 polypeptide, to a cell or tissue, in vitro, ex vivo, or in vivo. In certain embodiments, the recombinant MG29 nucleic acid is incorporated into a nucleic acid vector, for example, a plasmid, viral vector, artificial chromosome or the like. In additional embodiments, the vector comprising a recombinant MG29 nucleic acid contains one or more transcription or replication regulatory elements, selectable markers or translation modifying sequences operably linked to the MG29 nucleic acid.

In an additional aspect, the invention provides a method of treating diabetes comprising administering to an individual a composition comprising an effective amount of an agent that performs at least one of: increasing the expression of an MG29 gene, increasing the activity of an MG29 polypeptide, or a combination of both, wherein the agent is effective for the treatment of diabetes. In certain embodiments, the composition is administered systemically. In certain additional embodiments, the agent comprises a nucleic acid encoding a polypeptide having at least 85% sequence identity to an MG29 polypeptide selected from the group consisting of SEQ ID NOs.: 1-8, and 26. In a preferred embodiment, the nucleic acid encodes an MG29 polypeptide as set forth in SEQ ID NO:3. In an alternative embodiment, the agent comprises at least one inhibitory nucleic acid that hybridizes to a member selected from the group consisting of a nucleic acid that encodes an MG29 polypeptide, an UTR of a nucleic acid that encodes an MG29 polypeptide, and a nucleic acid that encodes a modulator of MG29 expression. In certain embodiments, the inhibitory nucleic acid is RNA. In still another embodiment, the inhibitory RNA hybridizes to an UTR of a nucleic acid that encodes an MG29 polypeptide as set forth in at least one of SEQ ID NOs: 20-25, or a nucleic acid that encodes a modulator of MG29 gene expression. In another embodiment, the inhibitory RNA is at least one of an antisense RNA, an interfering RNA or a combination of both. In any of the embodiments described herein, the interfering RNA provided by the invention is at least one of an siRNA, an miRNA or a combination of both.

In any of the methods described herein, the nucleic acids or polypeptides of the invention may be delivered or administered in any pharmaceutically acceptable form, and in any pharmaceutically acceptable route as described in further detail below. For example, compositions comprising nucleic acids and/or polypeptides of the invention can be delivered systemically or administered directly to a cell or tissue. In certain additional embodiments, the nucleic acids and/or polypeptides of the invention comprise a carrier moiety that improves bioavailability, increases the drug half-life, targets the therapeutic to a particular cell or tissue type, for example, skeletal or striated muscle cells or tissues, or combinations thereof.

In yet another aspect, the invention provides a method for determining the presence of or predisposition to a disease associated with a muscle-related pathology or muscle dysfunction in a subject (e.g., a human subject). In one embodiment, the method comprises isolating a biological sample from an individual (e.g., blood, muscle, or other), detecting the genotype of an MG29 gene by treating a tissue sample from an individual with a detectable probe specific for an MG29 polymorphism or mutation, and detecting the formation of a probe/target complex, wherein formation of a complex is indicative of the presence of a particular genotype. Alternatively, measuring the amount of MG29 nucleic acid or polypeptide in a test sample from the subject and comparing the amount of the polypeptide in the test sample to the amount of MG29 nucleic acid or polypeptide present in a control sample. An alteration in the level in the test sample as compared to the control sample indicates the presence of or predisposition to a disease in the subject. Preferably, the predisposition includes, for example, diabetes. Also, the expression levels of the new polypeptides of the invention can be used in a method to screen for diabetes as well as to determine the type or degree of the disease. In another embodiment, the method comprises steps for diagnosing or monitoring disorder or disease or progression comprising isolating a biological sample from an individual, detecting for the presence of a nucleotide polymorphism in an MG29 gene as described herein, wherein the MG29 polymorphism is associated with the disease or its severity.

In an embodiment, the invention comprises a method for screening for agents that modulate at least one of MG29 activity, protein levels, or gene expression (i.e., an MG29 agonist and/or antagonist) comprising providing a cell or tissue; measuring for the amount of at least one of endogenous MG29 activity, protein level, or gene expression to establish a control value; contacting a test agent to the cell or tissue; measuring or detecting the activity of at least one of MG29, amount of MG29 protein, or amount of MG29 gene expression to establish a test value; and comparing the control value to the test value, wherein an observed change between the test and control values indicates an agent capable of modulating at least one of MG29 activity, protein levels, or gene expression in the cell or tissue.

In another embodiment, the invention provides a method for screening for a modulator of disorders or syndromes including, for example, diabetes. The method comprises the steps of contacting a test agent with an MG29 nucleic acid or polypeptide, and determining if the test compound binds to said MG29 nucleic acid or polypeptide. Binding of the test compound to the MG29 nucleic acid or polypeptide indicates the test compound is a modulator of activity, transcription, translation or of latency or predisposition to the aforementioned disorders or syndromes. In another embodiment, the invention provides a method for screening for agents that modulate muscle glucose clearing comprising contacting a muscle that expresses MG29 with an agent that modulates the expression and/or activity of MG29 or MG29 interacting protein or a combination thereof, and measuring the effects on the glucose clearing function of skeletal muscle, wherein an increase in glucose clearing is indicative of an MG29 agonist and a decrease in glucose clearing is indicative of an MG29 antagonist.

Libraries of potential compounds are widely known and readily available that could be used in the methods of the invention. Furthermore, the techniques useful for measuring the binding of agents to MG29 polypeptides, the amount of MG29 protein, and/or the level of MG29 gene transcription and/or translation are described herein. Additional methods useful for practicing the invention are routinely used and can be adapted for use in the claimed methods using routine experimentation for the art.

In another aspect, the invention provides a method of detecting the presence of an MG29 nucleic acid or polypeptide in a sample, the method comprising the steps of isolating a biological sample, contacting the sample with a detectable agent (e.g., nucleic acid probe, an antibody or small molecule) that selectively binds to the target nucleic acid or polypeptide, respectively, under conditions allowing for formation of a complex between the agent and the nucleic acid or polypeptide. The complex is then detected, if present, thereby identifying the MG29 nucleic acid or polypeptide, within the sample. The methods of invention can also be used to identify specific cell or tissue types based on their expression of an MG29 nucleic acid or polypeptide.

In a further aspect, the invention provides a method of producing a polypeptide comprising expressing, in a host cell or cell-free system, a nucleic acid encoding an MG29 polypeptide. In certain embodiments the MG29 nucleic acid is an endogenous MG29 gene. In additional embodiments, the MG29 nucleic acid is an exogenous MG29 nucleic acid. If desired, the polypeptide can then be recovered. For example, in certain embodiments, the MG29 nucleic acid to be expressed contains a leader or signal sequence directing its secretion into the surrounding media. Subsequently, the MG29 polypeptides can be isolated and purified from the media according to known methods. In additional embodiments, the invention includes a method of producing a polypeptide by culturing a cell that contains an endogenous nucleic acid encoding an MG29 nucleic acid, disposed upstream or downstream of an exogenous regulatory element, for example, a promoter, enhancer or repressor sequence. In certain embodiments, the exogenous regulatory element is incorporated into a host cell's genome through homologous recombination, strand break or mismatch repair mechanisms which are widely known in the art.

In a further aspect, the invention provides a method for modulating the activity or expression of an MG29 polypeptide, by contacting a cell sample that includes the MG29 polypeptide with a compound that binds to the MG29 polypeptide, an MG29 RNA binding protein, and/or an MG29 protein interactor in an amount sufficient to modulate the activity of said polypeptide, wherein the modulation of MG29 is effective for the treatment or prevention of diabetes or condition related thereto. The compound can be, e.g., a small molecule, such as a nucleic acid, peptide, polypeptide, peptidomimetic, carbohydrate, lipid or other organic (carbon containing) or inorganic molecule, as further described herein.

In another aspect, the invention provides a method for diagnosing diabetes in an individual comprising isolating a muscle cell from a normal subject and measuring the frequency of calcium sparks in the muscle cell to determine a basis for comparison; isolating a muscle cell from a test subject and measuring the frequency of calcium sparks in the test subject muscle cell, wherein a reduction in the frequency of the calcium sparks in the test individual is indicative of the existence and/or severity of a diabetic pathology.

Certain aspects of the invention encompass methods of detecting gene expression or polymorphisms with one or more DNA molecules wherein the one or more DNA molecules has a nucleotide sequence which detects expression of a gene corresponding to the oligonucleotides depicted in the Sequence Listing (See TABLES 1 and 2). In one format, the oligonucleotide detects expression of a gene that is differentially expressed. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression or polymorphisms. Such sequences may be predictive of a disease state. Polymorphisms have been identified that correlate with disease severity. (See, Zhong et al., Simultaneous detection of microsatellite repeats and SNPs in the macrophage migration inhibitory factor gene by thin-film biosensor chips and application to rural field studies. *Nucleic Acids Res.* 2005 Aug. 2; 33(13):e121; Donn et al., A functional promoter haplotype of macrophage migration inhibitory factor is linked and associated with juvenile idiopathic arthritis. *Arthritis Rheum.* 2004 May; 50(5):1604-10; all of which are incorporated herein by reference in their entirety for all purposes). As one of ordinary skill will comprehend, the MG29 gene polymorphisms associated with muscle disorders, and hence useful as diagnostic markers according to the methods of the invention, may appear in any of the nucleic acid regions of the MG29 gene or regulatory regions. Techniques for the identification and monitoring of polymorphisms are known in the art and are discussed in detail in U.S. Pat. No. 6,905,827 to Wohlgemuth, which is incorporated herein by reference in its entirety for all purposes.

Host Cells

As used in herein "cell" is used in its usual biological sense, and does not refer to an entire multicellular organism. The cell can, for example, be in vivo, in vitro or ex vivo, e.g., in cell culture, or present in a multicellular organism, including, e.g., birds, plants and mammals such as primates, humans, cows, sheep, apes, monkeys, swine, dogs, mice, rats, and cats. The cell can be prokaryotic (e.g., bacterial cell) or eukaryotic (e.g., mammalian or plant cell). The term "host cell" includes a cell that might be used to carry a heterologous or exogenous nucleic acid, or expresses a peptide or protein encoded by a heterologous or exogenous (i.e., foreign) nucleic acid. A host cell can contain genes that are not found within the native (non-transformed) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the invention.

Transformation of a host cell with recombinant DNA may be carried out by conventional techniques as are well known to those skilled in the art. By "transformation" is meant a permanent or transient genetic change induced in a cell following introduction, modification, and/or extraction of nucleic acid material, for example, DNA or RNA.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., *Saccharomyces cerevisiae*) or may be a mammalian cell, including a human cell. For long-term, high-yield production of recombinant proteins, stable expression is preferred.

In another aspect, the invention encompasses a host cell comprising any MG29 nucleic acid of the invention. In certain embodiments, the host cell comprises a vector that contains a recombinant MG 29 nucleic acid; or a nucleic acid complementary to an MG29 encoding nucleic acid; or an exogenous or recombinant promoter modulating expression of endogenous MG29 gene.

In another aspect, the invention encompasses transgenic organisms, for example, a mouse, which contains at least one recombinant MG29 allele, including a loss of function allele; or comprising an MG29 transgene; or comprising a vector containing a recombinant MG29 nucleic acid; or comprising an MG29 nucleic acid or nucleic acid precursor that is complementary to an MG29 encoding nucleic acid or portion thereof. In certain embodiments, the transgenic organism may comprise the recombinant MG29 nucleic acid operably linked to an inducible promoter/enhancer, and/or a tissue specific promoter, for example, a muscle specific promoter.

Kits

In another aspect the present invention provides a kit comprising a suitable container, a composition provided by the invention disposed therein, and instructions for its use. A further object of the present invention is to provide a kit comprising a suitable container, a therapeutic of the invention in a pharmaceutically acceptable form disposed therein, and instructions for its use.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

Antibodies

The invention also features antibodies that immunoselectively-bind to MG29, polypeptides, fragments, homologs, analogs, pseudopeptides, peptidomimetics or derivatives thereof. As such, in other embodiments, the invention pertains to isolated nucleic acid molecules that encode MG29 polypeptide binding proteins, antibody polypeptides, or biologically active portions thereof.

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')$_2$ fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of MG29, and/or MG29 receptor protein, variants, portions and/or combinations thereof. In alternative embodiments antibodies of the invention may target and interfere with the MG29/Glut4 interaction.

The preparation of monoclonal antibodies is well known in the art; see for example, Harlow et al., Antibodies: A Laboratory Manual, page 726 (Cold Spring Harbor Pub. 1988), U.S. Pat. Nos. 6,331,415 to Cabilly; 6,407,213 and 6,639,055 to Carter; 6,562,622; 6,693,176; 6,881,557; 5,807,715 to Morrison; 5,225,539 to Winter; 5,585,089, 5,693,761, 6,180,370, and 7,022,500 to Queen; 20070202105 to Doyle, all of which are incorporated herein by reference. Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind MG29 polypeptides or MG29 binding proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352: 624-628; Gram et al. (1992) PNAS 89:3576-3580. Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855). A therapeutically useful antibody to the components of the complex of the invention or the complex itself may be derived from a "humanized" or "superhumanized" monoclonal antibody. Humanized monoclonal antibodies are produced by transferring mouse complementarity determining regions (CDRs) from heavy and light variable chains of the mouse immunoglobulin into a human variable domain, then substituting human residues into the framework regions of the murine counterparts.

The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993; Wu T. T. and Kabat, E. A. (1970) J. Exp. Med., 132: 211-250; and Johnson G., Wu, T. T. and Kabat, E. A. (1995) In Paul, S. (ed.), Antibody Engineering Protocols. Humana Press, pp. 1-15, which are incorporated herein by reference. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of an MG29 polypeptide or MG29 binding protein, for example, Glut4, which is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci.* USA 78: 3824-3828; Kyte and Doolittle 1982, *J. Mol. Biol.* 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.,* 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology,* 10:779-783 (1992)); Lonberg et al. (*Nature,* 368: 856-859 (1994)); Morrison (*Nature,* 368:812-13 (1994)); Fishwild et al, (*Nature Biotechnology,* 14:845-51 (1996)); Neuberger (*Nature Biotechnology,* 14:826 (1996)); and Lonberg and Huszar (*Intern. Rev. Immunol.,* 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight.— Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Formulations

In any of the embodiments described herein, a therapeutic provided by the invention can be administered together with a pharmaceutically acceptable carrier, excipients, and/or an adjuvant. In additional embodiments, the invention provides therapeutic composition comprising a composition provided by the invention in combination with at least one additional biologically active and/or therapeutic agent such as an amino acid, peptide, polypeptide, chemical compound, drug, antibody or the like, or a combination thereof. For example, in an embodiment the therapeutic composition comprises an MG29 nucleic acid and/or MG29 polypeptide in combination with at least one additional biologically active and/or therapeutic agent such as an amino acid, peptide, polypeptide, chemical compound, drug, antibody or the like, or a combination thereof. The invention also provides methods of administering the same for the treatment or amelioration of a muscle related condition, including diabetes.

Specific examples of biologically beneficial ingredients that can be utilized in any of the embodiments described herein include: hyaluronic acid, growth factors (e.g. VEGF, TGF family), therapeutic antibodies (e.g., Humira), substance P, glucosamine, chondroitin sulphate, glycosaminoglycans, pain control agents (e.g. morphine), synovial fluid and/or its components, steroids and derivatives. It should further be understood that the combinations which are to be included within this invention are those combinations useful for their intended purpose. The agents set forth below are illustrative for purposes and not intended to be limited. The combinations which are part of this invention can be the compositions provided by the present invention and at least one additional agent selected from the lists below. The combination can also include more than one additional agent, e.g., two or three additional agents if the combination is such that the formed composition can perform its intended function.

Thus, in additional embodiments, the compositions provided by the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21.sup.st edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from normarcotic analgesics or at least one selected from antipyretics, nonsteroidal anti-inflammatory drugs, narcotic or at least one opioid analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, and nasal drugs. The topical drug can be at least one selected from local anti-infectives, scabicides or at least one pediculicide or topical corticosteroid. The nutritional drug can be at least one selected from vitamins, minerals, or calorics. See, e.g., contents of Nursing 2001 Drug Handbook, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium.

The at least one cephalosporin can be at least one selected from cefaclor, cefadroxil, cefazolin sodium, cefdinir, cefepime hydrochloride, cefixime, cefinetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of Nursing 2001 Drug Handbook).

The at least one inotropic can be at least one selected from aminone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrochloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of Nursing 2001 Drug Handbook).

The at least one normarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opioid analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenyloin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of Nursing 2001 Drug Handbook).

The at least one cholinergic (e.g., parasympathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of Nursing 2001 Drug Handbook).

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, domase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of Nursing 2001 Drug Handbook).

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of Nursing 2001 Drug Handbook).

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide .sup.131I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook).

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook).

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook).

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine sodium phosphate, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, *bacillus* Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of Nursing 2001 Drug Handbook).

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatitis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), and Micrurus fulvius antivenin. The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), Rh.sub.0(D) immune globulin (human), Rh.sub.0(D) immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of Nursing 2001 Drug Handbook).

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of Nursing 2001 Drug Handbook).

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook).

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of Nursing 2001 Drug Handbook).

The compositions provided by the present invention can further comprise at least one of any suitable and effective amount of a composition or pharmaceutical composition comprising at least one of an anti-IL-12 antibody contacted or administered to a cell, tissue, organ, animal or patient in need of such modulation, treatment or therapy, a TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etemacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23 (e.g., IL-1, IL-2, etc.). Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

The therapeutic compositions of the invention comprise, in certain embodiments, for example, a nucleic acid encoding an MG29 polypeptide, an MG29 nucleic acid; a nucleic acid that binds a nucleic acid encoding an MG29 polypeptide; an MG29 encoding nucleic acid; an MG29 peptide analog, pseudopeptide or peptidomimetic based thereon; a small molecule modulator of MG29 or a MG29 protein-protein interaction; or a MG29-specific antibody or biologically-active derivatives or fragments thereof. As described herein, MG29 plays an important role in normal muscle function. Therefore, targeting the expression and/or activity of these nucleic acids, polypeptides, and homologs thereof will allow for a novel treatment of various acute and chronic diseases and conditions related to skeletal muscle dysfunction and diabetes.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle disorder or conditions, e.g., diabetes. Such pharmaceutically acceptable carriers and excipients and methods of administration will be readily apparent to those of skill in the art, and include compositions and methods as described in the USP-NF 2008 (United States Pharmacopeia/National Formulary), which is incorporated herein by reference in its entirety. In certain aspects, the invention provides pharmaceutically acceptable formulations of the compounds described. These formulations include salts of the above compounds, e.g., acid addition salts, for example, salts of hydrochloric, hydrobromic, acetic acid, and benzene sulfonic acid.

The active compounds will generally be formulated for parenteral administration, e.g., formulated for injection via the intravenous, intraarthricular, intrathecal, intramuscular, sub-cutaneous, intra-lesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release of the active compound. For buccal administration the compositions may take the form of tablets or lozenges formulated in conventional manner.

Excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethan-e, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for injectable use include sterile aqueous solutions (where water soluble) or dispersions and sterile powders for the extemporaneous preparation of sterile injectable solutions or dispersion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. For intravenous administration, suitable carriers include physiological saline, bacteriostatic water, Cremophor™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

For administration to non-human animals, the therapeutic compositions of the invention can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

EXAMPLES

With Reference to the Drawings

Mitsugumin 29 (MG29): isolation of a muscle specific synaptophysin-related protein. The triad junction of skeletal muscle is comprised of a single invagination of the plasma membrane that plunges into the cytoplasm (the transverse-tubules or T-tubules) that is juxtaposed with two sections of the terminal cisternae of the sarcoplasmic reticulum (SR). Given the importance of the triad junction in induction of muscle contraction, it is not surprising that screening of an antibody library for novel proteins that localize to the triad junction by immunostaining has identified other proteins that regulate excitation-contraction (E-C) coupling and other aspects of $Ca^{2+}$ handling in skeletal muscle. One of the most significant proteins identified during the screening of this library is mitsugumin29 (MG29), a novel member of the syanptophysin family of transmembrane proteins.

Figure 2:
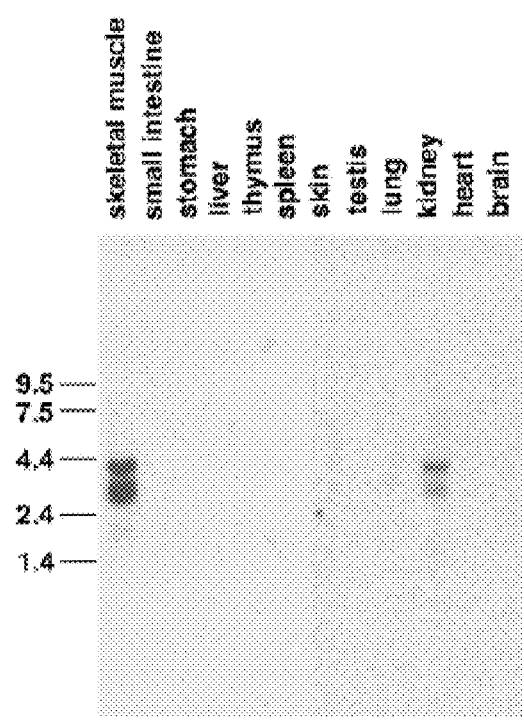
FIG. 2. MG29 is principally expressed in skeletal muscle. Northern blot analysis of various mouse tissues using a specific probe for MG29 (SEQ ID NO:1). Minimal expression is seen in kidney while there is ample expression in the skeletal muscle.

MG29 is nearly exclusively expressed in skeletal muscle fibers in both mice and humans, although some expression can be resolved in the kidney (see FIG. 1, FIG. 2 and reference #8, and contains four transmembrane domains that allow the protein to localize at both the T-tubular membrane and SR membranes of the triad junction. This subcellular distribution suggest MG29 may mediate communication between the T-tubular and junctional SR membrane. The protein structure of MG29 is homologous in amino acid sequence and shares characteristic structural features with the members of the synaptophysin family, a family of proteins essential for neurotransmitter release.

Synaptophysin: synaptic formation, release and biogenesis. Synaptophysin was originally identified as an abundant and highly immunogenic membrane protein of small synaptic vesicles that is also found in dense-core chromaffin and neurosecretory granules. Synaptophysin and its homologues, synaptoporin (or synaptophysin II) and pantophysin, share a common transmembrane organization, with four membrane-spanning regions and cytoplasmic amino and carboxy termini.

A unique feature of synaptophysin is that it have an oligomeric structure leading to the idea that synaptophysin may be a component of the fusion pore that forms during neurotransmitter release. Moreover, it has been shown that antisense oligonucleotides complementary to the synaptophysin mRNA reduce $Ca^{2+}$-dependent glutamate secretion from *Xenopus* oocytes induced by injection of total brain mRNA. Microinjection of synaptophysin antibody into motor neurons blocked neuromuscular transmission. These data are consistent with synaptophysin being essential for neurotransmitter secretion. However, genetic approaches to identify the function of synaptophysin have not been successful; mutant mice lacking synaptophysin show a normal phenotype. This may reflect compensation by synaptoporin or other synaptophysin family members. Indeed, mice doubly deficient in synaptophysin and synaptogyrin display defects in synaptic plasticity.

Synaptophysin has been proposed to play a structural role in vesicle formation. Based on its high capacity to bind cholesterol, synaptophysin has been implicated in the generation of membrane curvature during synaptic vesicle biogenesis. Synaptophysin is also known to tightly interact with other proteins of the synaptic vesicle membrane, i.e. synaptobrevin and the vacuolar $H^+$-ATPase. These interactions are thought to regulate exocytotic membrane fusion at the level of the SNARE complex or fusion pore formation. The latter idea is supported by studies on yeast vacuole fusion that implicate the vacuolar ATPase directly participate in membrane fusion.

Skeletal muscles are among the most plastic tissue in nature, and normal muscle physiology requires the formation and maintenance of the complex membrane structures. Throughout development, aging and other processes including fatigue require constant adaptations of the skeletal muscle system, thus identification and characterization of genes and proteins involved with plasticity in skeletal muscle membrane structures is essential to understand muscle physiology. Thus, structurally MG29 might be seen as a counterpart of synaptophysin in skeletal muscle biogenesis.

Discovery of a role of MG29 in muscle fatigue. Considering the extent of disruption to the triad junction membrane ultrastructure in mg29(−/−) animals, the lack of an identifiable function phenotype in non-stressed animals was surprising. We then reasoned that since physiological responses are modified under conditions of stress we needed to investigate the response of mg29(−/−) animals and their muscles under such conditions. Initially, we tested the in vivo response of the whole animal to stress induced by treadmill running exercise. We found that the knockout animals were not able to sustain physical activity for extended periods of time and run significantly less than wild type littermate controls. These studies gave us the initial clues that MG29 was a physiologically relevant molecule with direct roles in muscle performance, particular during increased physical activity. Since physical inactivity may lead to a number of chronic-degenerative diseases, reduced muscle function and muscle wasting, we next investigated the role of MG29 in muscle fatigue.

Muscle fatigue is broadly defined as the decline in ability of a muscle to create force, due to either repetitive or continued activity. Fatigue is a phenomenon experienced by all animals and is thought to be part of a biological control process that limited extended muscle contraction to minimize damage produced by overexertion. Some of the current theories of the cellular mechanisms underlying muscle fatigue include: a) disruption of the effective communication between the T-tubules and $Ca^{2+}$ release from the SR, b) changes in the concentration of sodium or other ions in muscle cell that leads to failure of action potential propagation. c) reactive oxygen species (ROS)/metabolites theory suggests increased muscle activity leads to a net increase in superoxide, hydrogen peroxide and free radicals that can directly modify protein function. This theory is sometimes expanded into a broader concept that postulates that the overall accumulation of metabolites such as ROS, inorganic phosphate, ADP, AMP, etc, buildup during fatigue and cause both a decrease in the amount of $Ca^{2+}$ release from the SR and functional inhibition of the myosin-actin interaction. d) fatiguing stimulation leads to a rise in intracellular $Ca^{2+}$, inducing $Ca^{2+}$-activated proteases and subsequent cleavage of essential E-C coupling related proteins.

While the mechanism at work is not clearly defined, a consensus view in muscle physiology research is that optimal muscle performance revolves around the maintenance of intracellular $Ca^{2+}$ homeostasis, as inadequate $Ca^{2+}$ release from the SR leads to decreased force output. During fatigue, this deficient $Ca^{2+}$ release process could result from improper coupling between the T-tubules and ryanodine receptors (RyR) on the SR membrane, a reduction of the SR $Ca^{2+}$ content, direct modification of RyR function and compromised store-operated $Ca^{2+}$ entry (SOCE).

We investigated the fatigability properties of skeletal muscles from the mg29(−/−) mice using and ex vivo muscle contractility assay and we found that they fatigued to a greater extent, recovered to a lesser extent after fatigue and produced less force, even in the presence of caffeine, than wild type control mice. These findings clearly suggest that E-C coupling in mg29(−/−) skeletal muscle is disrupted. This difference in fatiguing characteristics between muscles from mg29(−/−) and wild type mice was significantly reduced when $Ca^{2+}$ was removed from the extracellular medium and/or when extracellular $Ca^{2+}$ entry was pharmacologically blocked, implicating extracellular $Ca^{2+}$ entry as a major factor in the decreased fatigue resistance in mg29(−/−) muscle.

MG29 as a sentinel against aging-related dysfunction of Ca homeostasis in skeletal muscle. Aging effects on muscle function have been associated with muscle fiber denervation, loss of motor units, and motor unit remodeling. Since functional alterations occur before significant muscle wasting becomes evident, changes in E-C coupling machinery and intracellular Ca homeostasis may act as causative factors for, or adaptive responses to, muscle aging. Altered function of several triad junction proteins, including DHPR (Delbono, O. O'Rourke, K. S. & Ettinger, W. H. Excitation-calcium release uncoupling in aged single human skeletal muscle fibers. *J Membr Biol* 148, 211-22 (1995); Renganathan, M., Messi, M. L. & Delbono, O. Dihydropyridine receptor-ryanodine receptor uncoupling in aged skeletal muscle. *J Membr Biol* 157, 247-53 (1997)), calsequestrin (Margreth, A., Damiani, E. & Bortoloso, E. Sarcoplasmic reticulum in aged skeletal muscle. *Acta Physiol Scand* 167, 331-8 (1999); Narayanan, N., Jones, D. L., Xu, A. & Yu, J. C. Effects of aging on sarcoplasmic reticulum function and contraction duration in skeletal muscles of the rat. *Am J Physiol* 271, C1032-40 (1996)), and SERCA (Chen, B., Jones, T. E. & Bigelow, D. J. The nucleotide-binding site of the sarcoplasmic reticulum Ca-ATPase is conformationally altered in aged skeletal muscle. *Biochemistry* 38, 14887-96 (1999); Schoneich, C., Viner, R. I., Ferrington, D. A. & Bigelow, D. J. Age-related chemical modification of the skeletal muscle sarcoplasmic reticulum Ca-ATPase of the rat. *Mech Ageing Dev* 107, 221-31 (1999)), have been shown to contribute to disrupted Ca homeostasis in aged skeletal muscle. It has been suggested that cumulative uncoupling of the voltage-induced Ca release (VICR) process may be part of the causative and/or adaptive changes during muscle aging (Payne, A. M. & Delbono, O, Neurogenesis of excitation-contraction uncoupling in aging skeletal muscle. *Exerc Sport Sci Rev* 32, 36-40 (2004)). Identification of molecular markers of muscle aging, and their contribution to aging-related muscle dysfunction, has recently emerged as a major focus in E-C coupling studies and geriatric medical research in general.

Extending our initial discovery of Ca sparks in healthy young muscle, we have identified a phenotypic change of Ca spark signaling in aged skeletal muscle (Weisleder, N. et al. Muscle aging is associated with compromised Ca2+ spark signaling and segregated intracellular Ca2+ release. *J Cell Biol* 174, 639-45 (2006); Melzer, W. When sparks get old. *J Cell Biol* 174, 613-4 (2006)). It appears that the plastic nature of Ca sparks in young muscle is compromised in aged skeletal muscle where the duration of the Ca spark response is diminished and cannot be restimulated by additional rounds of osmotic stress. One can expect that compromised Ca spark signaling in aged muscle may be linked to the changes in t-tubule/SR membrane structure and/or modification of the SR Ca release machinery, perhaps resulting from aging-related alterations in protein expression. Using biochemical assays, we found that the expression of MG29 is significantly decreased in aged skeletal muscle. MG29 is essential for maintenance of membrane structure and Ca signaling in skeletal muscle (Takeshima, H. et al. Mitsugumin29, a novel synaptophysin family member from the triad junction in skeletal muscle. *Biochem J* 331 (Pt 1), 317-22 (1998); Brandt, N. R. & Caswell, A. H. Localization of mitsugumin 29 to transverse tubules in rabbit skeletal muscle. *Arch Biochem Biophys* 371, 348-50 (1999); Komazaki, S., Nishi, M., Takeshima, H. & Nakamura, H. Abnormal formation of sarcoplasmic reticulum networks and triads during early development of skeletal muscle cells in mitsugumin29-deficient mice. *Dev Growth Differ* 43, 717-23 (2001); Komazaki, S., Nishi, M., Kangawa, K. & Takeshima, H. Immunolocalization of mitsugumin29 in developing skeletal muscle and effects of the protein expressed in amphibian embryonic cells. *Dev Dyn* 215, 87-95 (1999); Nishi, M. et al. Abnormal features in skeletal muscle from mice lacking mitsugumin29. *J Cell Biol* 147, 1473-80 (1999)). Abnormalities of membrane ultrastructure around the triad junction were detected in skeletal muscle from both young mg29(-/-) and aged wt mice: the t-tubule was swollen and sometimes missing from the A-I junction, and the SR networks were poorly formed with vacuolated and fragmented structures, leading to misalignment of triad junctions (Nishi, M. et al. Abnormal features in skeletal muscle from mice lacking mitsugumin29. *J Cell Biol* 147, 1473-80 (1999)).

In addition to the parallel changes in the membrane structure in young mg29-/- and aged wt muscle, several additional studies suggest that MG29 can be used as a molecular marker for muscle aging. First, the mg29(-/-) mice display muscle weakness at age 6 months or younger, which resembles the atrophic phenotype of aged wt mice (Nagaraj, R. Y. et al. Increased susceptibility to fatigue of slow- and fast-twitch muscles from mice lacking the MG29 gene. *Physiol Genomics* 4, 43-9 (2000)). Second, store-operated $Ca^{2+}$ entry (SOCE) in aged muscle is significantly down-regulated (Brotto, M., Weisleder, N. & Ma, J. J. Store-Operated Ca2+ Entry in Muscle Physiology. *Curr Chem Biol* 1 (2007)), which is similar to the dysfunctional properties of SOCE identified in mg29(-/-) neonatal (Pan, Z. et al. Dysfunction of store-operated calcium channel in muscle cells lacking mg29. *Nat Cell Biol* 4, 379-83 (2002)) and adult (Brotto, M. A. et al. Functional but reduced store-operated Ca entry in adult mg29(-/-) skeletal muscles. *Biophs J* 88, 633A (2005)) muscles. Third, there appears to be a common phenomenon of segregated Ca releasable pools that exhibit differential sensitivity to EC-coupling in both mg29(-/-) and aged muscle. Our studies illustrate that a segregated Ca pool that cannot be mobilized by the physiological VICR mechanism may exist in both young mg29(-/-) and aged wt muscle fibers (Weisleder, N. et al. Muscle aging is associated with compromised Ca2+ spark signaling and segregated intracellular Ca2+ release. *J Cell Biol* 174, 639-45 (2006)). Fourth, we identified a loss of plastic Ca spark signaling in young mg29(-/-) muscles, in a fashion very similar to that seen in aged skeletal muscle. Identification of the compromised Ca sparks signaling and segregated intracellular Ca release may provide unique targets for future therapeutic interventions against the effects of aging on muscle performance.

Elevated blood glucose levels in mg29-/- mice due to altered muscle glucose uptake. The major hallmark of diabetes mellitus is the elevation of glucose levels in the blood of affected patients. This state can develop due to reduced insulin secretion, as in type I juvenile diabetes, or due to compromised response of the body to insulin, as in type II insulin resistance diabetes. Skeletal muscle is a major target for insulin as muscle is responsible for much of the glucose consumption in the body and thus can absorb large quantities of glucose in the presence of insulin. For this to occur, vesicles containing glucose transporter type 4 (Glut4) must translocate to the plasma membrane. As MG29 plays an important role in membrane fusion in skeletal muscle, it is possible that MG29 could contribute to the mechanism controlling the increase of Glut4 on the plasma membrane in response to insulin.

Figure 3:
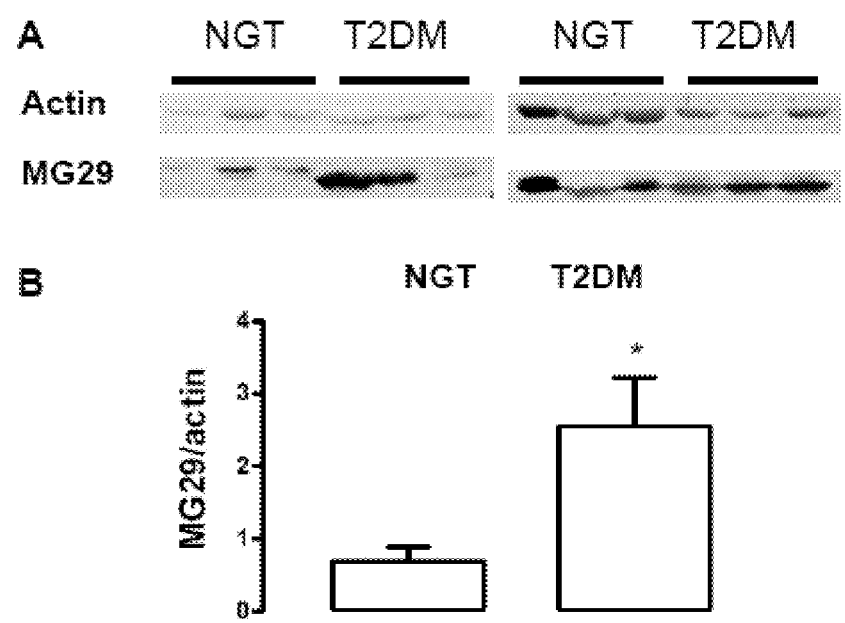
FIG. 3. Increased expression of MG29 in skeletal muscles of normal individuals and type 2 diabetic patients. Muscle samples were collected from normal individuals (NGT) and type 2 diabetic patients. (A) Western blot was performed to measure the expression levels of MG29 and actin to allow for normalization of MG29 expression level. B) Protein expression was quantified using the densitometry and analyzed using ImageJ software. The bar chart shows that significantly more MG29 is skeletal muscle from diabetic human patients. Results represent the mean±SEM. N=6. *: P<0.05
Figure 4:
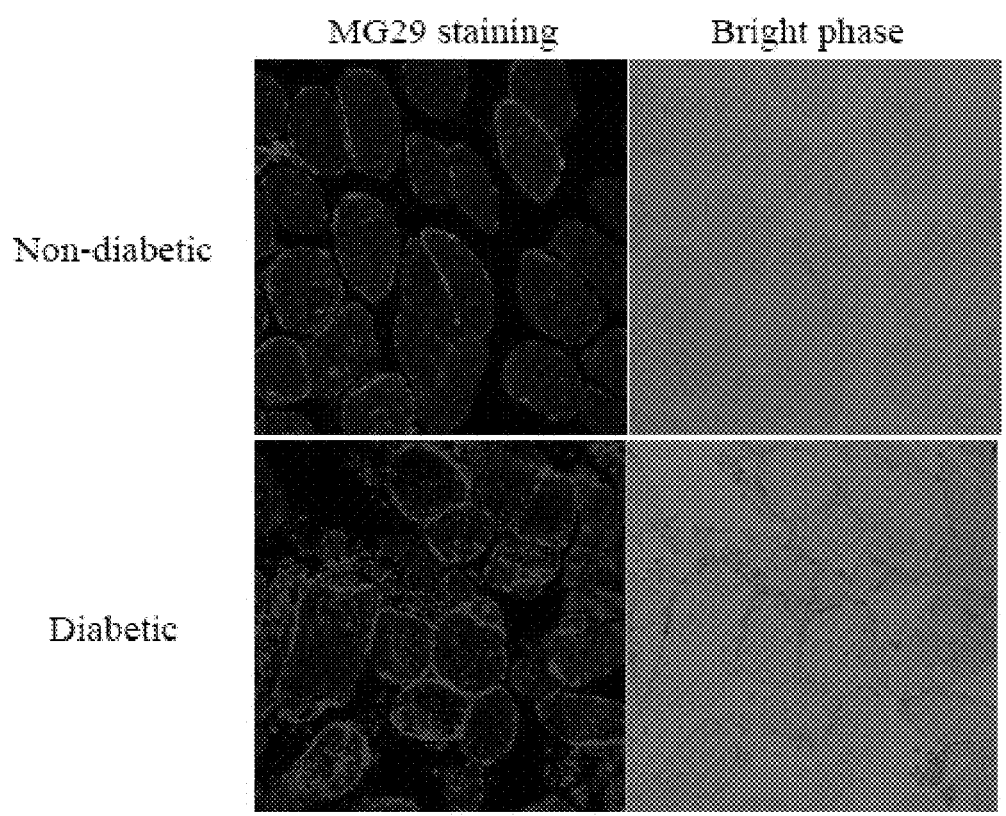
FIG. 4. MG29 localization patterns are altered in human diabetic skeletal muscle. Localization of endogenous MG29 in normal human skeletal muscle (top) and type 2 diabetic patients (bottom). Paraformaldehyde-fived, paraffin-embedded sections were immunostained with MG29 antibody (left) and then examined by confocal microscopy. Bright-field microscopy (right) was used to establish muscle fiber positioning and determine the quality of the histological section.

To test this hypothesis, we first examined how MG29 levels are altered in the muscle from human diabetic patients. If MG29 is an important component of the Glut4 machinery in skeletal muscle then one would predict that the expression of MG29 and/or the subcellular localization of the MG29 protein would be altered in skeletal muscle from diabetic human patients. Indeed, this proves to be the case. We find that expression of MG29 protein is substantially increased in skeletal muscle biopsies from diabetic patients (FIG. 3). This is likely a compensatory response in these diabetic muscles in an attempt to increase glucose uptake. However, our examination of the localization of MG29 in diabetic muscle suggested that this additional MG29 expression cannot improve glucose uptake as the MG29 protein localization in altered in diabetic muscle (FIG. 4). In diabetic muscle, MG29 is much more common in the intracellular space while in normal muscle most of the MG29 is found at sarcolemmal membrane. This mislocalization likely contributes to the progression of the diabetic pathology.

To directly test the role of MG29 in diabetes we conducted glucose challenge experiments in young mg29-/- mice. We found that both male and female mg29-/- animals were unable to effectively clear glucose from their bloodstream following a bolus interperitoneal (IP) injection of glucose (FIG. 5). Notice that the resting glucose level remains unchanged, suggesting that the absence of MG29 does not affect the role of the liver in glucose metabolism. Since the mg29-/- glucose levels remain high for an extended period, it appears there is a defect in the ability of the mg29-/- muscle to uptake glucose rather than a defect in insulin secretion. This was confirmed by further experiments were an insulin challenge was performed on mg29−/− and control animals. While an IP injection of insulin can induce a significant decrease in blood glucose in wild type control animals, the same injection of insulin has much less effect on the blood glucose level in mg29−/− mice (FIG. 6). These findings indicate that the underlying defect leading to elevated blood glucose in mg29−/− mice is in glucose clearance from the animal rather than compromised insulin production, a situation similar to that seen in type II diabetic patients. Thus, absence of MG29 from skeletal muscle can predispose animal to develop diabetic symptoms.

We tested if the mg29−/− animals would be more susceptible to developing diabetes by feed them and aged matched wild type control mice a high fat diet. This approach is known to induce diabetes in mice. While mg29−/− and control mice put on weight at similar rates (FIG. 7a), the mg29−/− mice developed a susceptibility to glucose challenge experiments at a much younger age than the control mice (FIG. 7b). This provides additional evidence that MG29 is necessary for skeletal muscle to absorb glucose from the bloodstream to maintain energy supplies in the muscle and decrease the blood glucose levels to prevent diabetes. If the absence of MG29 can induce diabetes, then manipulation of MG29 expression and/or could provide an effective method for treating both type I and type II diabetes.

Figure 8:
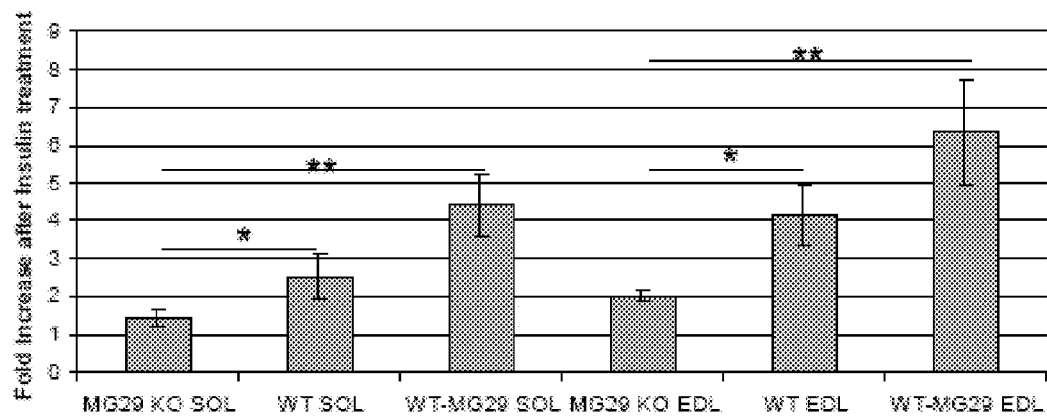
FIG. 8. Altering MG29 expression levels modulates glucose uptake in isolated mouse muscle. Soleus (SOL) or extensor digitorum longus (EDL) muscles were excised from either wild type (WT), mg29−/− (MG92 KO) or wt mice that overexpress MG29 due to treatment with a recombinant AAV (WT-MG29). These muscles were tested for their capacity to uptake radiolabelled 2-Deoxyglucose (2-DG) before and after exposure to insulin (200 nM). mg29−/− mice displayed significantly decreased 2-DG uptake compared to wt mice, while MG29 overexpression mice displayed increased glucose uptake capacity. These findings indicate that MG29 is essential for insulin-stimulated glucose uptake and that providing additional MG29 within the muscle cell can increase glucose uptake. Thus, increased MG29 expression represents a viable approach for lowering blood glucose levels in the treatment of diabetes. Values are means±SEM for 5-10 muscles. *P<0.05; **P<0.01.
Figure 15:
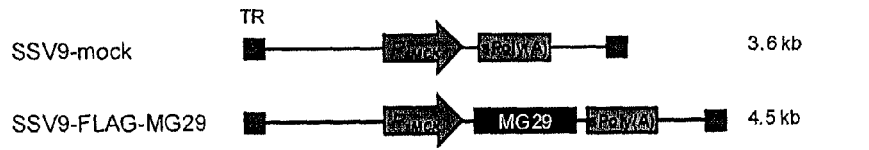
FIG. 15. Recombinant AAV can produce MG29 expression in native skeletal muscle. (a) Schematic diagram of recombinant AAV constructs designed to produce muscle specific expression of MG29. (b) C2C12 myotubes or non-muscle HEK293 cells were infected with SSV9-FLAG-MG29. Western blot analysis shows that time-dependent MG29 expression was restricted to the muscle cells. (c) Gastronemius muscles were injected with SSV9-FLAG-MG29 or SSV9-mock (control) and muscles were removed after 5 days. Western blotting shows increased expression of MG29 compared to control muscle from the same animal, and the FLAG tag from the recombinant MG29 is present in the injected muscle. Optimization of viral titer and time of incubation should increase the levels of MG29 expression in muscle.
Figure 15:
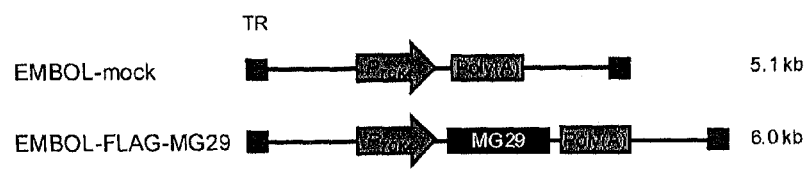
Figure 15:
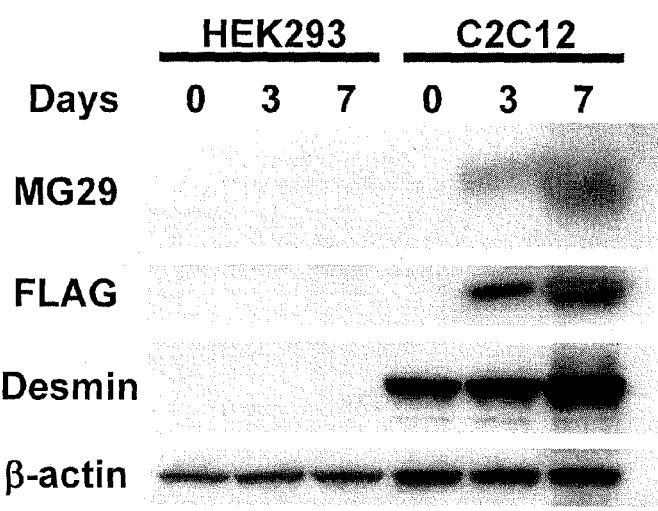
Figure 15:
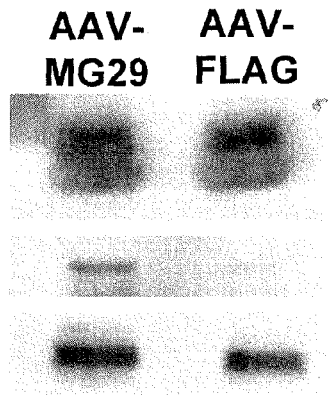

In another series of experiments we directly tested these hypotheses that loss of MG29 expression would prevent insulin induced glucose uptake into muscle and that expression of additional MG29 would increase the capacity of skeletal muscle to uptake glucose. Here we used a 2-deoxyglucose uptake assay to measure the ability of different mouse muscles to absorb glucose at the resting state and when exposed to insulin. (FIG. 8) Soleus or extensor digitorum longus (EDL) muscles were excised from either wild type MG29 knockout (mg29−/−) mice and tested for glucose uptake. In this assay we see that mg29−/− mice displayed significantly decreased 2-DG uptake compared to wt mice, confirming our earlier finding that glucose uptake is compromised in these mice. In another set of experiments, we measured glucose uptake for wild type mice that overexpress MG29 due to treatment with a recombinant AAV that produced increased MG29 expression exclusively within the skeletal muscles (see FIG. 15). When these MG29 overexpressing muscles were tested for their uptake capacity they displayed increased glucose uptake capacity. These findings indicate that MG29 is essential for insulin-stimulated glucose uptake and that providing additional MG29 within the muscle cell can increase glucose uptake. Thus, increased MG29 expression represents a viable approach for lowering blood glucose levels in the treatment of diabetes.

Figure 9:
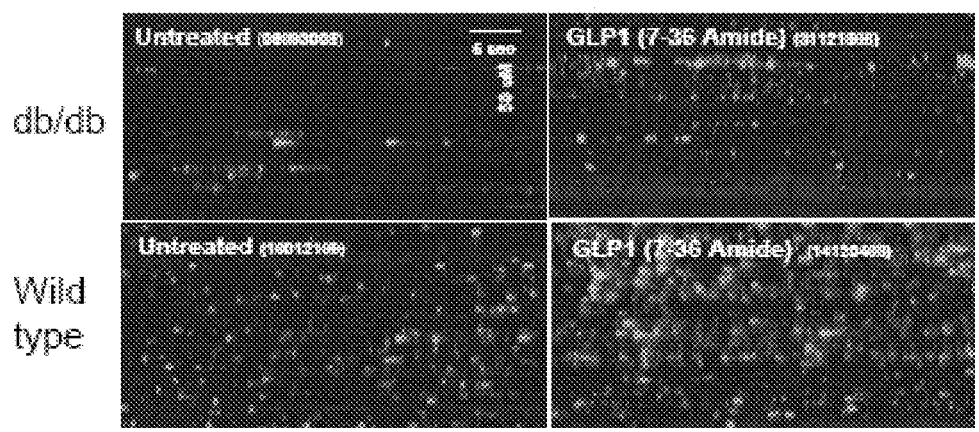
FIG. 9. Compromised $Ca^{2+}$ spark activity in db/db muscle is dependent upon the hyperglycemia condition. (a) Representative line scan images of $Ca^{2+}$ sparks in db/db muscle (top) or wild type muscle (bottom), either treated with vehicle (left) or GLP1 (right). Note the major reduction in frequency of $Ca^{2+}$ sparks in the db/db muscle can be reversed through the use of GLP1. (b) GLP1 exerts its maximum activity on db/db mice that exhibit high hyperglycemia condition. Results are Mean±SEM. ‡Statistically significant (p<0.01) by ANOVA. High blood glucose refers to the animals that have measured blood glucose of >330 mg/dL. Lower blood glucose refers to animals that have measured blood glucose of <260 mg/dL. n=534 for Untreated high blood glucose (HBG) group; 851 for Treated high blood glucose (HBG) group; 730 for Untreated lower blood glucose (LBG) group; 555 for Treated lower blood glucose (LBG) group.
Figure 9:
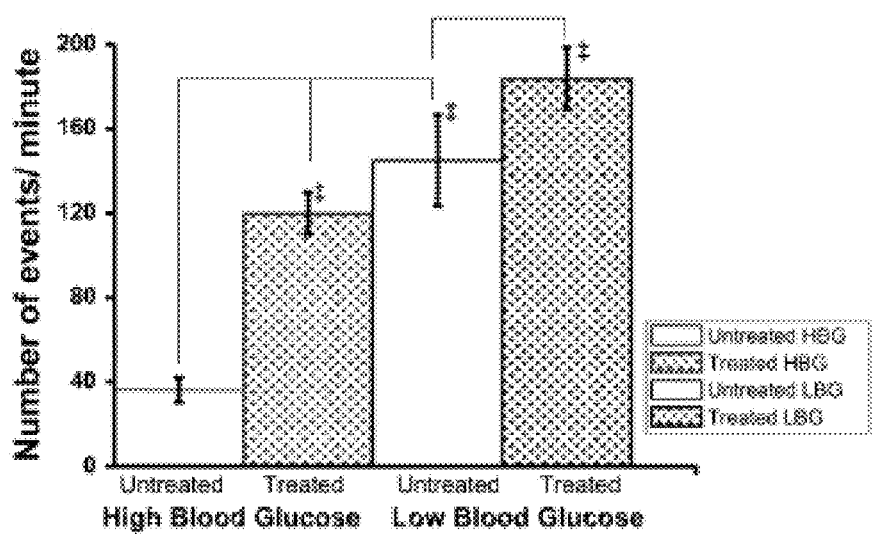

The Ca spark response in skeletal muscle is compromised in mg29−/− and diabetic muscle. Our previous work has shown that mg29−/− skeletal muscle displays a compromised Ca spark response following osmotic stress[8]. Considering that we see a similar functional phenotype with glucose handling between the mg29−/− animal and diabetic patients, we tested if the we would see similar defects in Ca signaling as well. Ca spark measurement is performed in 13-16 weeks old control wild type, type I diabetic mice (akita) or type II diabetic mice (db/db). Non-fasted serum glucose levels are recorded from blood samples taken from the tail vein immediately before sacrificing the mice. Following an established protocol in our laboratory, we measured Ca sparks in muscle fibers isolated from the flexor digitorum brevis (FDB). We observed no increase in the frequency of spontaneous resting Ca sparks in db/db muscle fibers (data not shown). Previous studies in our laboratory showed that transient exposure of osmotic stress by application of brief hypotonic Tyrode solution swells the sarcolemmal membrane and immediate wash with isotonic Tyrode leads to the restoration of membrane volume followed by peripheral robust Ca sparks activity in the young and healthy WT muscle fibers. Using this approach, we found that db/db muscle fibers exhibit greatly reduced number of Ca sparks events when compared to the WT muscle fibers (FIG. 9a). The degree that the spark frequency decreased could be directly correlated with the blood glucose level of the animal, with more diabetic animals displaying less sparks than those animals with lower blood glucose levels (FIG. 9b). When db/db mice are categorized based on their non-fasted blood glucose levels, we found that there is a threshold that when the blood glucose is lower than 260 mg/dL (lower blood glucose) the frequency of $Ca^{2+}$ sparks are not compromised (145±22 events/min) despite the obvious obesity observed in these mice Furthermore, we found decreased Ca sparks in the akita model of type I diabetes. These results suggest that reduced Ca sparks is a common feature of diabetic muscle, and that this phenotype may be attributed to changes in MG29 expression or function as they closely mimic the known phenotype of mg29−/− skeletal muscle.

Treatments associated with improved glucose levels restore Ca spark response in diabetes. Recent discoveries in diabetes treatment have focused on targeting the activity of incretins, gastrointestinal hormones that are activated following meal ingestion, as a therapeutic approach for type II diabetes. Glucagon like peptide 1 (GLP1) of pro-glucagon origin is a type of incretin hormone. The physiological function of GLP1 includes stimulating insulin release from pancreatic β-cells and inhibition of glucagon activity, thus making it a therapeutic target for treatment of DM (Gutniak, M., Orskov, C., Holst, J. J., Ahren, B. & Efendic, S. Antidiabetogenic effect of glucagon-like peptide-1 (7-36) amide in normal subjects and patients with diabetes mellitus. *N Engl J Med* 326, 1316-22 (1992)). Sitagliptin (Januvia) discovered by Merck, is targeted to inhibit dipeptidyl-peptidase 4 (DPP-4) that cleaves GLP1, thus increasing the lifespan of GLP1 in the human body. Although patients who have been treated with Januvia exhibit normalization of blood glucose, the physiological effects of Januvia in skeletal muscle have not been fully examined at this point. Interestingly, ex vivo study of rat's soleus muscle incubated with GLP1 exhibits increased PKB and glycogen synthase activity, indicating improved metabolism and function (Acitores, A., Gonzalez, N., Sancho, V., Valverde, I. & Villanueva-Penacarrillo, M. L. Cell signalling of glucagon-like peptide-1 action in rat skeletal muscle. *J Endocrinol* 180, 389-98 (2004)).

Figure 10:
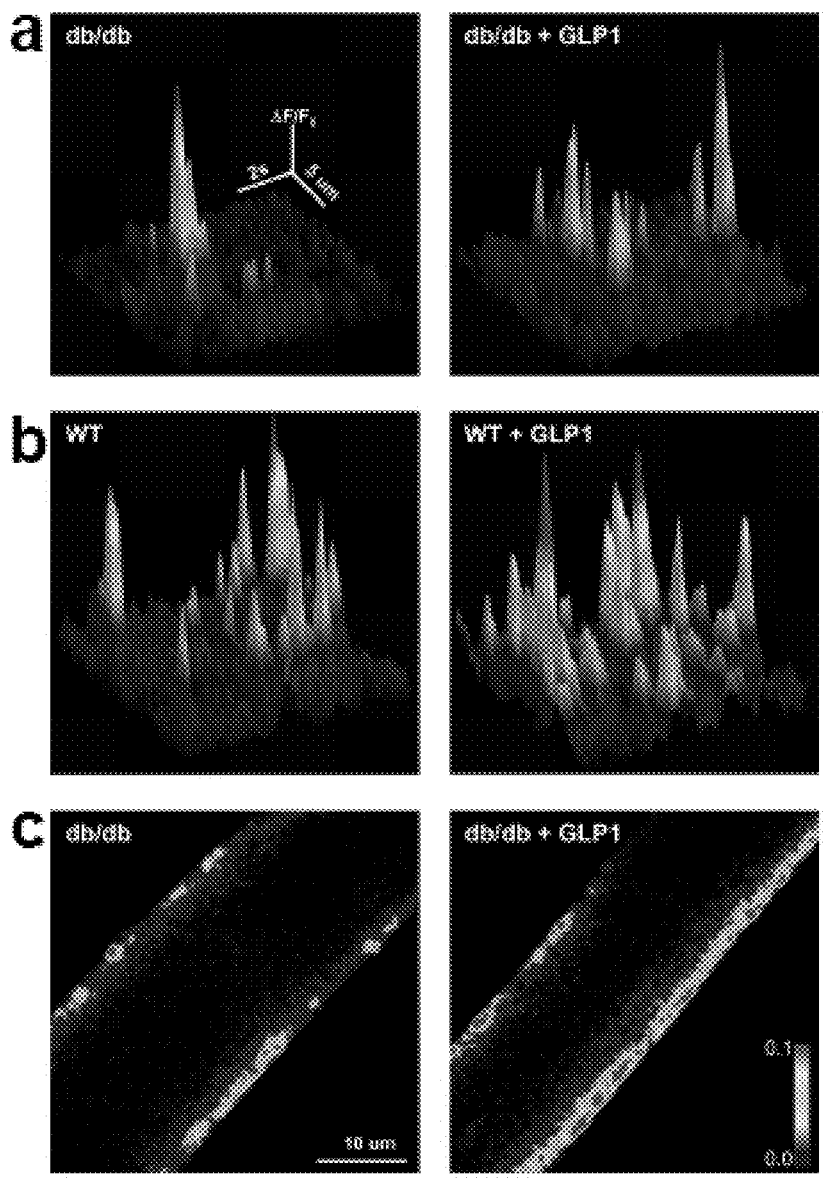
FIG. 10. Reduced $Ca^{2+}$ sparks signaling in diabetic skeletal muscle. (a) Isolated FDB muscle fibers were treated with hypotonic shock to generate a $Ca^{2+}$ sparks response. Cross section line scan of diabetic FDB muscle fiber after osmotic shock (left). Diabetic (db/db) fibers that have been acutely treated with GLP1 exhibit significant increased $Ca^{2+}$ sparks activity (right). (b) WT fibers exhibit robust $Ca^{2+}$ sparks signaling. (c) Localization of sparks was established using a custom designed IDL data processing software routine. Diabetic skeletal muscle fiber show reduced peripheral $Ca^{2+}$ sparks frequency (left). Treatment of GLP1 in db/db fibers does not alter the peripheral subsarcolemmal distribution of $Ca^{2+}$ sparks, implying that although $Ca^{2+}$ signaling cascade is altered in diabetic fiber, the factors responsible for maintaining $Ca^{2+}$ spark localization near the membrane remains intact (right). Pseudocolor represents the average intensity of $Ca^{2+}$ release events at each point within the fiber.

Here we tested if GLP1 treatment would not only reduce blood glucose levels, but if it could also increase the number of Ca sparks observed in diabetic skeletal muscle. We found that GLP1 treatment (10 nM) for 1 hour significantly improves the $Ca^{2+}$ spark events in db/db muscle fibers, restoring $Ca^{2+}$ spark frequency to levels similar to untreated WT (FIG. 10a, b). This implies that GLP1 treatment could activate the signaling cascade that leads to increased RyR's open probability (Po) rather than the number of RyRs per fiber, as GLP1 treatment of WT muscle leads to minimal increases in $Ca^{2+}$ spark frequency. As shown in a plot of $Ca^{2+}$ spark localization, treatment of GLP1 in either db/db or WT fibers does not alter the peripheral subsarcolemmal distribution of $Ca^{2+}$ sparks (FIG. 10c), implying that although $Ca^{2+}$ signaling cascade is altered in diabetic fiber, the factors responsible for maintaining $Ca^{2+}$ spark localization near the membrane remains intact.

Figure 11:
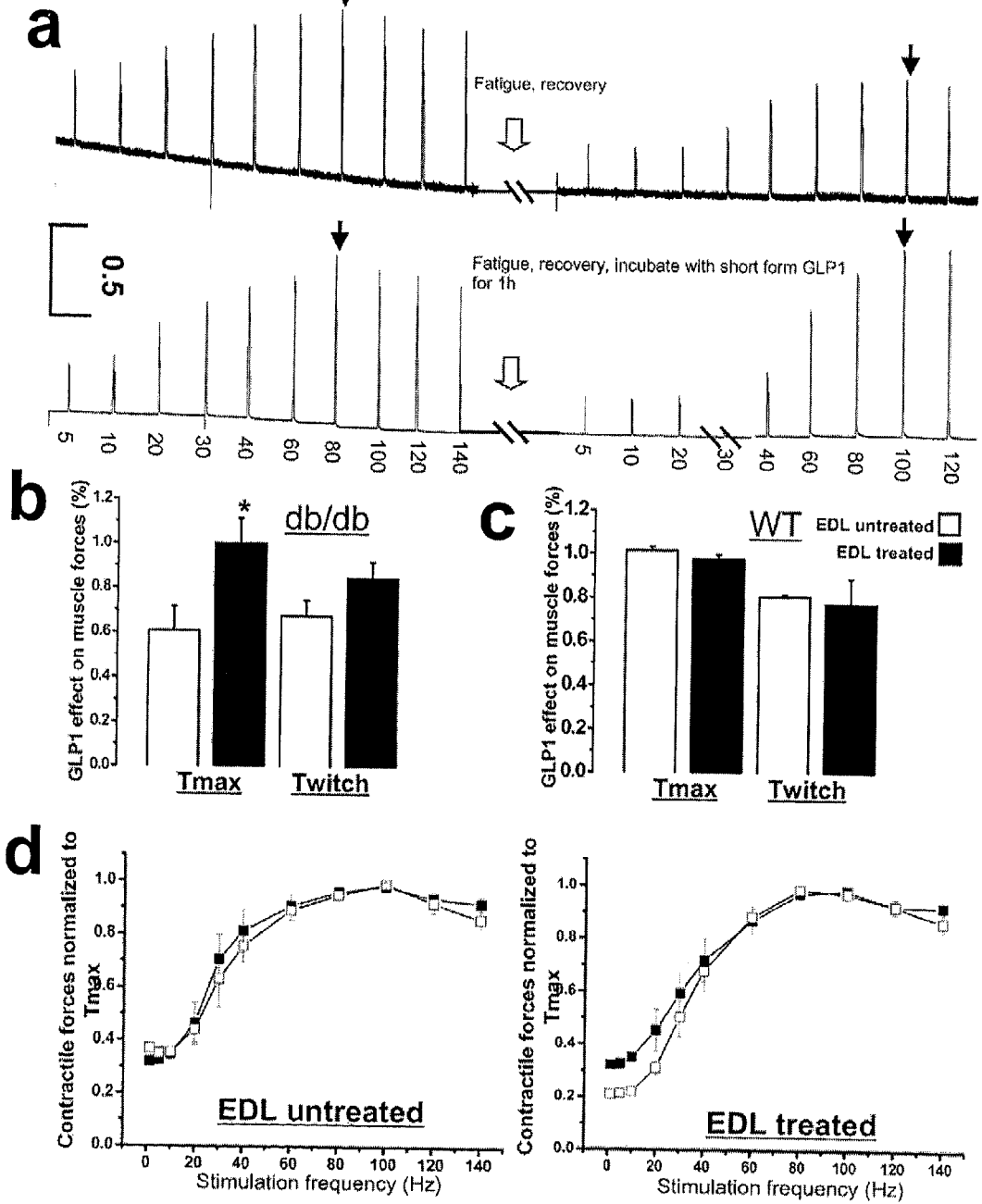
FIG. 11. GLP1 treatment improves muscle force in diabetic EDL after fatigue. (a) Representative traces of force vs. frequency relationship in control (upper) and GLP1 treated EDL. Diabetic muscles were first subject to a range of electric field stimulations (5~140 Hz) at 30 s interval, then fatigue was induced by 20 Hz stimuli at 2 ms interval for 5 min. EDL diabetic muscles were allowed to recovery under 20 Hz stimuli at 1 min interval for 30 min and 100 nM GLP1 was added into the bathing solution for 1 h (truncated portion of the trace). Immediately followed, another force versus frequency was performed using the same range of stimulations. Black arrows designate Tmax and hollow arrows pointed the fatigue, recovery and GLP1 incubation portion that were truncated. (b) The ratio of Tmax (maximal force) and twitch force (force at 1 Hz) after fatigue to force before fatigue was calculated in diabetic and (c) WT before and after GLP1 treatment. Blank bar represented untreated group and hatched bar represented GLP1 treated group. N=5, *P<0.05. (d) Force vs. frequency relationship of 5 pairs each of EDL muscles in untreated group (left) and GLP1 treated group (right) were summarized in this panel. Solid square represented the force versus frequency before fatigue and open square represented that after fatigue. All data showed are mean±S.E.

Application of GLP1 can improve contractility in skeletal muscle from diabetic mice. Our data on the Ca handling characterisitics of diabetic skeletal muscle indicate that the compromised Ca spark response in diabetic animals can be reversed through the application of GLP1. This leads us to test whether the increased Ca sparks activity can be translated as increased muscle force as measured by ex vivo contractility assays. The extensor digitorum longus (EDL) of non-fasted db/db mice is mounted to a force transducer and electrically stimulated following the protocol shown in FIG. 11. A 10 fold higher dose of GLP1 (100 nM) used in the $Ca^{2+}$ spark experiments is applied to the contractility study, to take into account the increased mass of the anatomical muscle over the isolated muscle fiber. Muscles were tested for their maximum force (Tmax) produced at various frequencies and then fatigued using rapid pulses of an electric field, which was then followed by another measurement of Tmax. Following 1 hour of GLP1 application, this stimulation protocol was repeated on the same muscles (FIG. 11*a*). Calculating the ratio of Tmax before and after GLP1 application will show how the application of GLP1 can influence the recovery of muscle function following fatigue.

In a series of contractility experiments using db/db muscle, we found that GLP1 treatment is able to increase the Tmax recovery ratio for db/db mice. In untreated db/db muscle, the recovery ratio (0.6) was decreased compared to untreated WT (1.1). GLP1 exposure could restore the recovery ratio in db/db muscle back to the levels seen in the WT muscles (FIG. 11*b,c*). This data suggest that GLP1 treatment allows for better recovery from muscle fatigue resulting from intense stimulation.

Further examination of the contractile aspects of muscle indicates that GLP1 treatment did not significantly alter the force frequency relationship in db/db muscle fibers (FIG. 11*d*). Additionally, there is no significant change in twitch ratio after GLP1 treatment. This suggests that GLP1 treatment does not alter the sensitivity of the muscle contractile apparatus to Ca. Thus, the muscle preparations are responding to GLP1 exposure through the action of an upstream signaling pathway instead of a change in the contractile proteins.

Figure 12:
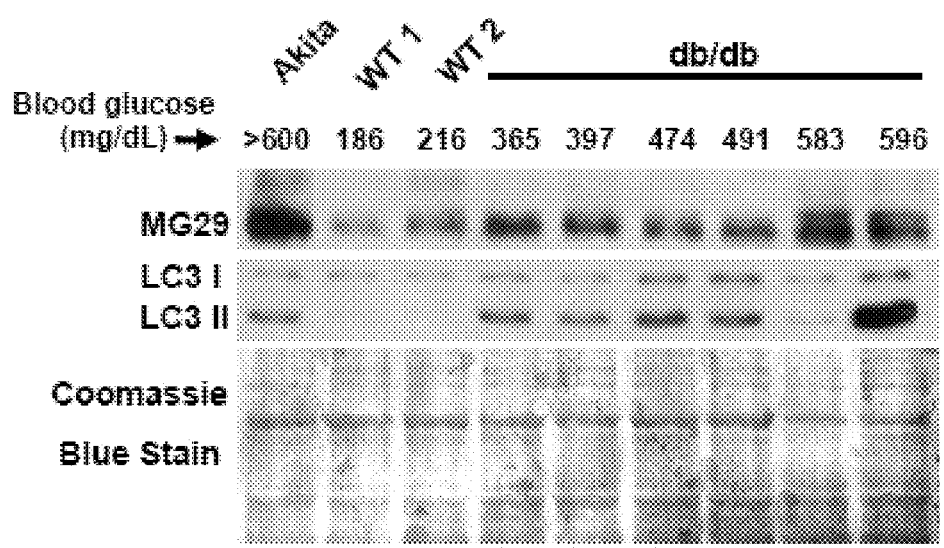
FIG. 12. Altered MG29 expression and increased autophagy in diabetic muscle. Western blot analysis shows that MG29 protein levels increase in diabetic muscle from either type I diabetic mice (akita) or type II diabetic mice (db/db). This increase occurs in direct correlation with the glucose concentration in the blood of each mouse. This may constitute a compensatory response in the diabetic muscle as an attempt to increase the glucose uptake capacity of skeletal muscle in response to increasing blood glucose levels in diabetic mice. Additionally, there is increased autophagy in the muscle of both these diabetic models as indicated by the increased conversion of microtubule-associated protein light chain 3 (LC3), a marker of autophagy.

Changes in MG29 expression and autophagy markers in diabetic muscle. Frequently the pathophysiological response to disease in a tissue will include changes in the expression of particular genes. Since we have linked the absence of MG29 to diabetic phenotypes, such as the development of high blood glucose levels and Ca handling defects, we tested what changes there could be MG29 expression in diabetic muscle. In FIG. 12, we find that MG29 protein levels increase in muscle with diabetes in direct correlation with the glucose concentration in the blood. This may constitute a compensatory response in the diabetic muscle as an attempt to increase the glucose uptake capacity of skeletal muscle in response to increasing blood glucose levels in diabetic mice.

Interestingly, we also observe increased autophagy in diabetic animals that is also dependent on the glucose concentration in the blood. Autophagy is a cellular condition that is induced upon removal of nutrients from a cell. Under these conditions, the cell will consume various organelles in an effort to produce additional energy to allow cell survival. This process is also important for the remodeling of cells and the recycling of certain organelles when new ones are produced. Autophagy has been implicated in several pathogenic states, including oncogenesis and diabetes. As can be seen in FIG. 12, these is increased conversion of microtubule-associated protein light chain 3 (LC3), a hallmark of elevated autophagy, in the skeletal muscle of diabetic mice. Both Akita and db/db mice show increased LC3 conversion that directly correlates with the elevation of blood glucose levels. These findings are similar to those seen in the beta cells of the pancreas in various models of diabetes, where increased autophagy is thought to contribute to the progression of diabetic pathology. Thus, these findings suggest that increased autophagy could contribute to the progression of diabetes by affecting the function of skeletal muscle as well. If the autophagy response in skeletal muscle could be modulated thought manipulation of the MG29 pathway or by other means, this could provide a therapeutic approach for diabetes.

Figure 13:
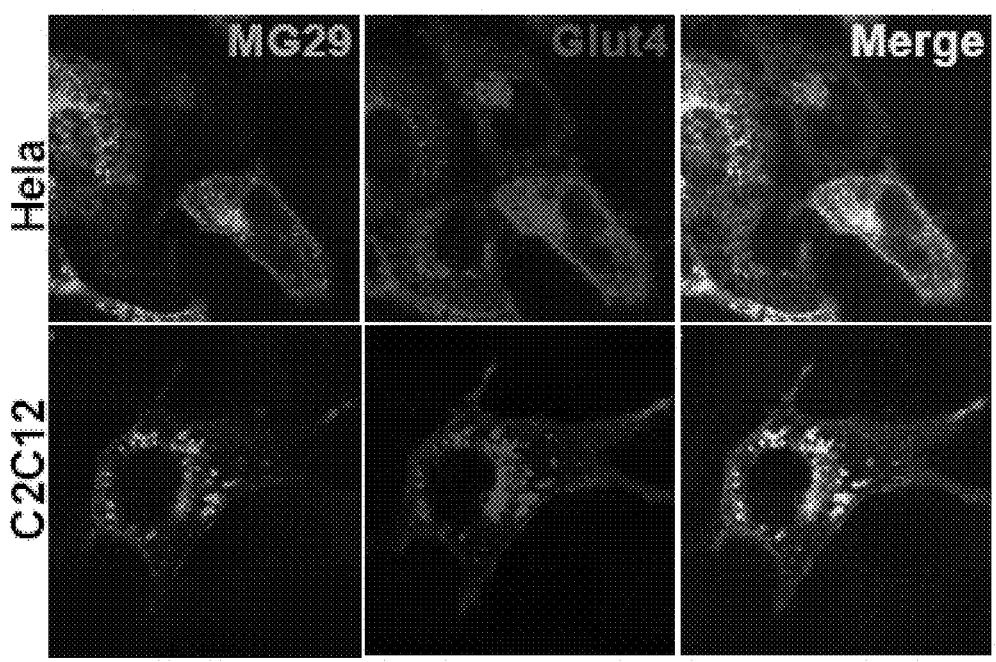
FIG. 13. MG29 and Glut4 are found in the same intracellular vesicles. Heterologous Hela cells (top) or homologous C2C12 cells (bottom) were co-transfected with GFP-MG29 or RFP-Glut4 fluorescent fusion proteins. Confocal microscopy revealed that these two proteins appear in the same intracellular vesicles in both cell types. This suggests that these two proteins could physically interact in vivo.

MG29 can facilitate Glut4 activity in muscle cells. Considering the diabetic susceptibility phenotype seen in the mg29−/− mouse it was necessary to determine if MG29 could have direct effects on the skeletal muscle machinery involved in glucose uptake from the blood. Our first series of experiments determined that MG29 and Glut4 can form a physical interaction complex in cells. We found that fluorescent fusion proteins of MG29 and Glut4 expressed in the same cell would co-localize in vesicle-like structures (FIG. 13*a*). This provides evidence that a physical interaction exists between two proteins.

Figure 14:
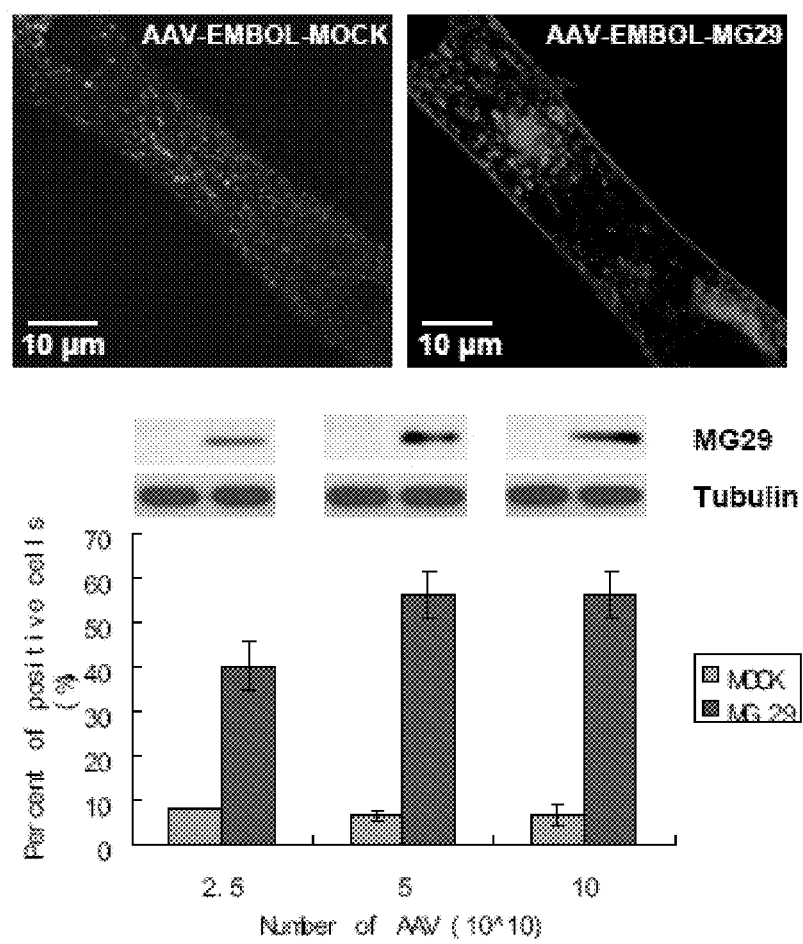
FIG. 14. C2C12 cells were transfected with GLUT4-EGFP, then infected with different amount of AAV virus as indicated in the figure. Twenty-five cells were examined randomly per dish, the cells which have GLUT4-EGFP membrane-distribution pattern were counted as positive cells. After that, western blotting was performed to detect MG29 level by using the cell lyses from all examined dishes. The data were collected from 3 individual experiments, total 75 cells were counted per each group.

We continued our studies to determine if this physical interaction had functional consequences within muscle cells. The C2C12 myogenic cell line does not express MG29 and has been shown in the past to be insensitive to insulin stimulation. When fluorescently tagged Glut4 is expressed in C2C12 cells, we found that altered Glut4 localization may contribute to the insulin insensitivity of C2C12 cells. Glut4 was primarily localized away from the plasma membrane where it would be incapable of taking up glucose (FIG. 14*a*). To determine if the lack of MG29 expression contributed to the aberrant localization of Glut4 in C2C12 cells, we generated an adeno-associated virus (AAV) that could express MG29 specifically in muscle cells (AAV-fgMG29) (FIG. 15*a*). When C2C12 cells were infected with this virus, they could express ample MG29 (FIG. 15*b*) while non-muscle HEK293 cells did not express MG29 when infected, confirming the muscle specific nature of the virus-induced expression. We found that we could also use this virus to increase gene expression in native skeletal muscle by injection into the muscles of living mice (FIG. 15*c*), which may prove to be an effective therapeutic approach for increasing the amount of MG29 expression in muscle. In the C2C12 cells, MG29 expression caused the Glut4 to appear on the plasma membrane much more frequently (FIG. 14*b*). We found that this was a dose dependent response where increased MG29 levels would directly lead to increased Glut4 appearance at the plasma membrane (FIG. 14*c*). These findings indicate that MG29 expression is necessary for proper Glut4 function and that increased MG29 expression can increase the Glut4 localization to the plasma membrane. If MG29 expression levels can be increased, perhaps through the application of AAV-fgMG29 or other pharmacological or molecular means, it is possible that enhanced Glut4 trafficking to the plasma membrane would enhance glucose uptake into muscle cells.

Figure 16:
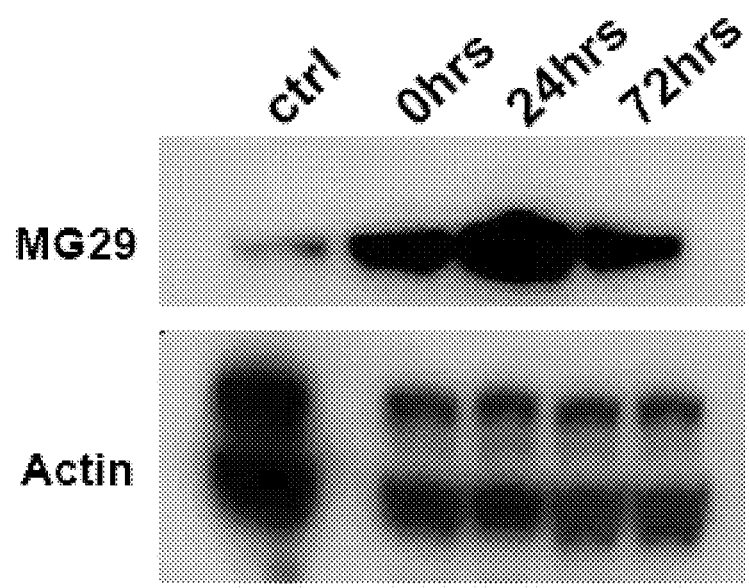
FIG. 16. MG29 protein expression is upregulated by exercise. Mice were subjected to a single bout of treadmill exercise, then muscles were dissected and examined for MG29 expression at various timepoints after the cessation of exercise. There is an immediate increase in MG29 expression that continues and reaches a peak at 24 hours after exercise. MG29 levels begin to return to baseline as time progresses. Actin levels are provided as a control for loading variation.

MG29 expression increases with exercise. Exercise can induce glucose uptake in muscle and has often been used as a life style change to help treat type II diabetic patients. Long-term exercise training has also been shown in the past to regulate the expression of a number of genes in skeletal muscle, particular those involved assembly of the contractile apparatus during physiological hypertrophy. However, there are few examples of genes that show significant increases in protein expression levels immediately following exercise, which is when Glut4 translocation to the plasma membrane is known to take place. During our examination of the role of MG29 in muscle fatigue and sarcopenia, we tested if MG29 expression is modified in mouse skeletal muscle following exercise. We found that MG29 expression levels immediately increase following a single round of treadmill running (FIG. 16). This increased expression peaked around 24 hours after the treadmill running Considering that reduced levels of MG29 in the mg29−/− mice or in aged skeletal muscle are linked with diminished muscle performance and increased fatigability, this transient increase in MG29 expression could be an adaptive response in skeletal muscle to acute exercise. Increased MG29 would act to bolster muscle performance and minimize fatigue under these conditions. If MG29 upregulation is part of such a response then inducing a further increased in MG29 expression might be sufficient to provide an additional improvement in skeletal muscle performance and increase glucose uptake into the muscle.

Figure 17:
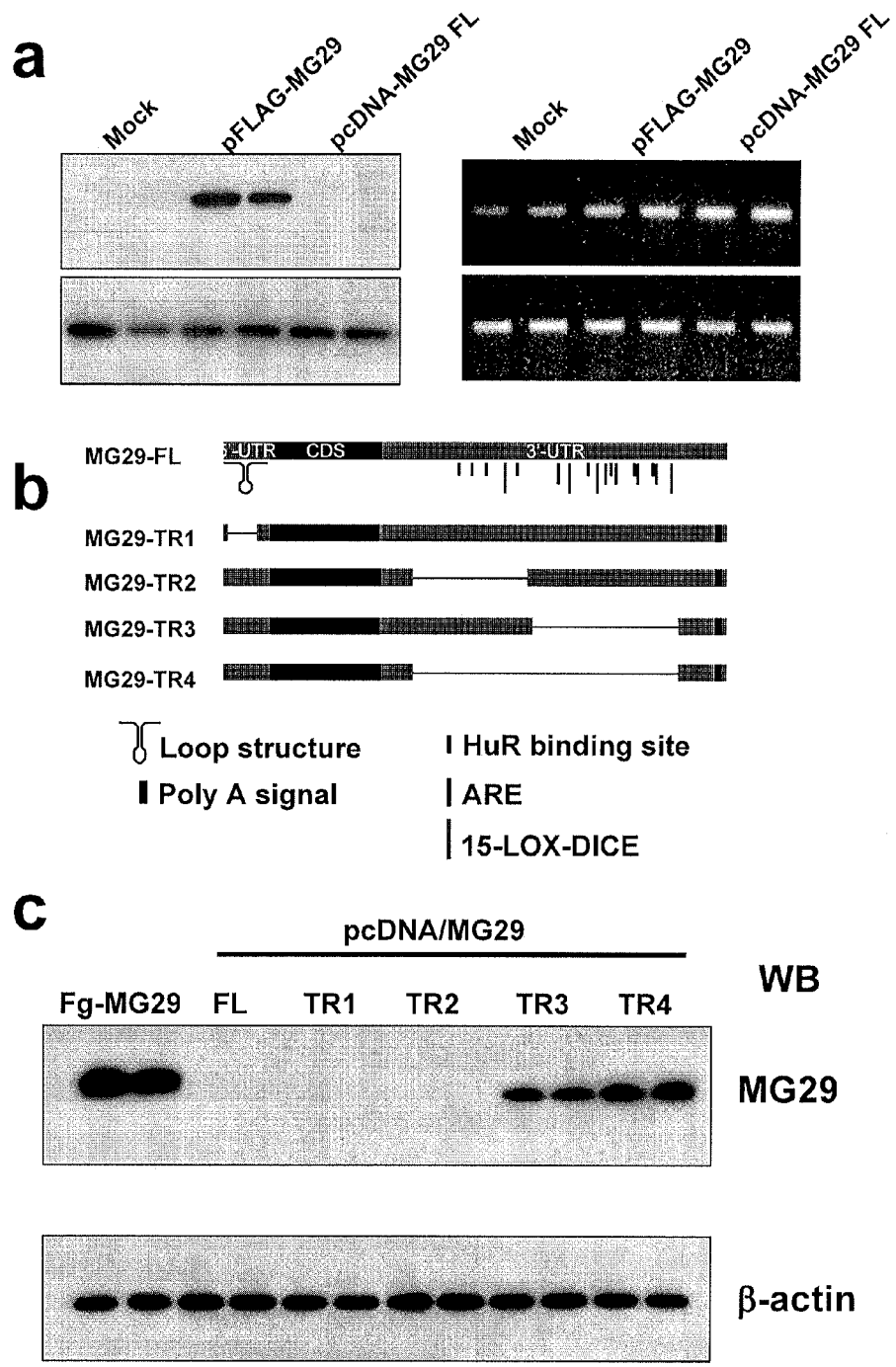
FIG. 17. Specific elements in the 3' UTR of the mg29 mRNA are essential for post-transcriptional regulation. (a) C2C12 myoblast cells are transfected with pFLAG-MG29 (mg29 cDNA sequence only) or pcDNA-MG29 (cDNA+3' UTR). Whole cell extracts used for Western blotting for MG29 and β-actin (left). Semi-quantitative RTPCR was also conducted on samples from these transfected C2C12 cells (right). Duplicate wells are from different experiments. Ample mg29 mRNA was present in all cells but protein was only seen when the 3' UTR was not present (i.e. pFLAG-MG29) indicating post-transcription regulation of MG29 is controlled by the 3' UTR. (b) A series of deletion constructs were assembled of the 3' UTR of the full-length murine mg29 mRNA. These expression plasmids contained the MG29 coding sequence and various deletions of the 3' UTR. (c) These deletion constructs were transfected into C2C12 myoblasts cells and after 3 days the cells were lysed for analysis by Western blot. While the mg29 coding sequence (Fg-MG29) an express readily in C2C12 cells, the full-length (FL) mRNA does not produce MG29 protein in C2C12 cells. Deletion constructs F1 and F2 do not produce MG29 protein, however the F3 and F4 constructs can produce ample protein. This indicates that the specific region at the 3' end of the UTR of the mg29 mRNA is required for post-transcriptional regulation.

MG29 expression undergoes post-transcriptional regulation. Considering the remarkable upregulation of MG29 expression following a short bout of treadmill exercise, we sought to better understand the cellular mechanisms that control MG29 expression. During this process, we observed that C2C12 myogenic cells do not express MG29 protein either in the myoblast stage or the differentiated myotube stage (FIG. 17a). When C2C12 myoblasts were differentiated into myotubes and harvested at different times no protein expression could be detected by Western blot, however ample MG29 mRNA expression could be detected by real-time PCR. These findings are highly suggestive that there is some level of control of MG29 translation that takes place at the level of the mRNA. If it is possible to resolve the molecular mechanism of this regulation it would provide a method to manipulate MG29 expression as the therapeutic approach against diabetes.

To understand the molecular mechanism controlling MG29 post-transcriptional regulation we examined the structure of the MG29 mRNA. We found that the 3' UTR in both the mouse and human mg29 mRNAs are considerably longer than an average 3' UTR for a mRNA in these species and bioinformatic modeling found major secondary structure is present in the 3' UTR regions of MG29 (data not shown). Deletion analysis of the 3' UTR established the specific region responsible for post-transcriptional regulation (FIG. 17b). This region contains several binding sites for accessory factors that either enhance or repress the translation of the mRNA. Three particularly interesting classes of sequences found we the HuR, ARE and 15-LOX-DICE sites. HuR sites regulate the stability and translation of mRNA in response to stress, such as oxidative stress. ARE (AU rich Element) are associated with mRNA destabilization. 15-LOX-DICE (15-LipOXygenase DIfferentiation Control Element) are bound by hnRNP E1 and K to inhibit initiation of translation. ARE (AU rich Element) are involved in mRNA destabilization.

Clearly, MG29 expression is regulated at the post-transcriptional level in a fashion that is dependent on the presence of the UTR of the native MG29 mRNA. Modulation of this regulatory pathway can increase the expression of MG29 in skeletal muscles. This has the potential to act as a therapeutic approach to diabetes by increasing the expression of MG29 protein. Another potential approach would be to increase the function of MG29 in the cell without necessarily increasing the expression of MG29.

Exemplary Materials and Methods

Cell transfection. The C2C12 murine myoblast cell line \was purchased from the American Type Culture Collection (Manassas, Va.). Cells were grown in a humidified environment at 37° C. and 5% $CO_2$ in DMEM medium for C2C12 or for HEK293 cells supplemented with 10% fetal bovine serum, 100 units/ml penicillin and 100 ug/ml streptomycin. In order to induce myotube differentiation, C2C12 myoblasts were grown to confluence and the medium was switched to DMEM containing 2% horse serum, penicillin (100 U/ml), streptomycin (100·g/ml). For transient transfections, C2C12 myoblasts or HEK293 cells were plated at 70% confluence in glass-bottom dishes or plastic multi-well tissue culture dishes. After 24 hours, cells were transfected with plasmids using GeneJammer reagent (Stratagene) as per manufacturer's directions. Cells were visualized by live cell confocal imaging at 24-48 hours after transfection or at times indicated for individual experiments. Other cells were used for isolation of mRNA or protein to conduct Western blotting and other biochemical experiments. In some experiments, C2C12 myoblasts were allowed to differentiate into myotubes for the indicated time before observation.

FDB skeletal muscle fiber isolation. Mice were sacrificed by cervical dislocation and hind limbs were surgically removed and placed into Isotonic Tyrode with measured osmolarity of 290 mOsm. Flexor Digitorum Brevis (FDB) muscles were excised and transferred into Tyrode supplemented with 0.2% type I collagenase (Sigma C-0310), for 90 minutes at 37° C. Muscle fibers were gently dissociated by several passages through a small diameter pipette. Isolated FDB muscle fibers were plated onto a ΔTC glass-bottomed dishes (Bioptech Inc.) in 1 ml of Tyrode buffer.

Confocal $Ca^{2+}$ imaging and spark analysis. Following individual muscle fiber isolation, the fibers were plated onto a dish containing isotonic tyrode solution (290 mOsm). 10 μM Fluo4-AM, a membrane permeable cytosolic $Ca^{2+}$ indicator dye is loaded onto the dish and left incubated for 60 minutes in room temperature along with different drug treatment. Replacing 50% of the dish volume with isotonic Tyrode for three times washed excess dye from the dish. Using brightfield confocal microscopy, fibers were then be screened by light microscopy for intact sarcolemmal membranes and regular striation patterns. Muscle fibers that fulfill these criteria were bathed in the isotonic solution, a physiological resting condition. Measurement of SR $Ca^{2+}$ release was performed on a BioRad Radiance-2100 confocal microscope equipped with Argon laser (479 nm), Helium-Neon laser (632 nm), and a 40×, 1.3 NA oil immersion objective. An acquisition rate of 2 ms perline was used for line scan imaging, while serial x-y images were acquired at 3.08 s per frame (512×512 pixels). Osmotic shock to disrupt the juxtaposition of membrane coupling was applied to analyze whether knockdown of Bin1 alters the $Ca^{2+}$ sparks activity. Initially, fiber was perfused with isotonic solution for 30 seconds prior to applying hypotonic Tyrode solution (170 mOsm) for 1 minute that induces membrane swelling. Solution was then quickly switched back to isotonic solution (290 mOsm) to observe the appearance of $Ca^{2+}$ spark activity upon membrane deformation. During this recording, the reversibility/plasticity nature of the $Ca^{2+}$ sparks, whether their activity are transient and return to a baseline are observed. For each animal, 3-4 fibers were treated by osmotic shock, and from each fiber 2 images (comprised of 30000 2 ms linescans of 512 pixels) were recorded. Image analysis and normalization of linescan intensities to the calculated resting fluorescence ($F_0$) and determination of the amplitude and duration of individual events was performed using custom routines for IDL software. Statistic data analysis was performed using OriginPro 6.0 software and comparison between different treatment groups were done using ANOVA.

Intact EDL and soleus muscle isolation. Intact EDL and soleus muscles were dissected from mice and maintained in Isotonic Tyrode solution supplemented with 12 mM glucose, continuously bubbled with 100% $O_2$. EDL muscles had a mean length of 12 mm and a mean mass of 80 mg, whereas soleus muscles had a mean length of 10 mm and a mean mass of 10 mg. Muscles were mounted vertically on a glass-stimulating apparatus (Radnoti) with platinum electrodes and attached to a movable isometric force transducer and to a stationary anchor, which allowed muscles to be stretched until both maximal forces for a given frequency and the frequency producing $T_{max}$ were obtained.

Force measurements during fatigue. A Powerlab computer-interface program (ADInstruments) was used to control the electrical stimulation protocols and to record, digitize and store force output data. Field stimulation (squared waves electrical currents of 500 ms duration, 300 mA using frequencies) was accomplished with platinum electrodes running on both sides of intact muscles. After mounting, EDL muscles were mounted in parallel and their resting lengths were adjusted to produce maximal isometric force ($T_{max}$). The muscles were then subjected to the force vs. frequency relationship (1~120 Hz) and fatiguing stimulation using frequencies produced 50% $T_{max}$. Following 20 min recovery at 50% Tmax frequency (1 min interval, 0.83% duty cycle), 100 nM final concentration of GLP1 was added into the treatment chamber and incubated for 1 h. Then another set of force vs. frequency, fatigue and recovery were performed. The values of Tmax and twitch force after GLP1 treatment was divided by the value before the treatment to evaluate the percentage of force decline in control group and GLP1 treatment group. The force vs. frequency relationship was plotted. Forces were normalized into gram after calibration and all data were analyzed by Origin software (OriginLab). Experiments were conducted at room temperature (23±2° C.) and comparison between groups was done using student t test.

Solutions. The isotonic balanced salt solutions consisted of (in mM) 5.5 glucose, 140 NaCl, 5 KCl, 2.5 $CaCl_2$, 2 $MgCl_2$ and 10 HEPES (ph 7.2), with measured osmolality of 290 mOsm. In the hypotonic solution, NaCl was adjusted to 70 mM to lower the osmolality to 170 mOsm. GLP1 7-36 Amide is dissolved in water to get final concentration of 10 nM for sparks measurements, and 100 nM for contractility experiment. Wortmannin is dissolved in 0.1% DMSO giving final concentration of 1 uM. All chemicals are obtained from Sigma.

Western Blot. Immunoblots were using standard techniques. Briefly, C2C12 or HEK293 cells were harvested and lysed with ice-cold modified RIPA buffer (150 mM NaCl, 5 mM EDTA, 1% NP40, 20 mM Tris-HCl, pH 7.5) in the presence of a cocktail of protease inhibitors (Sigma). 20·g of total protein were separated on a 4-12% SDS-polyacrylamide gel.

Treadmill running. Groups of 6 mice are placed on a leveled Exer-6M rodent treadmill (Columbus Instruments) equipped with an electric grid at the rear and are acclimated for four consecutive days. On day 1, they ran at a speed of 38 m/min for 5 min; on day 2, 48 m/min for 5 min; on day 3, 58 m/min for 5 min; and on day 4, 68 m/min for 5 min. On day 5, control and experimental mice run concomitantly at 88 m/min until exhaustion as indicated by falling on the electric grid twice, and running times until exhaustion are recorded. Three trials with three control and experimental mice each are conducted for each experimental condition.

Blood glucose measurements. Male and female mice were fasted overnight (16 hours), weighed, and administered with 2 g/kg body weight of 20% D-glucose solution by intraperitoneal-cavity (IP) injection. Tail-vein blood (approximately 10 μL) was collected before injection and at various times (15, 30, 45, 90, 120 minutes) post-injection for measurement of glucose content by a commercial glucose monitor (OneTouch Ultramini (LifeScan, Johnson & Johnson).

2-deoxyglucose uptake (2-DG) assay. Muscles (Soleus and EDL) were carefully dissected at the tendons and then immediately transferred to vials containing 2.0 ml Kreb's solution lacking glucose and containing 2 mM pyruvate and incubated in a shaking water bath (60 oscillations $min^{-1}$, 29° C., air phase in vial was continuously gassed with 95% $O_2$/5% $CO_2$) for 60 min. After 35 minutes equilibration, radiolabelled 2-DG (1 mM) and insulin (200 nM) were added and then incubated for an additional 25 min before samples were frozen in liquid nitrogen. For analysis of 2-DG uptake, muscles were added to Eppendorf tubes containing 0.5 ml of 1 N NaOH and heated at 55° C. for 60 min. The tubes were centrifuged and aliquots of the supernatant were added to scintillation cocktail and counted for $^{14}C$ and $^{3}H$ as described elsewhere (Shashkin P et al. (1995). *J Biol Chem* 270, 25613-25618). Glucose uptake rates are given in umol/25 min/ml of intracellular water. All experiments on whole muscles were performed in a paired fashion, i.e., one muscle without insulin and the contralateral muscle with insulin.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

The invention claimed is:

1. A method for modulating glucose uptake, comprising administering to a to subject in need thereof a composition comprising a pharmaceutically acceptable carrier and an effective amount of an agent that modulates mitsugumin29 (MG29) in a cell, wherein the agent is at least one of (i) a nucleic acid that encodes an MG29 polypeptide, or (ii) a nucleic acid that hybridizes specifically to an MG29 mRNA transcript, and wherein the agent is effective in modulating, MG29 and thereby, modulates glucose uptake.

2. The method of claim 1, wherein the cell is a muscle cell.

3. The method of claim 2, wherein the cell is a skeletal muscle cell.

4. The method of claim 1, wherein the agent comprises a nucleic acid encoding a polypeptide having at least 85% sequence identity to an MG29 polypeptide selected from the group consisting of SEQ ID NOs.: 1-8, and 26.

5. The method of claim 4, wherein the nucleic acid encodes an MG29 polypeptide as set forth in SEQ ID NO:3.

6. The method of claim 1, wherein the composition further includes a nucleic acid that inhibits the expression or activity of an MG29 mRNA binding protein.

7. The method of claim 6, wherein the inhibitory nucleic acid comprises RNA.

8. The method of claim 1, wherein the nucleic acid of (ii) is an inhibitory RNA that specifically hybridizes to an untranslated region (UTR) of an mRNA that encodes an MG29 polypeptide as set forth in at least one of SEQ ID NOs: 20-25.

9. The method of claim 7, wherein the inhibitory RNA is at least one of an antisense RNA, an interfering RNA or a combination of both.

10. The method of claim 9, wherein the interfering RNA is at least one of an siRNA, an miRNA or a combination of both.

11. A method of treating diabetes comprising identifying an individual in need thereof, and administering to an individual a composition comprising a pharmaceutically acceptable carrier and an effective amount of an agent that modulates mitsugumin29 (MG29), in a cell, wherein the agent is at least one of (i) a nucleic acid that encodes an MG29 polypeptide, or (ii) a nucleic acid that hybridizes specifically to an MG29 mRNA transcript, and wherein the agent is effective in modulating MG29, and thereby, treats diabetes.

12. The method of claim 11, wherein the composition is administered systemically.

13. The method of claim 11, wherein the agent (i) comprises a nucleic acid encoding an MG29 polypeptide as set forth in SEQ ID NOs.: 1-8, or 26.

14. The method of claim 13, wherein the nucleic acid encodes an MG29 polypeptide as set forth in SEQ ID NO:3.

15. The method of claim 11, wherein the composition further includes a nucleic acid that inhibits the expression or activity of an MG29 mRNA binding protein.

16. The method of claim 15, wherein the inhibitory nucleic acid comprises RNA.

17. The method of claim 16, wherein the inhibitory RNA is at least one of an antisense RNA, an interfering RNA or combination of both.

18. The method of claim 17, wherein the interfering RNA is at least one of an siRNA, an miRNA or combination thereof.

* * * * *